(12) United States Patent  
Cox et al.

(10) Patent No.: US 8,153,651 B2
(45) Date of Patent: Apr. 10, 2012

(54) AMIDE DERIVATIVES AS ION-CHANNEL LIGANDS AND PHARMACEUTICAL COMPOSITIONS AND METHODS OF USING THE SAME

(75) Inventors: Matthew Cox, San Francisco, CA (US); Donogh John Roger O'Mahony, San Mateo, CA (US); Maria De Los Angeles Estiarte-Martinez, San Francisco, CA (US); Tadashi Kawashima, Sandwich (GB); Satoshi Nagayama, Sandwich (GB); Yuji Shishido, Sandwich (GB); Hirotaka Tanaka, Sandwich (GB); Matthew Alexander James Duncton, San Bruno, CA (US); Andrew Antony Calabrese, Sandwich (GB)

(73) Assignee: Evotec AG, Hamburg (DE)

( * ) Notice: Subject to any disclaimer, the term of this patent is extended or adjusted under 35 U.S.C. 154(b) by 0 days.

(21) Appl. No.: 12/742,425

(22) PCT Filed: Nov. 13, 2008

(86) PCT No.: PCT/US2008/012763
§ 371 (c)(1),
(2), (4) Date: Sep. 14, 2010

(87) PCT Pub. No.: WO2009/064449
PCT Pub. Date: May 22, 2009

(65) Prior Publication Data
US 2011/0021514 A1   Jan. 27, 2011

Related U.S. Application Data

(60) Provisional application No. 61/002,838, filed on Nov. 13, 2007.

(51) Int. Cl.
*A01N 43/42* (2006.01)
*A61K 31/44* (2006.01)
*C07D 471/02* (2006.01)

(52) U.S. Cl. ......................... 514/299; 546/122
(58) Field of Classification Search .................. 546/122; 514/299
See application file for complete search history.

(56) References Cited

FOREIGN PATENT DOCUMENTS

| | | |
|---|---|---|
| DE | 287 263 | 2/1991 |
| WO | WO 2007/009558 | 8/2007 |
| WO | WO 2008/025821 | 3/2008 |

OTHER PUBLICATIONS

Pinedo et al, "Translational Research . . . ", The Oncologist 2000; 5(suppl1); 1-2. [www.The Oncologist.com].*
McMahon, G., VEGF Receptor Signaling in Tumor Angiogenisis. The Oncologist 2000;5(suppl 1):3-10. [www.The Oncologist.com].*

* cited by examiner

*Primary Examiner* — Paul V. Ward
(74) *Attorney, Agent, or Firm* — Klauber & Jackson LLC

(57) ABSTRACT

Compounds are disclosed that have a formula represented by the following:

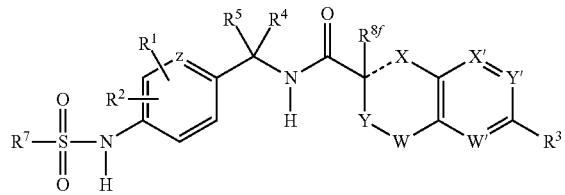

The compounds may be prepared as pharmaceutical compositions, and may be used for the prevention and treatment of a variety of conditions in mammals including humans, including by way of non-limiting example, pain, inflammation, traumatic injury, and others.

54 Claims, No Drawings

AMIDE DERIVATIVES AS ION-CHANNEL LIGANDS AND PHARMACEUTICAL COMPOSITIONS AND METHODS OF USING THE SAME

CROSS REFERENCE TO RELATED APPLICATIONS

The present application is a National Stage Application claiming the priority of co-pending PCT Application No. PCT/US2008/012763 filed Nov. 13, 2008, which in turn, claims priority from U.S. Provisional application Ser. No. 61/002,838, filed Nov. 13, 2007. Applicants claim the benefits of 35 U.S.C. §120 as to the PCT application and priority under 35 U.S.C. §119 as to the said U.S. Provisional application, and the entire disclosures of both applications are incorporated herein by reference in their entireties.

FIELD OF THE INVENTION

This invention relates to novel compounds and to pharmaceutical compositions containing such compounds. This invention also relates to methods for preventing and/or treating pain and inflammation-related conditions in mammals, such as (but not limited to) arthritis, Parkinson's disease, Alzheimer's disease, stroke, uveitis, asthma, myocardial infarction, the treatment and prophylaxis of pain syndromes (acute and chronic or neuropathic), traumatic brain injury, acute spinal cord injury, neurodegenerative disorders, alopecia (hair loss), inflammatory bowel disease, urinary incontinence, chronic obstructive pulmonary disease, irritable bowel disease, osteoarthritis, and autoimmune disorders, using the compounds and pharmaceutical compositions of the invention.

BACKGROUND OF THE INVENTION

Studies of signaling pathways in the body have revealed the existence of ion channels and sought to explain their role. Ion channels are integral membrane proteins with two distinctive characteristics: they are gated (open and closed) by specific signals such as membrane voltage or the direct binding of chemical ligands and, once open, they conduct ions across the cell membrane at very high rates.

There are many types of ion channels. Based on their selectivity to ions, they can be divided into calcium channel, potassium channel, sodium channel, etc. The calcium channel is more permeable to calcium ions than other types of ions, the potassium channel selects potassium ions over other ions, and so forth. Ion channels may also be classified according to their gating mechanisms. In a voltage-gated ion channel, the opening probability depends on the membrane voltage, whereas in a ligand-gated ion channel, the opening probability is regulated by the binding of small molecules (the ligands). Since ligand-gated ion channels receive signals from the ligand, they may also be considered as "receptors" for ligands.

Examples of ligand-gated ion channels include nAChR (nicotinic acetylcholine receptor) channel, GluR (glutamate receptor) channel, ATP-sensitive potassium channel, G-protein activated channel, cyclic-nucleotide-gated channel, etc.

Transient receptor potential (TRP) channel proteins constitute a large and diverse family of proteins that are expressed in many tissues and cell types. This family of channels mediates responses to nerve growth factors, pheromones, olfaction, tone of blood vessels and metabolic stress et al., and the channels are found in a variety of organisms, tissues and cell types including nonexcitable, smooth muscle and neuronal cells. Furthermore, TRP-related channel proteins are implicated in several diseases, such as several tumors and neurodegenerative disorders and the like. See, for example, Minke, et al., APStracts 9:0006P (2002).

Nociceptors are specialized primary afferent neurons and the first cells in a series of neurons that lead to the sensation of pain. The receptors in these cells can be activated by different noxious chemical or physical stimuli. The essential functions of nociceptors include the transduction of noxious stimuli into depolarizations that trigger action potentials, conduction of action potentials from primary sensory sites to synapses in the central nervous system, and conversion of action potentials into neurotransmitter release at presynaptic terminals, all of which depend on ion channels.

One TRP channel protein of particular interest is the vanilloid receptor. Also known as VR1, the vanilloid receptor is a non-selective cation channel which is activated or sensitized by a series of different stimuli including capsaicin, heat and acid stimulation and products of lipid bilayer metabolism (anandamide), and lipoxygenase metabolites. See, for example Smith, et al., *Nature*, 418:186-190 (2002). VR1 does not discriminate among monovalent cations, however, it exhibits a notable preference for divalent cations with a permeability sequence of $Ca^{2+}>Mg^{2+}>Na^+=K^+=Cs^+$. $Ca^{2+}$ is especially important to VR1 function, as extracellular $Ca^{2+}$ mediates desensitization, a process which enables a neuron to adapt to specific stimuli by diminishing its overall response to a particular chemical or physical signal. VR1 is highly expressed in primary sensory neurons in rats, mice and humans, and innervates many visceral organs including the dermis, bones, bladder, gastrointestinal tract and lungs. It is also expressed in other neuronal and non-neuronal tissues including the CNS, nuclei, kidney, stomach and T-cells. The VR1 channel is a member of the superfamily of ion channels with six membrane-spanning domains, with highest homology to the TRP family of ion channels.

VR1 gene knockout mice have been shown to have reduced sensory sensitivity to thermal and acid stimuli. See, for example, Caterina, et al. *Science,* 14:306-313 (2000). This supports the concept that VR1 contributes not only to generation of pain responses but also to the maintenance of basal activity of sensory nerves. VR1 agonists and antagonists have use as analgesics for the treatment of pain of various genesis or etiology, for example acute, inflammatory and neuropathic pain, dental pain and headache (such as migraine, cluster headache and tension headache). They are also useful as anti-inflammatory agents for the treatment of arthritis, Parkinson's Disease, Alzheimer's Disease, stroke, uveitis, asthma, myocardial infarction, the treatment and prophylaxis of pain syndromes (acute and chronic [neuropathic]), traumatic brain injury, spinal cord injury, neurodegenerative disorders, alopecia (hair loss), inflammatory bowel disease, irritable bowel disease and autoimmune disorders, renal disorders, obesity, eating disorders, cancer, schizophrenia, epilepsy, sleeping disorders, cognition, depression, anxiety, blood pressure, lipid disorders, osteoarthritis, and atherosclerosis.

Compounds, such as those of the present invention, which interact with the vanilloid receptor can thus play a role in treating or preventing or ameliorating these conditions.

A wide variety of Vanilloid compounds of different structures are known in the art, for example those disclosed in European Patent Application Numbers, EP 0 347 000 and EP 0 401 903, UK Patent Application Number GB 2226313 and International Patent Application, Publication Number WO 92/09285. Particularly notable examples of vanilloid compounds or vanilloid receptor modulators are capsaicin or trans 8-methyl-N-vanillyl-6-nonenamide which is isolated from the pepper plant, capsazepine (Tetrahedron, 53, 1997, 4791) and olvanil or— N-(4-hydroxy-3-methoxybenzyl)oleamide (J. Med. Chem., 36, 1993, 2595).

International Patent Application, Publication Number WO 02/08221 discloses diaryl piperazine and related compounds which bind with high selectivity and high affinity to vanilloid receptors, especially Type I Vanilloid receptors, also known as capsaicin or VR1 receptors. The compounds are said to be useful in the treatment of chronic and acute pain conditions, itch and urinary incontinence.

International Patent Application, Publication Numbers WO 02/16317, WO 02/16318 and WO 02/16319 suggest that compounds having a high affinity for the vanilloid receptor are useful for treating stomach-duodenal ulcers.

International Patent Application, Publication No. WO 2005/046683, published May 26, 2005, commonly owned, discloses a series of compounds that have demonstrated activity as VR-1 antagonists, and that are suggested as being useful for the treatment of conditions associated with VR-1 activity.

U.S. Pat. Nos. 3,424,760 and 3,424,761 both describe a series of 3-Ureidopyrrolidines that are said to exhibit analgesic, central nervous system, and pyschopharmacologic activities. These patents specifically disclose the compounds 1-(1-phenyl-3-pyrrolidinyl)-3-phenyl urea and 1-(1-phenyl-3-pyrrolidinyl)-3-(4-methoxyphenyl)urea respectively. International Patent Applications, Publication Numbers WO 01/62737 and WO 00/69849 disclose a series of pyrazole derivatives which are stated to be useful in the treatment of disorders and diseases associated with the NPY receptor subtype Y5, such as obesity. WO 01/62737 specifically discloses the compound 5-amino-N-isoquinolin-5-yl-1-[3-(trifluoromethyl)phenyl]-1H-pyrazole-3-carboxamide. WO 00/69849 specifically discloses the compounds 5-methyl-N-quinolin-8-yl-1-[3-(trifluoromethyl)phenyl]-1H-pyrazole-3-carboxamide, 5-methyl-N-quinolin-7-yl-1-[3-trifluoromethyl)phenyl]-1H-pyrazole-3-carboxamide, 5-methyl-N-quinolin-3-yl-1-[3-(trifluoromethyl)phenyl]-1H-pyrazole-3-carboxamide, N-isoquinolin-5-yl-5-methyl-1-[3-(trifluoromethyl)phenyl]-1H-pyrazole-3-carboxamide, 5-methyl-N-quinolin-5-yl-1-[3-(trifluoromethyl)phenyl]-1H-pyrazole-3-carboxamide, 1-(3-chlorophenyl)-N-isoquinolin-5-yl-5-methyl-1H-pyrazole-3-carboxamide, N-isoquinolin-5-yl-1-(3-methoxyphenyl)-5-methyl-1H-pyrazole-3-carboxamide, 1-(3-fluorophenyl)-N-isoquinolin-5-yl-5-methyl-1H-pyrazole-3-carboxamide, 1-(2-chloro-5-trifluoromethylphenyl)-N-isoquinolin-5-yl-5-methyl-1N-pyrazole-3-carboxamide, 5-methyl-N-(3-methylisoquinolin-5-yl)-1-[3-(trifluoromethyl)phenyl]-1N-pyrazole-3-carboxamide, 5-methyl-N-(1,2,3,4-tetrahydroisoquinolin-5-yl)-1-[3-(trifluoromethyl)phenyl]-1H-pyrazole-3-carboxamide.

German Patent Application Number 2502588 describes a series of piperazine derivatives. This application specifically discloses the compound N-[3-[2-(diethylamino) ethyl]-1,2-dihydro-4-methyl-2-oxo-7-quinolinyl]-4-phenyl-1-piperazinecarboxamide.

International Patent Application, Publication No. WO 05/003084 discloses 4-(methylsulfonylamino)phenyl analogs as vanilloid antagonists and their use as analgesics, and International Patent Application Publication No. WO02/16318 discloses thiourea derivatives as a modulator for vaniloid receptor and their use as analgesics.

We have now discovered that certain compounds have surprising potency and selectivity as VR-1 antagonists. The compounds of the present invention are considered to be particularly beneficial as VR-1 antagonists as certain compounds exhibit improved aqueous solubility and metabolic stability.

SUMMARY OF THE INVENTION

It has now been found that compounds such as those set forth herein, are capable of modifying mammalian ion channels such as the VR1 cation channel. Accordingly, the present compounds are potent VR1 antagonists with analgesic activity by systemic administration. The compounds of the present invention may show less toxicity, good absorption, good half-life, good solubility, low protein binding affinity, less drug-drug interaction, a reduced inhibitory activity at the HERG channel, reduced QT prolongation and good metabolic stability. This finding leads to novel compounds having therapeutic value. It also leads to pharmaceutical compositions having the compounds of the present invention as active ingredients and to their use to treat, prevent or ameliorate a range of conditions in mammals such as but not limited to pain of various genesis or etiology, for example acute, chronic, inflammatory and neuropathic pain, dental pain and headache (such as migraine, cluster headache and tension headache).

Accordingly, in a first aspect of the invention, compounds are disclosed that are capable of modifying ion channels, in vivo, having a formula I:

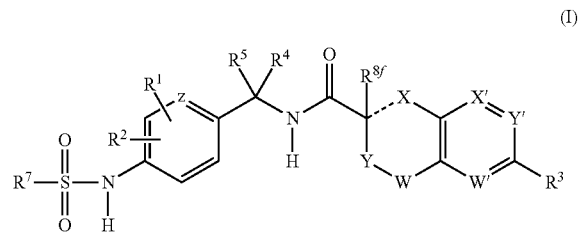

or a pharmaceutically acceptable salt thereof, and isotopic variants thereof, stereoisomers and tautomers thereof; wherein:
W represents O, $CR^{8a}R^{8b}$, or $NR^{8c}$;
X represents N, O, $CR^{8a}$, $CR^{8a}R^{8b}$, or $NR^{8c}$;
Y represents $CR^{8d}R^{8e}$;
W', X', Y' and Z each independently represent $CR^8$ or N; provided that W', X' and Y' are not all N at the same time;
$R^1$ and $R^2$ each independently represent hydrogen, halogen, hydroxy, substituted or unsubstituted alkyl, substituted or unsubstituted alkoxy, alkylthio, alkylsulfinyl or alkylsulfonyl;
$R^3$ represents hydrogen, halogen, hydroxy, substituted or unsubstituted alkyl, substituted or unsubstituted alkoxy, acyl, substituted or unsubstituted amino, substituted or unsubstituted alkylamino, substituted or unsubstituted dialkylamino, substituted or unsubstituted cycloalkyl, substituted or unsubstituted heterocycloalkyl, or substituted or unsubstituted heteroaryl;
$R^4$ and $R^5$ each independently represent hydrogen or substituted or unsubstituted alkyl;
$R^7$ represents ($C_1$-$C_6$)alkyl;
each $R^8$ independently represents hydrogen, halogen, hydroxy, substituted or unsubstituted alkyl, substituted or unsubstituted alkoxy, acyl, substituted or unsubstituted amino, substituted or unsubstituted alkylamino, substituted or unsubstituted dialkylamino, substituted or unsubstituted cycloalkyl, substituted or unsubstituted heterocycloalkyl, substituted or unsubstituted aryl, substituted or unsubstituted heteroaryl, alkylthio, alkylsulfinyl or alkylsulfonyl;

each $R^{8a}$, $R^{8b}$, $R^{8d}$, $R^{8e}$ and $R^{8f}$ independently represents hydrogen, halo, hydroxy, or substituted or unsubstituted alkyl; provided that when the dotted bond is a double bond $R^{8f}$ is absent;

$R^{8c}$ represents hydrogen, or substituted or unsubstituted alkyl; and the dotted bond represents a single or a double bond;

provided that i) when W and X both are O, and Y' is $CR^8$; then at least one of $R^3$ and $R^8$ is other than H; and ii) when W and X both are $CH_2$, W' is N, and Y' is $CR^8$; then at least one of $R^3$ and $R^8$ is other than H.

In one particular embodiment, with respect to compounds of formula I, W', X', Y' and Z each independently represent $CR^8$.

In another particular embodiment, with respect to compounds of formula I, one of W', X', Y' and Z represent N and the rest each independently represent $CR^8$.

In another particular embodiment, with respect to compounds of formula I, two of W', X', Y' and Z represent N and the rest each independently represent $CR^8$.

In another particular embodiment, with respect to compounds of formula I, W and X each independently represent $CR^{8a}R^{8b}$; and the dotted bond is a single bond.

In another particular embodiment, with respect to compounds of formula I, W and X each independently represent $CH_2$; and the dotted bond is a single bond.

In another particular embodiment, with respect to compounds of formula I, W represents $CR^{8a}R^{8b}$; X represents $CR^{8a}$; and the dotted bond is a double bond.

In another particular embodiment, with respect to compounds of formula I, W represents $CH_2$; X represents CH; and the dotted bond is a double bond.

In another particular embodiment, with respect to compounds of formula I, X represents $NR^{8c}$; and the dotted bond is a single bond.

In another particular embodiment, with respect to compounds of formula I, X represents O; and the dotted bond is a single bond.

In another particular embodiment, with respect to compounds of formula I, W represents $CR^{8a}R^{8b}$.

In another particular embodiment, with respect to compounds of formula I, wherein W represents $NR^{8c}$.

In another particular embodiment, with respect to compounds of formula I, wherein W represents O.

In another particular embodiment, with respect to compounds of formula I, Y represents $CR^{8d}R^{8e}$.

In another particular embodiment, with respect to compounds of formula I, Y represents $CH_2$.

In another particular embodiment, with respect to compounds of formula I, wherein Y represents $NR^{8c}$.

In another particular embodiment, with respect to compounds of formula I, wherein Y represents O.

In another embodiment, with respect to compounds of the invention, the compound is according to formula II

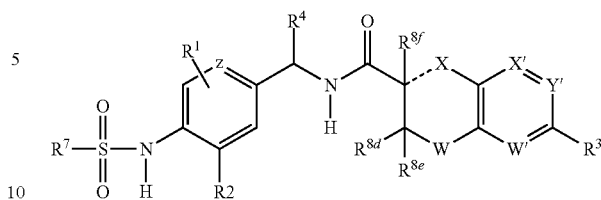

or a pharmaceutically acceptable salt, and isotopic variants thereof, stereoisomers and tautomers thereof, wherein W, W', X, X', Y', Z, and $R^7$ are as defined for formula I;

$R^1$ and $R^2$ each independently represent hydrogen, halogen, hydroxy, $(C_1-C_6)$alkyl, $(C_1-C_6)$alkoxy, hydroxy$(C_1-C_6)$alkoxy, $(C_1-C_6)$alkoxy-$(C_1-C_6)$alkyl, $(C_1-C_6)$alkoxy-$(C_1-C_6)$alkoxy, halo$(C_1-C_6)$alkyl, $(C_1-C_6)$alkylthio, $(C_1-C_6)$alkylsulfinyl or $(C_1-C_6)$alkylsulfonyl;

$R^3$ represents hydrogen, halogen, hydroxy, $(C_1-C_6)$alkyl, halo$(C_1-C_6)$alkyl, hydroxy$(C_1-C_6)$alkyl, halo hydroxy$(C_1-C_6)$alkyl, $(C_1-C_6)$alkoxy, hydroxy$(C_1-C_6)$alkoxy, $(C_1-C_6)$alkoxy-$(C_1-C_6)$alkyl, $(C_1-C_6)$acyl, $(C_1-C_6)$alkoxy-$(C_1-C_6)$alkoxy, $[(C_1-C_6)$alkyl$]NH—$, $[(C_1-C_6)$alkyl$]_2N—$, $[$hydroxy$(C_1-C_6)$alkyl$]NH—$, substituted or unsubstituted 3-6 membered cycloalkyl, $[$3-6 membered cycloalkyl$]$oxy, or $[$3-6 membered heterocycloalkyl$]$oxy or 3-6 membered heterocycloalkyl, unsubstituted or substituted with halo, $(C_1-C_6)$alkyl, halo$(C_1-C_6)$alkyl, hydroxy$(C_1-C_6)$alkyl, $(C_1-C_6)$alkoxy, $[(C_1-C_6)$alkyl$]_2N—$, or hydroxy, or 3-6 membered heteroaryl, 3-6 membered cycloalkyl $(C_1-C_6)$alkyl, or 3-6 membered cycloalkyl hydroxy $(C_1-C_6)$alkyl;

$R^4$ represents hydrogen, $(C_1-C_6)$alkyl, halogen, halo$(C_1-C_6)$alkyl, or hydroxy$(C_1-C_6)$alkyl;

each $R^8$ independently represents hydrogen, halogen, hydroxy, $(C_1-C_6)$alkyl, $(C_1-C_6)$alkoxy, hydroxy$(C_1-C_6)$alkoxy, $(C_1-C_6)$alkoxy-$(C_1-C_6)$alkyl, $(C_1-C_6)$alkoxy-$(C_1-C_6)$alkoxy, halo$(C_1-C_6)$alkyl, halo hydroxy$(C_1-C_6)$alkyl, $(C_1-C_6)$alkylthio, $(C_1-C_6)$alkylsulfinyl, $[(C_1-C_6)$alkyl$]NH—$, $[(C_1-C_6)$cycloalkyl$]NH—$, $[(C_1-C_6)$alkyl$]_2N—$, $[$hydroxy$(C_1-C_6)$alkyl$]NH—$, $[$3-6 membered cycloalkyl$]$oxy, $[$3-6 membered heterocycloalkyl$]$oxy or 3-6 membered heterocycloalkyl, unsubstituted or substituted with halo, $(C_1-C_6)$alkyl, $(C_1-C_6)$alkoxy, halo$(C_1-C_6)$alkyl, hydroxy$(C_1-C_6)$alkyl, aryl$(C_1-C_6)$alkyl, $[(C_1-C_6)$alkyl$]_2N—$, $(C_1-C_6)$carbalkoxy, hydroxy, aryl, $(C_1-C_6)$alkylaryl, halo$(C_1-C_6)$alkylaryl, haloaryl, $(C_1-C_6)$alkoxyaryl, or 3-10 membered heteroaryl, 3-6 membered cycloalkyl $(C_1-C_6)$alkyl, or 3-6 membered cycloalkyl hydroxy $(C_1-C_6)$alkyl or $(C_1-C_6)$alkylsulfonyl;

each $R^{8a}$, $R^{8b}$, $R^{8d}$, $R^{8e}$ and $R^{8f}$ independently represents hydrogen, halo, hydroxy, $(C_1-C_6)$alkyl, hydroxy$(C_1-C_6)$alkyl, $(C_1-C_6)$alkoxy-$(C_1-C_6)$alkyl, or halo$(C_1-C_6)$alkyl; provided that when the dotted bond is a double bond $R^{8f}$ is absent;

$R^{8c}$ represents hydrogen, $(C_1-C_6)$alkyl, hydroxy$(C_1-C_6)$alkyl, $(C_1-C_6)$alkoxy-$(C_1-C_6)$alkyl, cycloalkyl, or halo$(C_1-C_6)$allyl; and the dotted bond represents a single or a double bond.

The compounds of the present invention are useful for the treatment of inflammatory pain and associated hyperalgesia and allodynia. They are also useful for the treatment of neuropathic pain and associated hyperalgesia and allodynia (e.g. trigeminal or herpetic neuralgia, diabetic neuropathy, causalgia, sympathetically maintained pain and deafferentation syndromes such as brachial plexus avulsion). The compounds of the present invention are also useful as anti-inflammatory agents for the treatment of arthritis, and as agents to treat Parkinson's Disease, Alzheimer's Disease, stroke, uveitis, asthma, myocardial infarction, traumatic brain injury, spinal cord injury, neurodegenerative disorders, alopecia (hair loss), inflammatory bowel disease and autoimmune disorders, renal disorders, obesity, eating disorders, cancer, schizophrenia, epilepsy, sleeping disorders, cognition, depression, anxiety, blood pressure, lipid disorders, and atherosclerosis.

In one aspect, this invention provides compounds which are capable of modifying ion channels, in vivo. Representative ion channels so modified include voltage-gated channels and ligand-gated channels, including cation channels such as vanilloid channels.

In a further aspect, the present invention provides pharmaceutical compositions comprising a compound of the invention, and a pharmaceutical carrier, excipient or diluent. In this aspect of the invention, the pharmaceutical composition can comprise one or more of the compounds described herein.

In a further aspect of the invention, a method is disclosed for treating mammals, including humans, as well as lower mammalian species, susceptible to or afflicted with a condition from among those listed herein, and particularly, such condition as may be associated with e.g. arthritis, uveitis, asthma, myocardial infarction, traumatic brain injury, acute spinal cord injury, alopecia (hair loss), inflammatory bowel disease and autoimmune disorders, which method comprises administering an effective amount of one or more of the pharmaceutical compositions just described.

In yet another method of treatment aspect, this invention provides a method of treating a mammal susceptible to or afflicted with a condition that gives rise to pain responses or that relates to imbalances in the maintenance of basal activity of sensory nerves. Compounds have use as analgesics for the treatment of pain of various geneses or etiology, for example acute, inflammatory pain (such as pain associated with osteoarthritis and rheumatoid arthritis); various neuropathic pain syndromes (such as post-herpetic neuralgia, trigeminal neuralgia, reflex sympathetic dystrophy, diabetic neuropathy, Guillian Barre syndrome, fibromyalgia, phantom limb pain, post-masectomy pain, peripheral neuropathy, HIV neuropathy, and chemotherapy-induced and other iatrogenic neuropathies); visceral pain, (such as that associated with gastroesophageal reflex disease, irritable bowel syndrome, inflammatory bowel disease, pancreatitis, and various gynecological and urological disorders), dental pain and headache (such as migraine, cluster headache and tension headache).

In additional method of treatment aspects, this invention provides methods of treating a mammal susceptible to or afflicted with neurodegenerative diseases and disorders such as, for example Parkinson's disease, Alzheimer's disease and multiple sclerosis; diseases and disorders which are mediated by or result in neuroinflammation such as, for example traumatic brain injury, stroke, and encephalitis; centrally-mediated neuropsychiatric diseases and disorders such as, for example depression mania, bipolar disease, anxiety, schizophrenia, eating disorders, sleep disorders and cognition disorders; epilepsy and seizure disorders; prostate, bladder and bowel dysfunction such as, for example urinary incontinence, urinary hesitancy, rectal hypersensitivity, fecal incontinence, benign prostatic hypertrophy and inflammatory bowel disease; irritable bowel syndrome, over active bladder, respiratory and airway disease and disorders such as, for example, allergic rhinitis, asthma and reactive airway disease and chronic obstructive pulmonary disease; diseases and disorders which are mediated by or result in inflammation such as, for example rheumatoid arthritis and osteoarthritis, myocardial infarction, various autoimmune diseases and disorders, uveitis and atherosclerosis; itch/pruritus such as, for example psoriasis; alopecia (hair loss); obesity; lipid disorders; cancer; blood pressure; spinal cord injury; and renal disorders method comprises administering an effective condition-treating or condition-preventing amount of one or more of the pharmaceutical compositions just described.

In addition to the methods of treatment set forth above, the present invention extends to the use of any of the compounds of the invention for the preparation of medicaments that may be administered for such treatments, as well as to such compounds for use in the treatments disclosed and specified.

In additional aspects, this invention provides methods for synthesizing the compounds of the invention, with representative synthetic protocols and pathways disclosed later on herein.

Other objects and advantages will become apparent to those skilled in the art from a consideration of the ensuing detailed description.

DETAILED DESCRIPTION OF THE PREFERRED EMBODIMENTS

Definitions

When describing the compounds, pharmaceutical compositions containing such compounds and methods of using such compounds and compositions, the following terms have the following meanings unless otherwise indicated. It should be further understood that the terms "groups" and "radicals" can be considered interchangeable when used herein.

"Acyl" refers to a radical —C(O)$R^{20}$, where $R^{20}$ is hydrogen, alkyl, cycloalkyl, cycloheteroalkyl, aryl, arylalkyl, heteroalkyl, heteroaryl, heteroarylalkyl as defined herein. Representative examples include, but are not limited to, formyl, acetyl, cyclohexylcarbonyl, cyclohexylmethylcarbonyl, benzoyl, benzylcarbonyl and the like.

"Acylamino" refers to a radical —$NR^{21}$C(O)$R^{22}$, where $R^{21}$ is hydrogen, alkyl, cycloalkyl, cycloheteroalkyl, aryl, arylalkyl, heteroalkyl, heteroaryl, heteroarylalkyl and $R^{22}$ is hydrogen, alkyl, alkoxy, cycloalkyl, cycloheteroalkyl, aryl, arylalkyl, heteroalkyl, heteroaryl or heteroarylalkyl, as defined herein. Representative examples include, but are not limited to, formylamino, acetylamino, cyclohexylcarbonylamino, cyclohexylmethyl-carbonylamino, benzoylamino, benzylcarbonylamino and the like.

"Acyloxy" refers to the group —OC(O)$R^{23}$ where $R^{23}$ is hydrogen, alkyl, aryl or cycloalkyl.

"Substituted alkenyl" refers to those groups recited in the definition of "substituted" herein, and particularly refers to an alkenyl group having 1 or more substituents, for instance from 1 to 5 substituents, and particularly from 1 to 3 substituents, selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, keto, nitro, thioalkoxy, substituted thioalkoxy, thioaryloxy, thioketo, thiol, alkyl-S(O)—, aryl-S(O)—, alkyl-S(O)$_2$— and aryl-S(O)$_2$—.

"Alkoxy" refers to the group —OR$^{24}$ where R$^{24}$ is alkyl. Particular alkoxy groups include, by way of example, methoxy, ethoxy, n-propoxy, isopropoxy, n-butoxy, tert-butoxy, sec-butoxy, n-pentoxy, n-hexoxy, 1,2-dimethylbutoxy, and the like.

"Substituted alkoxy" refers to those groups recited in the definition of "substituted" herein, and particularly refers to an alkoxy group having 1 or more substituents, for instance from 1 to 5 substituents, and particularly from 1 to 3 substituents, selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, heteroaryl, hydroxyl, keto, nitro, thioalkoxy, substituted thioalkoxy, thioaryloxy, thioketo, thiol, alkyl-S(O)—, aryl-S(O)—, alkyl-S(O)$_2$— and aryl-S(O)$_2$—.

"Alkoxycarbonylamino" refers to the group —NR$^{25}$C(O)OR$^{26}$, where R$^{25}$ is hydrogen, alkyl, aryl or cycloalkyl, and R$^{26}$ is alkyl or cycloalkyl.

"Alkyl" refers to monovalent saturated alkane radical groups particularly having up to about 11 carbon atoms, more particularly as a lower alkyl, from 1 to 8 carbon atoms and still more particularly, from 1 to 6 carbon atoms. The hydrocarbon chain may be either straight-chained or branched. This term is exemplified by groups such as methyl, ethyl, n-propyl, isopropyl, n-butyl, iso-butyl, tert-butyl, n-hexyl, n-octyl, tert-octyl and the like. The term "lower alkyl" refers to alkyl groups having 1 to 6 carbon atoms. The term "alkyl" also refers to "cycloalkyl" as defined below.

"Substituted alkyl" refers to those groups recited in the definition of "substituted" herein, and particularly refers to an alkyl group having 1 or more substituents, for instance from 1 to 5 substituents, and particularly from 1 to 3 substituents, selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, heteroaryl, keto, nitro, thioalkoxy, substituted thioalkoxy, thioaryloxy, thioketo, thiol, alkyl-S(O)—, aryl-S(O)—, alkyl-S(O)$_2$—, and aryl-S(O)$_2$—.

"Alkylene" refers to divalent saturated alkene radical groups having 1 to 11 carbon atoms and more particularly 1 to 6 carbon atoms which can be straight-chained or branched. This term is exemplified by groups such as methylene (—CH$_2$—), ethylene (—CH$_2$CH$_2$—), the propylene isomers (e.g., —CH$_2$CH$_2$CH$_2$— and —CH(CH$_3$)CH$_2$—) and the like.

"Substituted alkylene" refers to those groups recited in the definition of "substituted" herein, and particularly refers to an alkylene group having 1 or more substituents, for instance from 1 to 5 substituents, and particularly from 1 to 3 substituents, selected from the group consisting of acyl, acylamino, acyloxy, alkoxy, substituted alkoxy, alkoxycarbonyl, alkoxycarbonylamino, amino, substituted amino, aminocarbonyl, amino-carbonylamino, aminocarbonyloxy, aryl, aryloxy, azido, carboxyl, cyano, halogen, hydroxyl, keto, nitro, thioalkoxy, substituted thioalkoxy, thioaryloxy, thioketo, thiol, alkyl-S(O)—, aryl-S(O)—, alkyl-S(O)$_2$— and aryl-S(O)$_2$—.

"Alkenyl" refers to monovalent olefinically unsaturated hydrocarbyl groups preferably having 2 to 11 carbon atoms, particularly, from 2 to 8 carbon atoms, and more particularly, from 2 to 6 carbon atoms, which can be straight-chained or branched and having at least 1 and particularly from 1 to 2 sites of olefinic unsaturation. Particular alkenyl groups include ethenyl (—CH=CH$_2$), n-propenyl (—CH$_2$CH=CH$_2$), isopropenyl (—C(CH$_3$)=CH$_2$), vinyl and substituted vinyl, and the like.

"Alkenylene" refers to divalent olefinically unsaturated hydrocarbyl groups particularly having up to about 11 carbon atoms and more particularly 2 to 6 carbon atoms which can be straight-chained or branched and having at least 1 and particularly from 1 to 2 sites of olefinic unsaturation. This term is exemplified by groups such as ethenylene (—CH=CH—), the propenylene isomers (e.g., —CH=CHCH$_2$— and —C(CH$_3$)=CH— and —CH=C(CH$_3$)—) and the like.

"Alkynyl" refers to acetylenically or alkynically unsaturated hydrocarbyl groups particularly having 2 to 11 carbon atoms, and more particularly 2 to 6 carbon atoms which can be straight-chained or branched and having at least 1 and particularly from 1 to 2 sites of alkynyl unsaturation. Particular non-limiting examples of alkynyl groups include acetylenic, ethynyl (—C≡CH), propargyl (—CH$_2$CF—CH), and the like.

"Substituted alkynyl" refers to those groups recited in the definition of "substituted" herein, and particularly refers to an alkynyl group having 1 or more substituents, for instance from 1 to 5 substituents, and particularly from 1 to 3 substituents, selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, keto, nitro, thioalkoxy, substituted thioalkoxy, thioaryloxy, thioketo, thiol, alkyl-S(O)—, aryl-S(O)—, alkyl-S(O)$_2$— and aryl-S(O)$_2$—.

"Alkanoyl" or "acyl" as used herein refers to the group R$^{27}$—C(O)—, where R$^{27}$ is hydrogen or alkyl as defined above.

"Aryl" refers to a monovalent aromatic hydrocarbon group derived by the removal of one hydrogen atom from a single carbon atom of a parent aromatic ring system. Typical aryl groups include, but are not limited to, groups derived from aceanthrylene, acenaphthylene, acephenanthrylene, anthracene, azulene, benzene, chrysene, coronene, fluoranthene, fluorene, hexacene, hexaphene, hexylene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene and the like. Particularly, an aryl group comprises from 6 to 14 carbon atoms.

"Substituted Aryl" refers to those groups recited in the definition of "substituted" herein, and particularly refers to an aryl group that may optionally be substituted with 1 or more substituents, for instance from 1 to 5 substituents, particularly 1 to 3 substituents, selected from the group consisting of acyl, acylamino, acyloxy, alkenyl, substituted alkenyl, alkoxy, substituted alkoxy, alkoxycarbonyl, alkyl, substituted alkyl, alkynyl, substituted alkynyl, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, nitro, thioalkoxy, substituted thioalkoxy, thioaryloxy, thiol, alkyl-S(O)—, aryl-S(O)—, alkyl-S(O)$_2$— and aryl-S(O)$_2$—.

"Fused Aryl" refers to an aryl having two of its ring carbon in common with a second aryl ring or with an aliphatic ring.

"Alkaryl" refers to an aryl group, as defined above, substituted with one or more alkyl groups, as defined above.

"Aralkyl" or "arylalkyl" refers to an alkyl group, as defined above, substituted with one or more aryl groups, as defined above.

"Aryloxy" refers to —O-aryl groups wherein "aryl" is as defined above.

"Alkylamino" refers to the group alkyl-$NR^{28}R^{29}$, wherein each of $R^{28}$ and $R^{29}$ are independently selected from hydrogen and alkyl.

"Arylamino" refers to the group aryl-$NR^{30}R^{31}$, wherein each of $R^{30}$ and $R^{31}$ are independently selected from hydrogen, aryl and heteroaryl.

"Alkoxyamino" refers to a radical —$N(H)OR^{32}$ where $R^{32}$ represents an alkyl or cycloalkyl group as defined herein.

"Alkoxycarbonyl" refers to a radical —C(O)-alkoxy where alkoxy is as defined herein.

"Alkylarylamino" refers to a radical —$NR^{33}R^{34}$ where $R^{33}$ represents an alkyl or cycloalkyl group and $R^{34}$ is an aryl as defined herein.

"Alkylsulfonyl" refers to a radical —$S(O)_2R^{35}$ where $R^{35}$ is an alkyl or cycloalkyl group as defined herein. Representative examples include, but are not limited to, methylsulfonyl, ethylsulfonyl, propylsulfonyl, butylsulfonyl and the like.

"Alkylsulfinyl" refers to a radical —$S(O)R^{35}$ where $R^{35}$ is an alkyl or cycloalkyl group as defined herein. Representative examples include, but are not limited to, methylsulfinyl, ethylsulfinyl, propylsulfinyl, butylsulfinyl and the like.

"Alkylthio" refers to a radical —$SR^{35}$ where $R^{35}$ is an alkyl or cycloalkyl group as defined herein that may be optionally substituted as defined herein. Representative examples include, but are not limited to, methylthio, ethylthio, propylthio, butylthio, and the like.

"Amino" refers to the radical —$NH_2$.

"Substituted amino" refers to those groups recited in the definition of "substituted" herein, and particularly refers to the group —$N(R^{36})_2$ where each $R^{36}$ is independently selected from the group consisting of hydrogen, alkyl, substituted alkyl, alkenyl, substituted alkenyl, alkynyl, substituted alkynyl, aryl, cycloalkyl, substituted cycloalkyl, and where both R groups are joined to form an alkylene group. When both R groups are hydrogen, —$N(R^{36})_2$ is an amino group.

"Aminocarbonyl" refers to the group —$C(O)NR^{37}R^{37}$ where each $R^{37}$ is independently hydrogen, alkyl, aryl and cycloalkyl, or where the $R^{37}$ groups are joined to form an alkylene group.

"Aminocarbonylamino" refers to the group —$NR^{38}C(O)NR^{38}R^{38}$ where each $R^{38}$ is independently hydrogen, alkyl, aryl or cycloalkyl, or where two R groups are joined to form an alkylene group.

"Aminocarbonyloxy" refers to the group —$OC(O)NR^{39}R^{39}$ where each $R^{39}$ is independently hydrogen, alkyl, aryl or cycloalkyl, or where the R groups are joined to form an alkylene group.

"Arylalkyloxy" refers to an —O-arylalkyl radical where arylalkyl is as defined herein.

"Arylamino" means a radical —$NHR^{40}$ where $R^{40}$ represents an aryl group as defined herein.

"Aryloxycarbonyl" refers to a radical —C(O)—O-aryl where aryl is as defined herein.

"Arylsulfonyl" refers to a radical —$S(O)_2R^{41}$ where $R^{41}$ is an aryl or heteroaryl group as defined herein.

"Azido" refers to the radical —$N_3$.

"Bicycloaryl" refers to a monovalent aromatic hydrocarbon group derived by the removal of one hydrogen atom from a single carbon atom of a parent bicycloaromatic ring system. Typical bicycloaryl groups include, but are not limited to, groups derived from indane, indene, naphthalene, tetrahydronaphthalene, and the like. Particularly, an aryl group comprises from 8 to 11 carbon atoms.

"Bicycloheteroaryl" refers to a monovalent bicycloheteroaromatic group derived by the removal of one hydrogen atom from a single atom of a parent bicycloheteroaromatic ring system. Typical bicycloheteroaryl groups include, but are not limited to, groups derived from benzofuran, benzimidazole, benzindazole, benzdioxane, chromene, chromane, cinnoline, phthalazine, indole, indoline, indolizine, isobenzofuran, isochromene, isoindole, isoindoline, isoquinoline, benzothiazole, benzoxazole, naphthyridine, benzoxadiazole, pteridine, purine, benzopyran, benzpyrazine, pyridopyrimidine, quinazoline, quinoline, quinolizine, quinoxaline, benzomorphan, tetrahydroisoquinoline, tetrahydroquinoline, and the like. Preferably, the bicycloheteroaryl group is between 9-11 membered bicycloheteroaryl, with 5-10 membered heteroaryl being particularly preferred. Particular bicycloheteroaryl groups are those derived from benzothiophene, benzofuran, benzothiazole, indole, quinoline, isoquinoline, benzimidazole, benzoxazole and benzdioxane.

"Carbamoyl" refers to the radical —$C(O)N(R^{42})_2$ where each $R^{42}$ group is independently hydrogen, alkyl, cycloalkyl or aryl, as defined herein, which may be optionally substituted as defined herein.

"Carboxy" refers to the radical —C(O)OH.

"Carboxyamino" refers to the radical —N(H)C(O)OH.

"Cycloalkyl" refers to cyclic hydrocarbyl groups having from 3 to about 10 carbon atoms and having a single cyclic ring or multiple condensed rings, including fused and bridged ring systems, which optionally can be substituted with from 1 to 3 alkyl groups. Such cycloalkyl groups include, by way of example, single ring structures such as cyclopropyl, cyclobutyl, cyclopentyl, cyclooctyl, 1-methylcyclopropyl, 2-methylcyclopentyl, 2-methylcyclooctyl, and the like, and multiple ring structures such as adamantanyl, and the like.

"Substituted cycloalkyl" refers to those groups recited in the definition of "substituted" herein, and particularly refers to a cycloalkyl group having 1 or more substituents, for instance from 1 to 5 substituents, and particularly from 1 to 3 substituents, selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, keto, nitro, thioalkoxy, substituted thioalkoxy, thioaryloxy, thioketo, thiol, alkyl-S(O)—, aryl-S(O)—, alkyl-$S(O)_2$— and aryl-$S(O)_2$—.

"Cycloalkoxy" refers to the group —$OR^{43}$ where $R^{43}$ is cycloalkyl. Such cycloalkoxy groups include, by way of example, cyclopentoxy, cyclohexoxy and the like.

"Cycloalkenyl" refers to cyclic hydrocarbyl groups having from 3 to 10 carbon atoms and having a single cyclic ring or multiple condensed rings, including fused and bridged ring systems and having at least one and particularly from 1 to 2 sites of olefinic unsaturation. Such cycloalkenyl groups include, by way of example, single ring structures such as cyclohexenyl, cyclopentenyl, cyclopropenyl, and the like.

"Substituted cycloalkenyl" refers to those groups recited in the definition of "substituted" herein, and particularly refers to a cycloalkenyl group having 1 or more substituents, for instance from 1 to 5 substituents, and particularly from 1 to 3 substituents, selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, keto, nitro, thioalkoxy, substituted thioalkoxy, thioaryloxy, thioketo, thiol, alkyl-S(O)—, aryl-S(O)—, alkyl-$S(O)_2$— and aryl-$S(O)_2$—.

"Fused Cycloalkenyl" refers to a cycloalkenyl having two of its ring carbon atoms in common with a second aliphatic or aromatic ring and having its olefinic unsaturation located to impart aromaticity to the cycloalkenyl ring.

"Cyanato" refers to the radical —OCN.

"Cyano" refers to the radical —CN.

"Dialkylamino" means a radical —NR$^{44}$R$^{45}$ where R$^{44}$ and R$^{45}$ independently represent an alkyl, substituted alkyl, aryl, substituted aryl, cycloalkyl, substituted cycloalkyl, cycloheteroalkyl, substituted cycloheteroalkyl, heteroaryl, or substituted heteroaryl group as defined herein.

"Ethenyl" refers to substituted or unsubstituted —(C=C)—.

"Ethylene" refers to substituted or unsubstituted —(C—C)—.

"Ethynyl" refers to —(C≡C)—.

"Halo" or "halogen" refers to fluoro, chloro, bromo and iodo. Preferred halo groups are either fluoro or chloro.

"Hydroxy" refers to the radical —OH.

"Nitro" refers to the radical —NO$_2$.

"Substituted" refers to a group in which one or more hydrogen atoms are each independently replaced with the same or different substituent(s). Typical substituents include, but are not limited to, -X, -R$^{46}$, —O$^-$, =O, —OR$^{46}$, —SR$^{46}$, —S$^-$, =S, —NR$^{46}$R$^{47}$, =NR$^{46}$, —CX$_3$, —CF$_3$, —CN, —OCN, —SCN, —NO, —NO$_2$, =N$_2$, —N$_3$, —S(O)$_2$O$^-$, —S(O)$_2$OH, —S(O)$_2$R$^{46}$, —OS(O$_2$)O$^-$, —OS(O)$_2$R$^{46}$, —P(O)(O$^-$)$_2$, —P(O)(OR$^{46}$)(O$^-$), —OP(O)(OR$^{46}$)(OR$^{47}$), —C(O)R$^{46}$, —C(S)R$^{46}$, —C(O)OR$^{46}$, —C(O)NR$^{46}$R$^{47}$, —C(O)O$^-$, —C(S)OR$^{46}$, —NR$^{48}$C(O)NR$^{46}$R$^{47}$, —NR$^{48}$C(S)NR$^{46}$R$^{47}$, —NR$^{49}$C(NR$^{48}$)NR$^{46}$R$^{47}$ and —C(NR$^{48}$)NR$^{46}$R$^{47}$, where each X is independently a halogen; each R$^{46}$, R$^{47}$, R$^{48}$ and R$^{49}$ are independently hydrogen, alkyl, substituted alkyl, aryl, substituted alkyl, arylalkyl, substituted alkyl, cycloalkyl, substituted alkyl, cycloheteroalkyl, substituted cycloheteroalkyl, heteroalkyl, substituted heteroalkyl, heteroaryl, substituted heteroaryl, heteroarylalkyl, substituted heteroarylalkyl, —NR$^{50}$R$^{51}$, —C(O)R$^{50}$ or —S(O)$_2$R$^{50}$ or optionally R$^{50}$ and R$^{51}$ together with the atom to which they are both attached form a cycloheteroalkyl or substituted cycloheteroalkyl ring; and R$^{50}$ and R$^{51}$ are independently hydrogen, alkyl, substituted alkyl, aryl, substituted alkyl, arylalkyl, substituted alkyl, cycloalkyl, substituted alkyl, cycloheteroalkyl, substituted cycloheteroalkyl, heteroalkyl, substituted heteroalkyl, heteroaryl, substituted heteroaryl, heteroarylalkyl or substituted heteroarylalkyl.

Examples of representative substituted aryls include the following

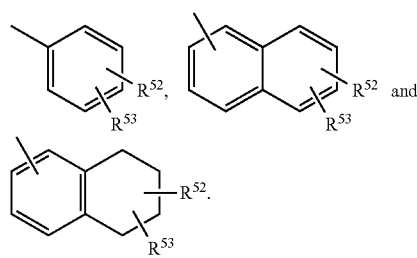

In these formulae one of R$^{52}$ and R$^{53}$ may be hydrogen and at least one of R$^{52}$ and R$^{53}$ is each independently selected from alkyl, alkenyl, alkynyl, cycloheteroalkyl, alkanoyl, alkoxy, aryloxy, heteroaryloxy, alkylamino, arylamino, heteroarylamino, NR$^{54}$COR$^{55}$, NR$^{54}$SOR$^{55}$, NR$^{54}$SO$_2$R$^{52}$, COOalkyl, COOaryl, CONR$^{54}$R$^{55}$, CONR$^{54}$OR$^{55}$, NR$^{54}$R$^{55}$, SO$_2$NR$^{54}$R$^{55}$, S-alkyl, S-alkyl, SOalkyl, SO$_2$alkyl Saryl, SOaryl, SO$_2$aryl; or R$^{52}$ and R$^{53}$ may be joined to form a cyclic ring (saturated or unsaturated) from 5 to 8 atoms, optionally containing one or more heteroatoms selected from the group N, O or S. R$^{54}$, R$^{55}$, and R$^{56}$ are independently hydrogen, alkyl, alkenyl, alkynyl, perfluoroalkyl, cycloalkyl, cycloheteroalkyl, aryl, substituted aryl, heteroaryl, substituted or hetero alkyl or the like.

"Hetero" when used to describe a compound or a group present on a compound means that one or more carbon atoms in the compound or group have been replaced by a nitrogen, oxygen, or sulfur heteroatom. Hetero may be applied to any of the hydrocarbyl groups described above such as alkyl, e.g. heteroalkyl, cycloalkyl, e.g. cycloheteroalkyl, aryl, e.g. heteroaryl, cycloalkenyl, cycloheteroalkenyl, and the like having from 1 to 5, and especially from 1 to 3 heteroatoms.

"Heteroaryl" refers to a monovalent heteroaromatic group derived by the removal of one hydrogen atom from a single atom of a parent heteroaromatic ring system. Typical heteroaryl groups include, but are not limited to, groups derived from acridine, arsindole, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like. Preferably, the heteroaryl group is between 5-15 membered heteroaryl, with 5-10 membered heteroaryl being particularly preferred. Particular heteroaryl groups are those derived from thiophene, pyrrole, benzothiophene, benzofuran, indole, pyridine, quinoline, imidazole, oxazole and pyrazine.

Examples of representative heteroaryls include the following:

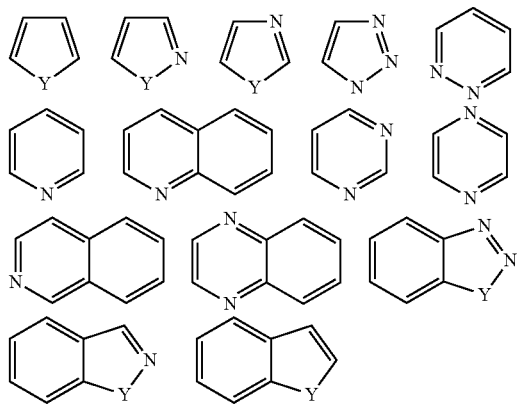

wherein each Y is selected from carbonyl, N, NR$^{58}$, O, and S; and R$^{58}$ is independently hydrogen, alkyl, cycloalkyl, cycloheteroalkyl, aryl, heteroaryl, heteroalkyl or the like.

As used herein, the term "cycloheteroalkyl" refers to a stable heterocyclic non-aromatic ring and fused rings containing one or more heteroatoms independently selected from N, O and S. A fused heterocyclic ring system may include carbocyclic rings and need only include one heterocyclic ring. Examples of heterocyclic rings include, but are not limited to, piperazinyl, homopiperazinyl, piperidinyl and morpholinyl, and are shown in the following illustrative examples:

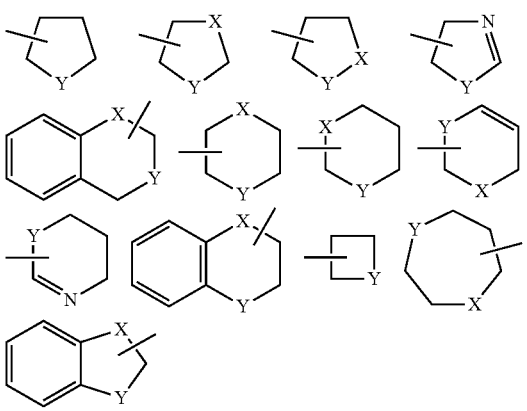

wherein each X is selected from $CR^{58}_2$, $NR^{58}$, O and S; and each Y is selected from $NR^{58}$, O and S; and $R^{58}$ is independently hydrogen, alkyl, cycloalkyl, cycloheteroalkyl, aryl, heteroaryl, heteroalkyl or the like. These cycloheteroalkyl rings may be optionally substituted with one or more groups selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, keto, nitro, thioalkoxy, substituted thioalkoxy, thioaryloxy, thioketo, thiol, alkyl-S(O)—, aryl-S(O)—, alkyl-S(O)$_2$— and aryl-S(O)$_2$—. Substituting groups include carbonyl or thiocarbonyl which provide, for example, lactam and urea derivatives.

Examples of representative cycloheteroalkenyls include the following:

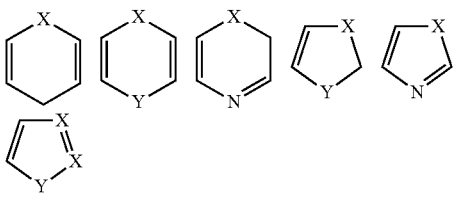

wherein each X is selected from $CR^{58}_2$, $NR^{58}$, O and S; and each Y is selected from carbonyl, N, $NR^{58}$, O and S; and $R^{58}$ is independently hydrogen, alkyl, cycloalkyl, cycloheteroalkyl, aryl, heteroaryl, heteroalkyl or the like.

Examples of representative aryl having hetero atoms containing substitution include the following:

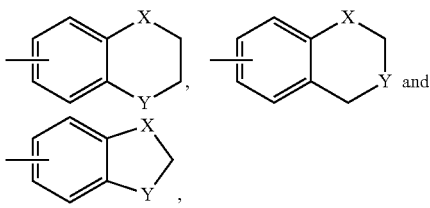

wherein each X is selected from C—$R^{58}_2$ $NR^{58}$, O and S; and each Y is selected from carbonyl, $NR^{58}$, O and S; and $R^{58}$ is independently hydrogen, alkyl, cycloalkyl, cycloheteroalkyl, aryl, heteroaryl, heteroalkyl or the like.

"Hetero substituent" refers to a halo, O, S or N atom-containing functionality that may be present as an $R^4$ in a $R^{4c}$ group present as substituents directly on W, W', X, X', Y or Z of the compounds provided herein or may be present as a substituent in the "substituted" aryl and aliphatic groups present in the compounds.

Examples of hetero substituents include:
-halo,
—$NO_2$, —$NH_2$, —$NHR^{59}$, —$N(R^{59})_2$,
—NRCOR, —$NR^{59}SOR^{59}$, —$NR^{59}SO_2R^{59}$, OH, CN,
—$CO_2H$,
—$R^{59}$—OH, —O—$R^{59}$, —$COOR^{59}$,
—$CON(R^{59})_2$, —$CONROR^{59}$,
—$SO_3H$, —$R^{59}$—S, —$SO_2N(R^{59})_2$,
—$S(O)R^{59}$, —$S(O)_2R^{59}$ wherein each $R^{59}$ is independently an aryl or aliphatic, optionally with substitution. Among hetero substituents containing $R^{59}$ groups, preference is given to those materials having aryl and alkyl $R^{59}$ groups as defined herein. Preferred hetero substituents are those listed above.

"Hydrogen bond donor" group refers to a group containing O—H, or N—H functionality. Examples of "hydrogen bond donor" groups include —OH, —$NH_2$, and —NH—$R^{59a}$ and wherein $R^{59a}$ is alkyl, acyl, cycloalkyl, aryl, or heteroaryl.

"Dihydroxyphosphoryl" refers to the radical —$PO(OH)_2$.

"Substituted dihydroxyphosphoryl" refers to those groups recited in the definition of "substituted" herein, and particularly refers to a dihydroxyphosphoryl radical wherein one or both of the hydroxyl groups are substituted. Suitable substituents are described in detail below.

"Aminohydroxyphosphoryl" refers to the radical —PO(OH)$NH_2$.

"Substituted aminohydroxyphosphoryl" refers to those groups recited in the definition of "substituted" herein, and particularly refers to an aminohydroxyphosphoryl wherein the amino group is substituted with one or two substituents. Suitable substituents are described in detail below. In certain embodiments, the hydroxyl group can also be substituted.

"Thioalkoxy" refers to the group —$SR^{60}$ where $R^{60}$ is alkyl.

"Substituted thioalkoxy" refers to those groups recited in the definition of "substituted" herein, and particularly refers to a thioalkoxy group having 1 or more substituents, for instance from 1 to 5 substituents, and particularly from 1 to 3 substituents, selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, keto, nitro, thioalkoxy, substituted thioalkoxy, thioaryloxy, thioketo, thiol, alkyl-S(O)—, aryl-S(O)—, alkyl-S(O)$_2$— and aryl-S(O)$_2$—.

"Sulfanyl" refers to the radical HS—. "Substituted sulfanyl" refers to a radical such as RS— wherein R is any substituent described herein.

"Sulfonyl" refers to the divalent radical —$S(O_2)$—. "Substituted sulfonyl" refers to a radical such as $R^{61}$—$(O_2)S$— wherein $R^{61}$ is any substituent described herein. "Atninosulfonyl" or "Sulfonamide" refers to the radical $H_2N(O_2)S$—, and "substituted aminosulfonyl" "substituted sulfonamide" refers to a radical such as $R^{62}_2N(O_2)S$— wherein each $R^{62}$ is independently any substituent described herein.

"Sulfone" refers to the group —$SO_2R^{63}$. In particular embodiments, $R^{63}$ is selected from H, lower alkyl, alkyl, aryl and heteroaryl.

"Thioaryloxy" refers to the group —$SR^{64}$ where $R^{64}$ is aryl.

"Thioketo" refers to the group =S.

"Thiol" refers to the group —SH.

One having ordinary skill in the art of organic synthesis will recognize that the maximum number of heteroatoms in a stable, chemically feasible heterocyclic ring, whether it is aromatic or non aromatic, is determined by the size of the ring, the degree of unsaturation and the valence of the heteroatoms. In general, a heterocyclic ring may have one to four heteroatoms so long as the heteroaromatic ring is chemically feasible and stable.

"Pharmaceutically acceptable salt" refers to a salt of a compound provided herein that is pharmaceutically acceptable and that possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, N-methylglucamine and the like. Salts further include, by way of example only, sodium, potassium, calcium, magnesium, ammonium, tetraalkylammonium, and the like; and when the compound contains a basic functionality, salts of non toxic organic or inorganic acids, such as hydrochloride, hydrobromide, tartrate, mesylate, acetate, maleate, oxalate and the like. The term "pharmaceutically acceptable cation" refers to a non toxic, acceptable cationic counter-ion of an acidic functional group. Such cations are exemplified by sodium, potassium, calcium, magnesium, ammonium, tetraalkylammonium cations, and the like.

"Pharmaceutically acceptable vehicle" refers to a diluent, adjuvant, excipient or carrier with which a compound provided herein is administered.

"Prodrugs" refers to molecules, including derivatives of the compounds provided herein, which have cleavable groups and become by solvolysis or under physiological conditions the compounds provided herein which are pharmaceutically active in vivo. Such examples include, but are not limited to, choline ester derivatives and the like, N-alkylmorpholine esters and the like.

"Solvate" refers to forms of the compound that are associated with a solvent, usually by a solvolysis reaction. Conventional solvents include water, ethanol, acetic acid and the like. The compounds provided herein may be prepared e.g. in crystalline form and may be solvated or hydrated. Suitable solvates include pharmaceutically acceptable solvates, such as hydrates, and further include both stoichiometric solvates and non-stoichiometric solvates.

"Subject" refers to humans and non-human mammals. In certain embodiments, a subject is a human.

"Therapeutically effective amount" means the amount of a compound that, when administered to a subject for treating a disease, is sufficient to effect such treatment for the disease. The "therapeutically effective amount" can vary depending on the compound, the disease and its severity, and the age, weight, etc., of the subject to be treated.

Other derivatives of the compounds provided herein can have activity in both their acid and acid derivative forms, but in the acid sensitive form often offers advantages of solubility, tissue compatibility, or delayed release in the mammalian organism (see, Bundgard, H., Design of Prodrugs, pp. 7-9, 21-24, Elsevier, Amsterdam 1985). Prodrugs include acid derivatives well know to practitioners of the art, such as, for example, esters prepared by reaction of the parent acid with a suitable alcohol, or amides prepared by reaction of the parent acid compound with a substituted or unsubstituted amine, or acid anhydrides, or mixed anhydrides. Simple aliphatic or aromatic esters, amides and anhydrides derived from acidic groups pendant on the compounds provided herein are preferred prodrugs. In some cases it is desirable to prepare double ester type prodrugs such as (acyloxy)alkyl esters or ((alkoxycarbonyl)oxy)alkylesters. Preferred are the $C_1$ to $C_8$ alkyl, $C_2$-$C_8$ alkenyl, aryl, $C_7$-$C_{12}$ substituted aryl, and $C_7$-$C_{12}$ arylalkyl esters of the compounds provided herein.

As used herein, the term "isotopic variant" refers to a compound that comprises an unnatural proportion of an isotope of one or more of the atoms that constitute such compound. For example, an "isotopic variant" of a compound can comprise an unnatural proportion of one or more non-radioactive isotopes, such as for example, deuterium ($^2H$ or D), carbon-13 ($^{13}C$), nitrogen-15 ($^{15}N$), or the like. It will be understood that, in a compound comprising an unnatural proportion of an isotope, any example of an atom where present, may vary in isotope composition. For example, any hydrogen may be $^2H/D$, or any carbon may be $^{13}C$, or any nitrogen may be $^{15}N$, and that the presence and placement of such atoms may be determined within the skill of the art. Likewise, provided herein are methods for preparation of isotopic variants with radioisotopes, in the instance for example, where the resulting compounds may be used for drug and/or substrate tissue distribution studies. The radioactive isotopes tritium, i.e. $^3H$, and carbon-14, i.e. $^{14}C$, are particularly useful for this purpose in view of their ease of incorporation and ready means of detection. Further, compounds may be prepared that are substituted with positron emitting isotopes, such as $^{11}C$, $^{18}F$, $^{15}O$ and $^{13}N$, and would be useful in Positron Emission Topography (PET) studies for examining substrate receptor occupancy. All isotopic variants of the compounds provided herein, radioactive or not, are intended to be encompassed within the scope provided herein.

It is also to be understood that compounds that have the same molecular formula but differ in the nature or sequence of bonding of their atoms or the arrangement of their atoms in space are termed "isomers". Isomers that differ in the arrangement of their atoms in space are termed "stereoisomers".

Stereoisomers that are not mirror images of one another are termed "diastereomers" and those that are non-superimposable mirror images of each other are termed "enantiomers". When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

As used herein a pure enantiomeric compound is substantially free from other enantiomers or stereoisomers of the compound (i.e., in enantiomeric excess). In other words, an "S" form of the compound is substantially free from the "R" form of the compound and is, thus, in enantiomeric excess of the "R" form. The term "enantiomerically pure" or "pure enantiomer" denotes that the compound comprises more than 75% by weight, more than 80% by weight, more than 85% by weight, more than 90% by weight, more than 91% by weight, more than 92% by weight, more than 93% by weight, more than 94% by weight, more than 95% by weight, more than 96% by weight, more than 97% by weight, more than 98% by weight, more than 98.5% by weight, more than 99% by weight, more than 99.2% by weight, more than 99.5% by weight, more than 99.6% by weight, more than 99.7% by weight, more than 99.8% by weight or more than 99.9% by weight, of the enantiomer. In certain embodiments, the weights are based upon total weight of all enantiomers or stereoisomers of the compound.

As used herein and unless otherwise indicated, the term "enantiomerically pure R-compound" refers to at least about 80% by weight R-compound and at most about 20% by weight S-compound, at least about 90% by weight R-compound and at most about 10% by weight S-compound, at least about 95% by weight R-compound and at most about 5% by weight S-compound, at least about 99% by weight R-compound and at most about 1% by weight S-compound, at least about 99.9% by weight R-compound or at most about 0.1% by weight S-compound. In certain embodiments, the weights are based upon total weight of compound.

As used herein and unless otherwise indicated, the term "enantiomerically pure S-compound" or "S-compound" refers to at least about 80% by weight S-compound and at most about 20% by weight R-compound, at least about 90% by weight S-compound and at most about 10% by weight R-compound, at least about 95% by weight S-compound and at most about 5% by weight R-compound, at least about 99% by weight S-compound and at most about 1% by weight R-compound or at least about 99.9% by weight S-compound and at most about 0.1% by weight R-compound. In certain embodiments, the weights are based upon total weight of compound.

In the compositions provided herein, an enantiomerically pure compound or a pharmaceutically acceptable salt, solvate, hydrate or prodrug thereof can be present with other active or inactive ingredients. For example, a pharmaceutical composition comprising enantiomerically pure R-compound can comprise, for example, about 90% excipient and about 10% enantiomerically pure R-compound. In certain embodiments, the enantiomerically pure R-compound in such compositions can, for example, comprise, at least about 95% by weight R-compound and at most about 5% by weight S-compound, by total weight of the compound. For example, a pharmaceutical composition comprising enantiomerically pure S-compound can comprise, for example, about 90% excipient and about 10% enantiomerically pure S-compound. In certain embodiments, the enantiomerically pure S-compound in such compositions can, for example, comprise, at least about 95% by weight S-compound and at most about 5% by weight R-compound, by total weight of the compound. In certain embodiments, the active ingredient can be formulated with little or no excipient or carrier.

"Tautomers" refer to compounds that are interchangeable forms of a particular compound structure, and that vary in the displacement of hydrogen atoms and electrons. Thus, two structures may be in equilibrium through the movement of it electrons and an atom (usually H). For example, enols and ketones are tautomers because they are rapidly interconverted by treatment with either acid or base. Another example of tautomerism is the aci- and nitro-forms of phenylnitromethane, that are likewise formed by treatment with acid or base.

Tautomeric forms may be relevant to the attainment of the optimal chemical reactivity and biological activity of a compound of interest.

The compounds provided herein may possess one or more asymmetric centers; such compounds can therefore be produced as individual (R)- or (S)-stereoisomers or as mixtures thereof. Unless indicated otherwise, the description or naming of a particular compound in the specification and claims is intended to include both individual enantiomers and mixtures, racemic or otherwise, thereof. The methods for the determination of stereochemistry and the separation of stereoisomers are well-known in the art Compounds As set forth earlier herein, the compounds of the present invention are useful for preventing and/or treating a broad range of conditions, among them, arthritis, Parkinson's disease, Alzheimer's disease, stroke, uveitis, asthma, myocardial infarction, the treatment and prophylaxis of pain syndromes (acute and chronic or neuropathic), traumatic brain injury, acute spinal cord injury, neurodegenerative disorders, alopecia (hair loss), inflammatory bowel disease and autoimmune disorders or conditions in mammals.

In order that the invention described herein may be more fully understood, the following structures representing compounds typical of the invention are set forth. It should be understood that these examples are for illustrative purposes only and are not to be construed as limiting this invention in any manner.

Accordingly, in a first aspect of the invention, compounds are disclosed that are capable of modifying ion channels, in vivo, having a formula I:

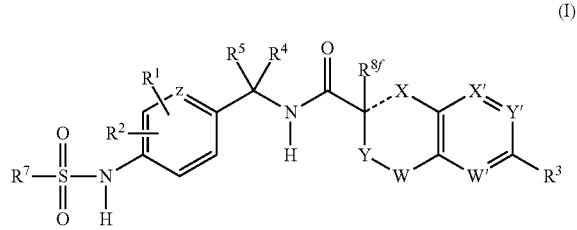

(I)

or a pharmaceutically acceptable salt thereof, and isotopic variants thereof, stereoisomers and tautomers thereof, wherein:

W represents O, $CR^{8a}R^{8b}$, or $NR^{8c}$;

X represents N, O, $CR^{8a}$, $CR^{8a}R^{8b}$, or $NR^{8c}$;

Y represents $CR^{8d}R^{8e}$;

W', X', Y' and Z each independently represent $CR^{8}$ or N; provided that W', X' and Y' are not all N at the same time;

$R^1$ and $R^2$ each independently represent hydrogen, halogen, hydroxy, substituted or unsubstituted alkyl, substituted or unsubstituted alkoxy, alkylthio, alkylsulfinyl or alkylsulfonyl;

$R^3$ represents hydrogen, halogen, hydroxy, substituted or unsubstituted alkyl, substituted or unsubstituted alkoxy, acyl, substituted or unsubstituted amino, substituted or unsubstituted alkylamino, substituted or unsubstituted dialkylamino, substituted or unsubstituted cycloalkyl, substituted or unsubstituted heterocycloalkyl, or substituted or unsubstituted heteroaryl;

$R^4$ and $R^5$ each independently represent hydrogen or substituted or unsubstituted alkyl;

$R^7$ represents $(C_1-C_6)$alkyl;

each $R^8$ independently represents hydrogen, halogen, hydroxy, substituted or unsubstituted alkyl, substituted or unsubstituted alkoxy, acyl, substituted or unsubstituted amino, substituted or unsubstituted alkylamino, substituted or unsubstituted dialkylamino, substituted or unsubstituted cycloalkyl, substituted or unsubstituted heterocycloalkyl, substituted or unsubstituted aryl, substituted or unsubstituted heteroaryl, alkylthio, alkylsulfinyl or alkylsulfonyl;

each $R^{8a}$, $R^{8b}$, $R^{8d}$, $R^{8e}$ and $R^{8f}$ independently represents hydrogen, halo, hydroxy, or substituted or unsubstituted alkyl; provided that when the dotted bond is a double bond $R^{8f}$ is absent;

$R^{8c}$ represents hydrogen, or substituted or unsubstituted alkyl; and the dotted bond represents a single or a double bond;

provided that i) when W and X both are O, and Y' is $CR^8$; then at least one of $R^3$ and $R^8$ is other than H; and ii) when W and X both are $CH_2$, W' is N, and Y' is $CR^8$; then at least one of $R^3$ and $R^8$ is other than H.

In one particular embodiment, with respect to compounds of formula I, W', X', Y' and Z each independently represent $CR^8$.

In another particular embodiment, with respect to compounds of formula I, one of W', X', Y' and Z represent N and the rest each independently represent $CR^8$.

In another particular embodiment, with respect to compounds of formula I, two of W', X', Y' and Z represent N and the rest each independently represent $CR^8$.

In another particular embodiment, with respect to compounds of formula I, W and X each independently represent $CR^{8a}R^{8b}$; and the dotted bond is a single bond.

In another particular embodiment, with respect to compounds of formula I, W and X each independently represent $CH_2$; and the dotted bond is a single bond.

In another particular embodiment, with respect to compounds of formula I, W represents $CR^{8a}R^{8b}$; X represents $CR^{8a}$; and the dotted bond is a double bond.

In another particular embodiment, with respect to compounds of formula I, W represents $CH_2$; X represents CH; and the dotted bond is a double bond.

In another particular embodiment, with respect to compounds of formula I, X represents $NR^{8c}$; and the dotted bond is a single bond.

In another particular embodiment, with respect to compounds of formula I, X represents O; and the dotted bond is a single bond.

In another particular embodiment, with respect to compounds of formula I, W represents $CR^{8a}R^{8b}$.

In another particular embodiment, with respect to compounds of formula I, wherein W represents $NR^{8e}$.

In another particular embodiment, with respect to compounds of formula I, wherein W represents O.

In another particular embodiment, with respect to compounds of formula I, Y represents $CR^{8d}R^{8e}$.

In another particular embodiment, with respect to compounds of formula I, Y represents $CH_2$.

In another particular embodiment, with respect to compounds of formula I, wherein Y represents $NR^{8c}$.

In another particular embodiment, with respect to compounds of formula I, wherein Y represents O.

In another embodiment, with respect to compounds of the invention, the compound is according to formula II

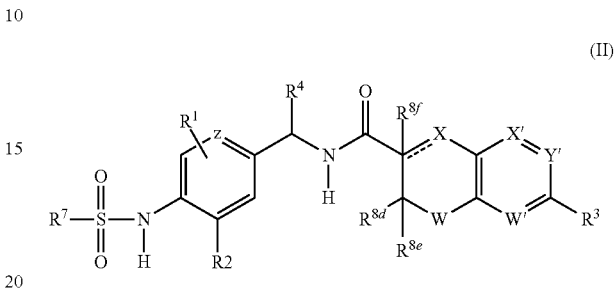

(II)

or a pharmaceutically acceptable salt, and isotopic variants thereof, stereoisomers and tautomers thereof, wherein W, W', X, X', Y', Z, and $R^7$ are as defined for formula I;

$R^1$ and $R^2$ each independently represent hydrogen, halogen, hydroxy, $(C_1-C_6)$alkyl, $(C_1-C_6)$alkoxy, hydroxy$(C_1-C_6)$alkoxy, $(C_1-C_6)$alkoxy-$(C_1-C_6)$alkyl, $(C_1-C_6)$alkoxy-$(C_1-C_6)$alkoxy, halo$(C_1-C_6)$alkyl, $(C_1-C_6)$allylthio, $(C_1-C_6)$alkylsulfinyl or $(C_1-C_6)$alkylsulfonyl;

$R^3$ represents hydrogen, halogen, hydroxy, $(C_1-C_6)$alkyl, halo$(C_1-C_6)$allyl, hydroxy$(C_1-C_6)$alkyl, halo hydroxy$(C_1-C_6)$allyl, $(C_1-C_6)$alkoxy, hydroxy$(C_1-C_6)$alkoxy, $(C_1-C_6)$alkoxy-$(C_1-C_6)$alkyl, $(C_1-C_6)$acyl, $(C_1-C_6)$alkoxy-$(C_1-C_6)$alkoxy, $[(C_1-C_6)$alkyl]NH—, $[(C_1-C_6)$alkyl]$_2$N—, [hydroxy$(C_1-C_6)$alkyl]NH—, substituted or unsubstituted 3-6 membered cycloalkyl, [3-6 membered cycloalkyl]oxy, or [3-6 membered heterocycloalkyl]oxy or 3-6 membered heterocycloalkyl, unsubstituted or substituted with halo, $(C_1-C_6)$alkyl, halo$(C_1-C_6)$alkyl, hydroxy$(C_1-C_6)$alkyl, $(C_1-C_6)$alkoxy, $[(C_1-C_6)$alkyl]$_2$N—, or hydroxy, or 3-6 membered heteroaryl, 3-6 membered cycloalkyl $(C_1-C_6)$alkyl, or 3-6 membered cycloalkyl hydroxy $(C_1-C_6)$alkyl;

$R^4$ represents hydrogen, $(C_1-C_6)$alkyl, halogen, halo$(C_1-C_6)$alkyl, or hydroxy$(C_1-C_6)$allyl;

each $R^8$ independently represents hydrogen, halogen, hydroxy, $(C_1-C_6)$alkyl, $(C_1-C_6)$alkoxy, hydroxy$(C_1-C_6)$alkoxy, $(C_1-C_6)$alkoxy-$(C_1-C_6)$allyl, $(C_1-C_6)$alkoxy-$(C_1-C_6)$alkoxy, halo$(C_1-C_6)$allyl, halo hydroxy$(C_1-C_6)$allyl, $(C_1-C_6)$alkylthio, $(C_1-C_6)$alkylsulfinyl, $[(C_1-C_6)$alkyl]NH—, $[(C_1-C_6)$cycloalkyl]NH—, $[(C_1-C_6)$alkyl]$_2$N—, [hydroxy$(C_1-C_6)$alkyl]NH—, [3-6 membered cycloalkyl]oxy, [3-6 membered heterocycloalkyl]oxy or 3-6 membered heterocycloalkyl, unsubstituted or substituted with halo, $(C_1-C_6)$alkyl, $(C_1-C_6)$alkoxy, halo$(C_1-C_6)$alkyl, hydroxy$(C_1-C_6)$allyl, aryl$(C_1-C_6)$alkyl, $[(C_1-C_6)$alkyl]$_2$N—, $(C_1-C_6)$carbalkoxy, hydroxy, aryl, $(C_1-C_6)$alkylaryl, halo$(C_1-C_6)$alkylaryl, haloaryl, $(C_1-C_6)$alkoxyaryl, or 3-10 membered heteroaryl, 3-6 membered cycloalkyl $(C_1-C_6)$alkyl, or 3-6 membered cycloalkyl hydroxy $(C_1-C_6)$alkyl or $(C_1-C_6)$alkylsulfonyl;

each $R^{8a}$, $R^{8b}$, $R^{8d}$, $R^{8e}$ and $R^{8f}$ independently represents hydrogen, halo, hydroxy, $(C_1-C_6)$alkyl, hydroxy$(C_1-C_6)$ alkyl, $(C_1-C_6)$alkoxy-$(C_1-C_6)$alkyl, or halo$(C_1-C_6)$alkyl; provided that when the dotted bond is a double bond $R^{8r}$ is absent;

$R^{8c}$ represents hydrogen, $(C_1-C_6)$alkyl, hydroxy$(C_1-C_6)$alkyl, $(C_1-C_6)$alkoxy-$(C_1-C_6)$alkyl, cycloalkyl, or halo$(C_1-C_6)$alkyl; and the dotted bond represents a single or a double bond In one particular embodiment, with respect to compounds of formula I or II, $R^4$ is hydrogen.

In another embodiment, with respect to compounds of formula I or II, $R^4$ is $(C_1-C_6)$alkyl.

In another embodiment, with respect to compounds of formula I or II, $R^4$ is methyl.

In another embodiment, with respect to compounds of formula I or II, $R^7$ is Me, Et, Pr, i-Pr, or t-butyl.

In another embodiment, with respect to compounds of formula I or II, $R^7$ is Me.

In another embodiment, with respect to compounds of formula I or II, $R^1$ represents hydrogen, halogen or $(C_1-C_6)$allyl.

In another embodiment, with respect to compounds of formula I or II, $R^1$ represents H or F.

In another embodiment, with respect to compounds of formula I or II, $R^2$ represents halogen, $(C_1-C_6)$alkyl, halo$(C_1-C_6)$allyl or hydroxy$(C_1-C_6)$alkyl.

In another embodiment, with respect to compounds of formula I or II, $R^2$ represents F or methyl.

In another embodiment, with respect to compounds of formula I or II, each of $R^1$ and $R^2$ represents F.

In another embodiment, with respect to compounds of formula I or II, Z represents CH, CF or CCl.

In another embodiment, with respect to compounds of formula I or II, Z represents N.

In another embodiment, with respect to compounds of formula I or II, $R^1$ represents H; $R^2$ represents Me and Z represents CF.

In another embodiment, with respect to compounds of formula I or II, W', X', and Y' each independently represent $CR^8$.

In another embodiment, with respect to compounds of formula I or II, W', X', and Y' each independently represent CH.

In another embodiment, with respect to compounds of formula I or II, one of W', X', and Y' represents N and the rest each independently represents $CR^8$.

In another embodiment, with respect to compounds of formula I or II, W' is N and each of X', and Y' is independently $CR^8$.

In another embodiment, with respect to compounds of formula I or II, W' is N and each of X', and Y' is independently CH.

In another embodiment, with respect to compounds of formula I or II, W' is N, Y' is CH, and X' is $CR^8$.

In another embodiment, with respect to compounds of formula I or II, W and X each independently represent $CR^{8a}R^{8b}$; and the dotted bond is a single bond.

In another embodiment, with respect to compounds of formula I or II, W represents $CR^{8a}R^{8b}$; X represents $CR^{8a}$; and the dotted bond is a double bond.

In another embodiment, with respect to compounds of formula I or II, W represents $CH_2$; X represents CH; and the dotted bond is a double bond.

In another embodiment, with respect to compounds of formula I or II, X represents $NR^{8c}$; and the dotted bond is a single bond.

In another embodiment, with respect to compounds of formula I or II, X represents O; and the dotted bond is a single bond.

In another embodiment, with respect to compounds of formula I or II, W represents $CR^{8a}R^{8b}$.

In another embodiment, with respect to compounds of formula I or II, W represents $CH_2$.

In another embodiment, with respect to compounds of formula I or II, W represents $NR^{8c}$.

In another embodiment, with respect to compounds of formula I or II, W represents O.

In another embodiment, with respect to compounds of formula I or II, W represents $NR^{8c}$ and $R^{8c}$ represents H or Me.

In another embodiment, with respect to compounds of formula I or II, Y represents $CH_2$.

In another embodiment, with respect to compounds of formula I or II, Y represents $NR^{8e}$.

In another embodiment, with respect to compounds of formula I or II, Y represents O.

In another embodiment, with respect to compounds of formula I or II, Y represents $NR^{8e}$ and $R^{8c}$ represents H or Me.

In another embodiment, with respect to compounds of formula II, each $R^{8d}$ and $R^{8e}$ represents H.

In another embodiment, with respect to compounds of formula II, one of $R^{8d}$ and $R^{8e}$ represents Me and the other is H.

In another embodiment, with respect to compounds of formula II, each $R^{8d}$ and $R^{8e}$ represents Me.

In another embodiment, with respect to compounds of formula II, $R^{8f}$ represents H.

In another embodiment, with respect to compounds of formula II, $R^{8f}$ represents Me.

In another embodiment, with respect to compounds of formula I or II, W', X', and Y' each independently represent CH and $R^3$ represents OMe, OEt, COMe, $NMe_2$, or $NEt_2$.

In another particular embodiment, with respect to compounds of formula I or II, the dotted bond is a single bond and X is $CH_2$ or NMe. In yet another particular embodiment, X is O.

In another particular embodiment, with respect to compounds of formula I or II, the dotted bond is a double bond and X is CH or N.

In another particular embodiment, with respect to compounds of formula I or II, W is $CH_2$ or NMe. In yet another particular embodiment, W is O.

In a yet another particular embodiment, with respect to compounds of formula I or II, the dotted bond is a single bond and each of W and X is O.

In a yet another particular embodiment, with respect to compounds of formula I or II, the dotted bond is a single bond; each of W and X is $CH_2$; and Y is NMe or O.

In another embodiment, with respect to compounds of formula I or II, $R^3$ is F, Br, or Cl.

In another embodiment, with respect to compounds of formula I or II, $R^3$ is Me, i-Pr, t-Bu, OMe, 1-methyl-1-trifluoromethylethyl, or 1-methyl-1-hydroxyethyl.

In another embodiment, with respect to compounds of formula I or II, $R^3$ is $CF_3$.

In another embodiment, with respect to compounds of formula I or II, $R^3$ is 3-6 membered cycloalkyl.

In another embodiment, with respect to compounds of formula I or II, $R^3$ is cyclopropyl, 1-methylcyclopropyl, 1-hydroxycyclopropyl, 1-trifluoromethylcyclopropyl, cyclobutyl or cyclopentyl.

In another embodiment, with respect to compounds of formula I or II, $R^3$ is 3-6 membered heterocycloalkyl.

In another embodiment, with respect to compounds of formula I or II, R³ is

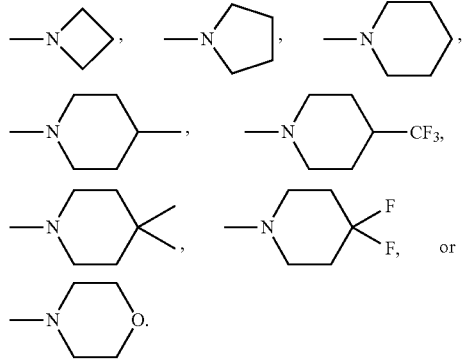

In another embodiment, with respect to compounds of formula I or II, R³ is —C(OMe)(Me)CF₃, —C(OH)(Me)CF₃, —C(Me)₂OH or —C(Me)(OH)-cyclopropyl.

In one embodiment, with respect to compounds of formula I, the compound is according to formula IIa, IIb, IIc, IId, IIe, IIf, IIg, IIh or IIi:

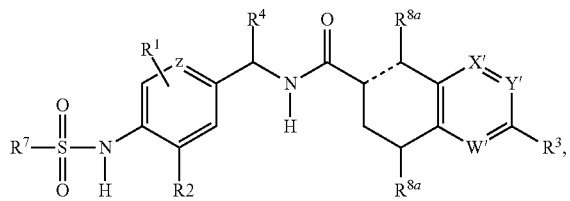
IIa

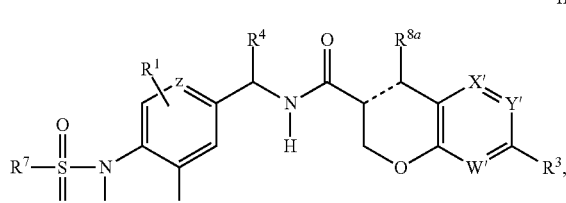
IIb

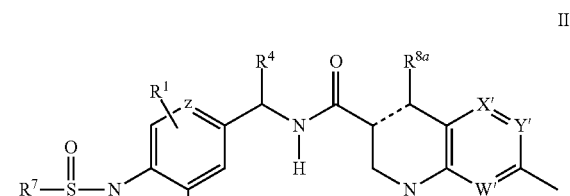
IIc

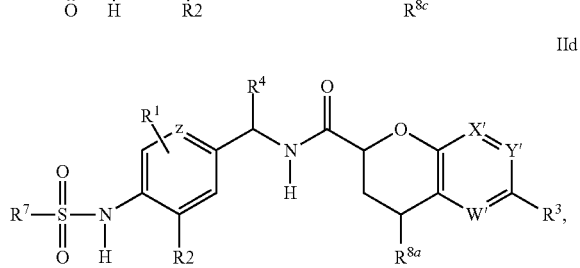
IId

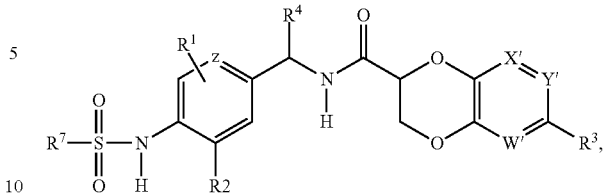
IIe

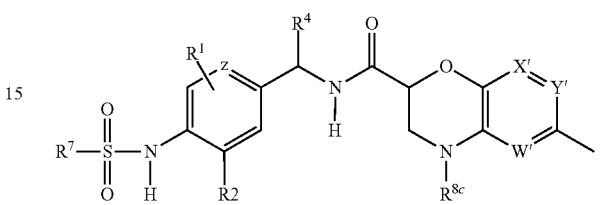
IIf

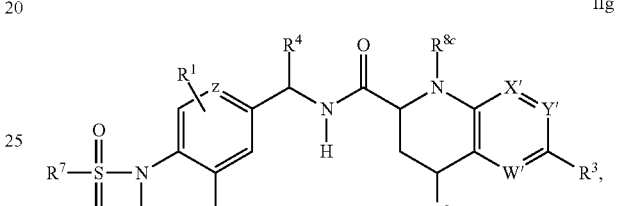
IIg

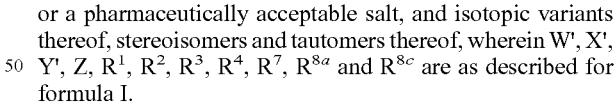
IIh

IIi or a pharmaceutically acceptable salt, and isotopic variants thereof, stereoisomers and tautomers thereof, wherein W', X', Y', Z, R¹, R², R³, R⁴, R⁷, R⁸ᵃ and R⁸ᶜ are as described for formula I.

In one embodiment, with respect to compounds of formulae I-IIi, R¹ represents hydrogen, halogen or (C₁-C₆)alkyl.

In another embodiment, with respect to compounds of formulae I-IIi, R¹ represents H or F.

In one embodiment, with respect to compounds of formulae I-IIi, the compound is according to formula IIa, IIb or IIc and the dotted bond is a single bond.

In another embodiment, with respect to compounds of formulae I-IIi, the compound is according to formula IIa, IIb or IIe and the dotted bond is a double bond.

In one embodiment, with respect to compounds of formulae I-IIi, W', X', and Y' each independently represent CR⁸.

In another embodiment, with respect to compounds of formulae I-IIi, W', X', and Y' each independently represent CH.

In another embodiment, with respect to compounds of formulae I-IIi, one of W', X', and Y' represents N and the rest each independently represents $CR^8$.

In another embodiment, with respect to compounds of formulae I-IIi, W' is N and each of X', and Y' is independently $CR^8$.

In another embodiment, with respect to compounds of formulae I-IIi, W' is N and each of X', and Y' is independently CH.

In one embodiment, with respect to compounds of formulae I-IIc, $R^{8a}$ is H or Me.

In another embodiment, with respect to compounds of formula I, the compound is according to formulae IIIa, IIIb, IIIc, IIId, IIIe, IIIf, IIIg, IIIh or IIIi:

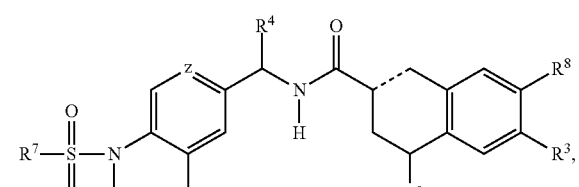

IIIa

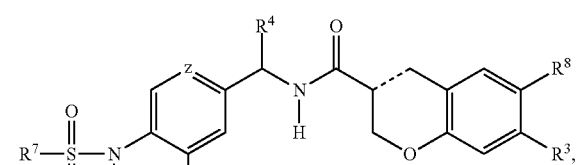

IIIb

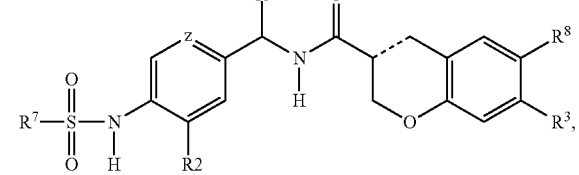

IIIc

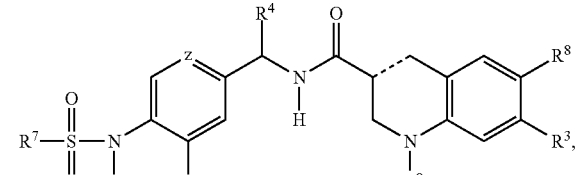

IIId

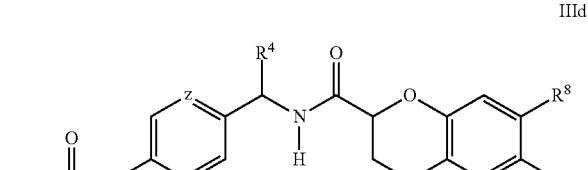

IIIe

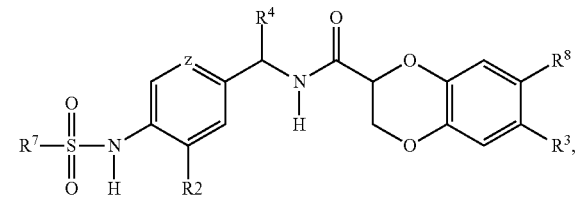

IIIf

IIIG

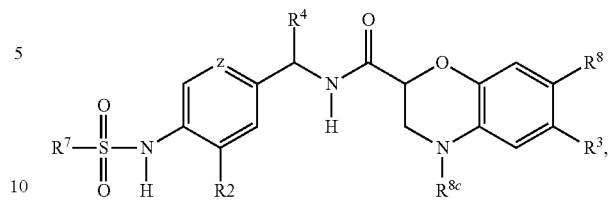

IIIh

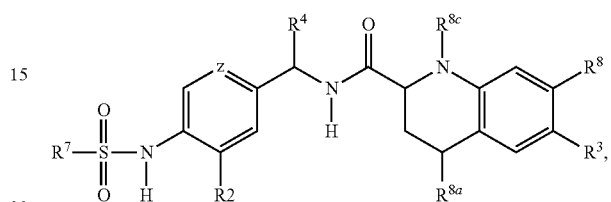

IIIi

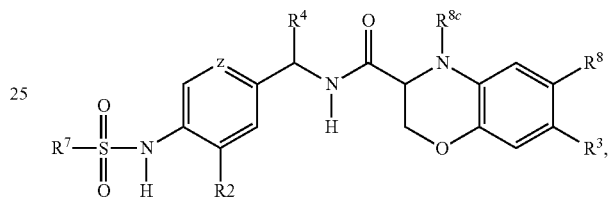

or a pharmaceutically acceptable salt, and isotopic variants thereof, stereoisomers and tautomers thereof, wherein Z, $R^2$, $R^3$, $R^4$, $R^7$, $R^8$, and $R^{8c}$ are as described for formula I.

In another embodiment, with respect to compounds of formula I, the compound is according to formulae IVa, IVb, IVc, IVd, We, IVf, IVg, IVh or IVi:

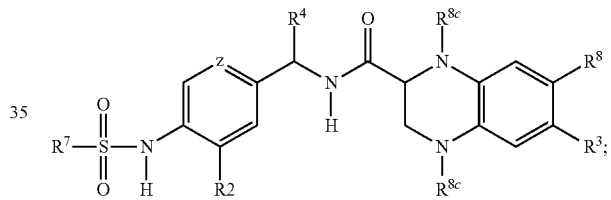

IVa

IVb

-continued
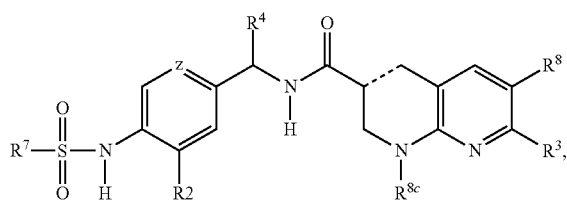
IVc
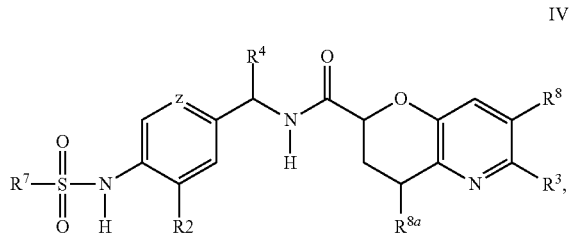
IVd
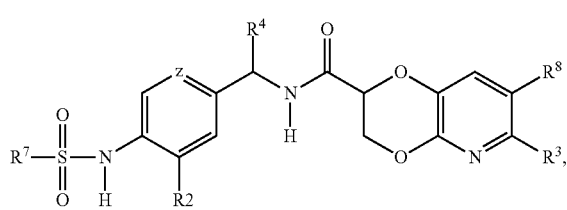
IVe
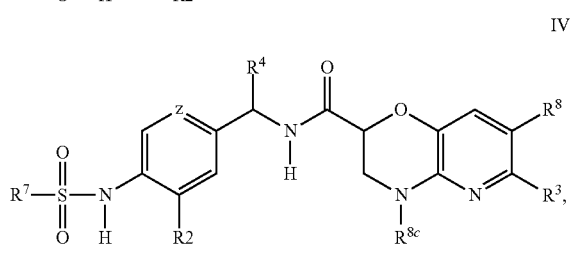
IVf
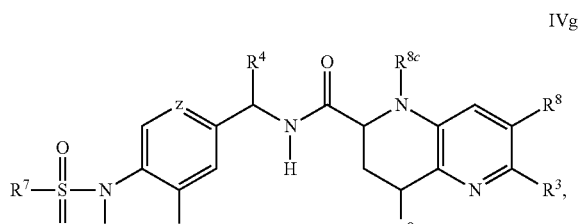
IVg
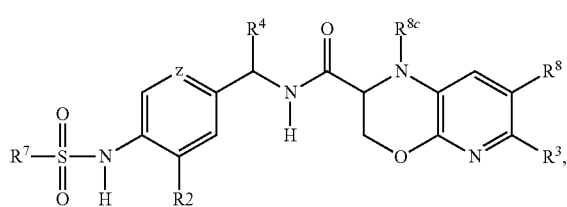
IVh
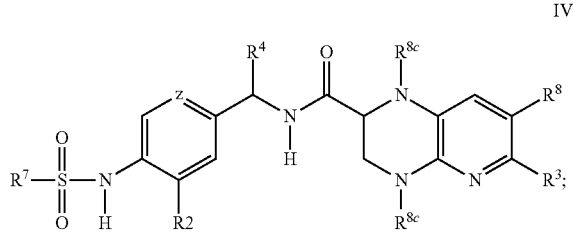
IVi
or a pharmaceutically acceptable salt, and isotopic variants thereof, stereoisomers and tautomers thereof, wherein Z, $R^2$, $R^3$, $R^4$, $R^7$, $R^8$, and Rbc are as described for formula I.
In another embodiment, with respect to compounds of formula I, the compound is according to formulae Va, Vb, Vc, Vd, Ve, Vf, Vg, Vh or Vi:
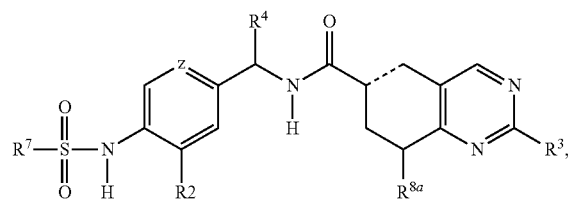
Va
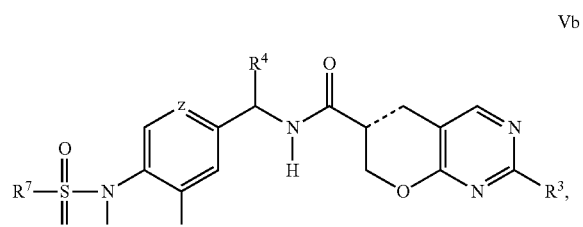
Vb
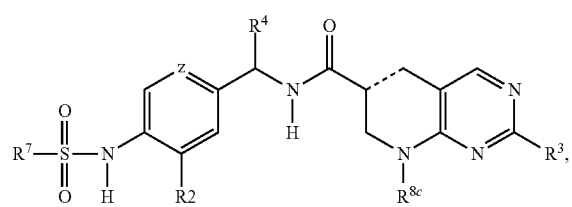
Vc
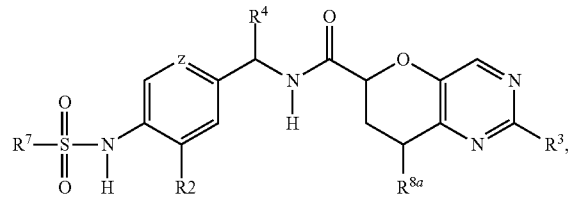
Vd
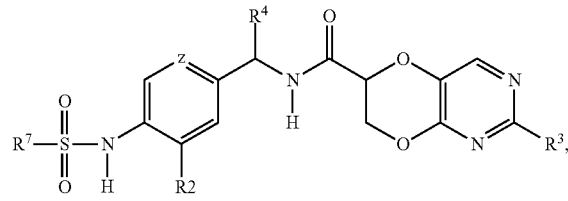
Ve
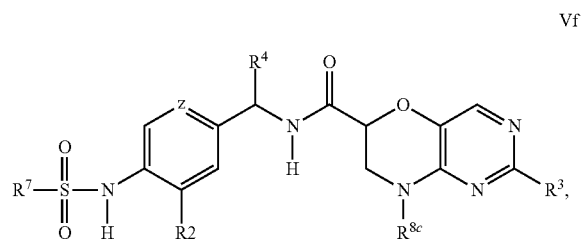
Vf

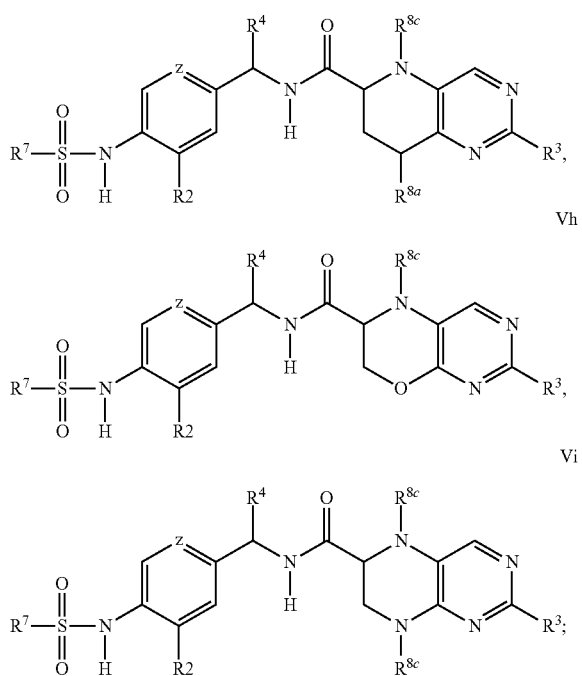

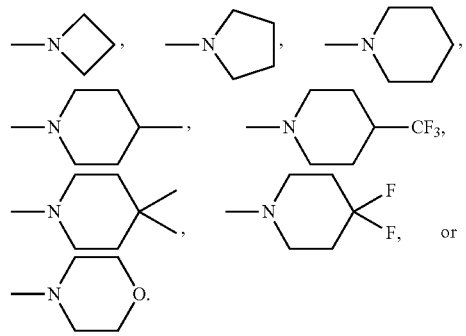

or a pharmaceutically acceptable salt, and isotopic variants thereof, stereoisomers and tautomers thereof, wherein Z, $R^2$, $R^3$, $R^4$, $R^7$, and $R^{8c}$ are as described for formula I.

In one embodiment, with respect to compounds of formulae Z represents CH, CF or CCl.

In another embodiment, with respect to compounds of formulae I-Vi, Z represents N.

In one embodiment, with respect to compounds of formulae I-Vi, $R^2$ represents halogen, $(C_1$-$C_6)$alkyl, halo$(C_1$-$C_6)$alkyl or hydroxy$(C_1$-$C_6)$alkyl.

In another embodiment, with respect to compounds of formulae I-Vi, $R^2$ represents F or methyl.

In another embodiment, with respect to compounds of formulae I-Vi, $R^2$ represents Me and Z represents CF.

In one embodiment, with respect to compounds of formulae IIa-IIc, IIIa-IIIc, IVa-IVc, and Va-Vc, the dotted bond is a single bond.

In another embodiment, with respect to compounds of formulae IIa-IIc, IIIa-IIIc, IVa-IVc, and Va-Vc, the dotted bond is a double bond.

In one embodiment, with respect to compounds of formulae I-Vi, $R^3$ or $R^8$ is H.

In another embodiment, with respect to compounds of formulae I-Vi, $R^3$ or $R^8$ independently represents OMe, OEt, COMe, $NMe_2$, or $NEt_2$.

In another embodiment, with respect to compounds of formulae I-Vi, $R^3$ or $R^8$ is independently F, Br, or Cl.

In another embodiment, with respect to compounds of formulae I-Vi, $R^3$ or $R^8$ is independently Me, i-Pr, t-Bu, 1-methyl-1-trifluoromethylethyl, or 1-methyl-1-hydroxyethyl.

In another embodiment, with respect to compounds of formulae I-Vi, $R^3$ or $R^8$ is independently $CF_3$.

In another embodiment, with respect to compounds of formulae I-Vi, $R^3$ or $R^8$ is independently 3-6 membered cycloalkyl.

In another embodiment, with respect to compounds of formulae I-Vi, $R^3$ or $R^8$ is independently cyclopropyl, 1-methylcyclopropyl, 1-hydroxycyclopropyl, 1-trifluoromethylcyclopropyl, cyclobutyl or cyclopentyl.

In another embodiment, with respect to compounds of formulae I-Vi, $R^3$ or $R^8$ is independently 3-6 membered heterocycloalkyl.

In another embodiment, with respect to compounds of formulae I-Vi, $R^3$ or $R^8$ is independently In another embodiment, with respect to compounds of formulae I-Vi, $R^3$ or $R^8$ is independently —C(OMe)(Me)$CF_3$, —C(OH)(Me)$CF_3$, —C(Me)$_2$OH or —C(Me)(OH)-cyclopropyl.

In one embodiment, with respect to compounds of formulae I-Vi, $R^4$ is hydrogen.

In another embodiment, with respect to compounds of formulae I-Vi, $R^4$ is $(C_1$-$C_6)$alkyl.

In another embodiment, with respect to compounds of formulae I-Vi, $R^4$ is methyl.

In one embodiment, with respect to compounds of formulae I-Vi, $R^7$ is alkyl.

In another embodiment, with respect to compounds of formulae I-Vi, $R^7$ is Me, Et, Pr, i-Pr, or t-butyl.

In another embodiment, with respect to compounds of formulae I-Vi, $R^{8c}$ is H or Me.

In another embodiment, with respect to compounds of formula I, the compound is selected from:
  6-tert-Butyl-chroman-2-carboxylic acid 3-fluoro-4-methanesulfonylamino-benzylamide;
  2H-Chromene-3-carboxylic acid [(R)-1-(2-fluoro-4-methanesulfonylamino-5-methyl-phenyl)-ethyl]-amide;
  Chroman-2-carboxylic acid [(R)-1-(2-fluoro-4-methanesulfonylamino-5-methyl-phenyl)-ethyl]-amide;
  1,2,3,4-Tetrahydro-naphthalene-2-carboxylic acid [(R)-1-(2-fluoro-4-methanesulfonylamino-5-methyl-phenyl)-ethyl]-amide;
  6-Chloro-2H-chromene-3-carboxylic acid [(R)-1-(2-fluoro-4-methanesulfonylamino-5-methyl-phenyl)-ethyl]-amide;
  6-Methoxy-1-methyl-1,2,3,4-tetrahydro-naphthalene-2-carboxylic acid [(R)-1-(2-fluoro-4-methanesulfonylamino-5-methyl-phenyl)-ethyl]-amide;
  6-Chloro-chroman-3-carboxylic acid [(R)-1-(2-fluoro-4-methanesulfonylamino-5-methyl-phenyl)-ethyl]-amide;
  4-Methyl-6-trifluoromethyl-3,4-dihydro-2H-benzo[1,4]oxazine-2-carboxylic acid [(R)-1-(2-fluoro-4-methanesulfonylamino-5-methyl-phenyl)-ethy]-amide;
  2-(2,2,2-Trifluoro-1,1-dimethyl-ethyl)-5,6,7,8-tetrahydro-quinoline-6-carboxylic acid [(R)-1-(2-fluoro-4-methanesulfonylamino-5-methyl-phenyl)-ethyl]-amide;

2-(2,2,2-Trifluoro-1,1-dimethyl-ethyl)-5,6,7,8-tetrahydro-quinoline-6-carboxylic acid [(R)-1-(2-fluoro-4-methanesulfonylamino-5-methyl-phenyl)-ethyl]-amide;

2-(2,2,2-Trifluoro-1,1-dimethyl-ethyl)-5,6,7,8-tetrahydro-quinoline-6-carboxylic acid [(R)-1-(2-fluoro-4-methanesulfonylamino-5-methyl-phenyl)-ethyl]-amide;

(R)-2,3-Dihydro-benzo[1,4]dioxine-2-carboxylic acid [(R)-1-(2-fluoro-4-methanesulfonylamino-5-methyl-phenyl)-ethyl]-amide;

(S)-2,3-Dihydro-benzo[1,4]dioxine-2-carboxylic acid [(R)-1-(2-fluoro-4-methanesulfonylamino-5-methyl-phenyl)-ethyl]-amide;

6-Methoxy-1,2,3,4-tetrahydro-naphthalene-2-carboxylic acid [1-(2-fluoro-4-methanesulfonylamino-5-methyl-phenyl)-ethyl]-amide;

(S)-5,6,7,8-Tetrahydro-quinoline-6-carboxylic acid [(R)-1-(2-fluoro-4-methanesulfonylamino-5-methyl-phenyl)-ethyl]-amide;

(R)-5,6,7,8-Tetrahydro-quinoline-6-carboxylic acid [(R)-1-(2-fluoro-4-methanesulfonylamino-5-methyl-phenyl)-ethyl]-amide;

2-(1-Hydroxy-1-methyl-ethyl)-5,6,7,8-tetrahydro-quinoline-6-carboxylic acid [(R)-1-(2-fluoro-4-methanesulfonylamino-5-methyl-phenyl)-ethyl]-amide;

(R)-2-(1-Methoxy-1-methyl-ethyl)-5,6,7,8-tetrahydro-quinoline-6-carboxylic acid [(R)-1-(2-fluoro-4-methanesulfonylamino-5-methyl-phenyl)-ethyl]-amide;

(S)-2-(1-Methoxy-1-methyl-ethyl)-5,6,7,8-tetrahydro-quinoline-6-carboxylic acid [(R)-1-(2-fluoro-4-methanesulfonylamino-5-methyl-phenyl)-ethyl]-amide;

(S)-6-Trifluoromethyl-2,3-dihydro-benzo[1,4]dioxine-2-carboxylic acid [(R)-1-(2-fluoro-4-methanesulfonylamino-5-methyl-phenyl)-ethyl]-amide;

(R)-7-Trifluoromethyl-2,3-dihydro-benzo[1,4]dioxine-2-carboxylic acid [(R)-1-(2-fluoro-4-methanesulfonylamino-5-methyl-phenyl)-ethyl]-amide;

(R)-6-Trifluoromethyl-2,3-dihydro-benzo[1,4]dioxine-2-carboxylic acid [(R)-1-(2-fluoro-4-methanesulfonylamino-5-methyl-phenyl)-ethyl]-amide;

(S)-7-Trifluoromethyl-2,3-dihydro-benzo[1,4]dioxine-2-carboxylic acid [(R)-1-(2-fluoro-4-methanesulfonylamino-5-methyl-phenyl)-ethyl]-amide;

(S)-2-(2-Methyl-[1,3]dioxolan-2-yl)-5,6,7,8-tetrahydro-quinoline-6-carboxylic acid [(R)-1-(2-fluoro-4-methanesulfonylamino-5-methyl-phenyl)-ethyl]-amide;

6-Trifluoromethyl-2,3-dihydro-[1,4]dioxino[2,3-b]pyridine-2-carboxylic acid [(R)-1-(2-fluoro-4-methanesulfonylamino-5-methyl-phenyl)-ethyl]-amide;

(R)-6-Trifluoromethyl-2,3-dihydro-benzo[1,4]dioxine-2-carboxylic acid [(R)-1-(3-fluoro-4-methanesulfonylamino-phenyl)-ethyl]-amide; and (R)-6-Trifluoromethyl-2,3-dihydro-benzo[1,4]dioxine-2-carboxylic acid [(R)-1-(3-chloro-4-methanesulfonylamino-phenyl)-ethyl]-amide;

or a pharmaceutically acceptable salt thereof, and isotopic variants thereof, stereoisomers and tautomers thereof.

In yet further particular embodiments, the compounds of the invention are set forth and may be selected from a comprehensive listing of such compounds, set forth later on herein in Table 1. The Table contains in excess of 15 compounds that have been or can be synthesized and have as a group, demonstrated activity in their capacity of modifying ion channels, in vivo, and thereby functioning in the therapeutic applications set forth herein in relation to capsaicin and the vanilloid receptor.

As discussed above, suitable compounds capable of modifying ion channels in vivo, may be selected from those listed in Table 1, below, and may be prepared either as shown or in the form of a pharmaceutically acceptable salt, solvate or prodrug thereof; and stereoisomers and tautomers thereof. All such variants are contemplated herein and are within the scope of the present invention.

In certain aspects, the present invention provides prodrugs and derivatives of the compounds according to the formulae above. Prodrugs are derivatives of the compounds of the invention, which have cleavable groups and become by solvolysis or under physiological conditions the compounds of the invention, which are pharmaceutically active, in vivo. Such examples include, but are not limited to, choline ester derivatives and the like, N-alkylmorpholine esters and the like.

Other derivatives of the compounds of this invention have activity in both their acid and acid derivative forms, but the acid sensitive form often offers advantages of solubility, tissue compatibility, or delayed release in the mammalian organism (see, Bundgard, H., Design of Prodrugs, pp. 7-9, 21-24, Elsevier, Amsterdam 1985). Prodrugs include acid derivatives well know to practitioners of the art, such as, for example, esters prepared by reaction of the parent acid with a suitable alcohol, or amides prepared by reaction of the parent acid compound with a substituted or unsubstituted amine, or acid anhydrides, or mixed anhydrides. Simple aliphatic or aromatic esters, amides and anhydrides derived from acidic groups pendant on the compounds of this invention are preferred prodrugs. In some cases it is desirable to prepare double ester type prodrugs such as (acyloxy)alkyl esters or ((alkoxycarbonyl)oxy)alkylesters. Preferred are the $C_1$ to $C_8$ alkyl, $C_2$-$C_8$ alkenyl, aryl, $C_7$-$C_{12}$ substituted aryl, and $C_7$-$C_{12}$ arylalkyl esters of the compounds of the invention.

Assay Methods

Chronic Constriction Injury Model (CCI Model):

Male Sprague-Dawley rats (270-300 g; B.W., Charles River, Tsukuba, Japan) are used. The chronic constriction injury (CCI) operation is performed according to the method described by Bennett and Xie (Bennett, G. J. and Xie, Y. K. Pain, 33:87-107, 1988). Briefly, animals are anesthetized with sodium pentobarbital (64.8 mg/kg, i.p.) and the left common sciatic nerve is exposed at the level of the middle of the thigh by blunt dissection through the biceps femoris. A portion of the sciatic nerve proximal to its trifurcation is freed of adhering tissue and 4 ligatures (4-0 silk) are tied loosely around it with about 1 mm space. A sham operation is performed as same as CCI surgery except for sciatic nerve ligation. Two weeks after surgery, mechanical allodynia is evaluated by application of von Frey hairs (VFHs) to the plantar surface of the hind paw. The lowest amount of force of VFH required to elicit a response is recorded as the paw withdrawal threshold (PWT). VFH testing is performed at 0.5, 1 and 2 hr post-dosing. Experimental data are analyzed using Kruskal-Wallis test followed by Dunn's test for multiple comparisons or Mann-Whitney U-test for paired comparison.

Caco-2 Permeability

Caco-2 permeability is measured according to the method described in Shiyin Yee, Pharmaceutical Research, 763 (1997).

Caco-2 cells are grown on filter supports (Falcon HTS multiwell insert system) for 14 days. Culture medium is removed from both the apical and basolateral compartments and the monolayers are preincubated with pre-warmed 0.3 ml apical buffer and 1.0 ml basolateral buffer for 0.75 hour at 37°

C. in a shaker water bath at 50 cycles/min. The apical buffer consists of Hanks Balanced Salt Solution, 25 mM D-glucose monohydrate, 20 mM MES Biological Buffer, 1.25 mM $CaCl_2$ and 0.5 mM $MgCl_2$ (pH 6.5). The basolateral buffer consists of Hanks Balanced Salt Solution, 25 mM D-glucose monohydrate, 20 mM HEPES Biological Buffer, 1.25 mM $CaCl_2$ and 0.5 mM $MgCl_2$ (pH 7.4). At the end of the preincubation, the media is removed and test compound solution (10 µM) in buffer is added to the apical compartment. The inserts are moved to wells containing fresh basolateral buffer and incubated for 1 hr. Drug concentration in the buffer is measured by LC/MS analysis.

Flux rate (F, mass/time) is calculated from the slope of the cumulative appearance of substrate on the receiver side and apparent permeability coefficient (Papp) is calculated from the following equation:

$$Papp(cm/sec)=(F*VD)/(SA*MD)$$

where SA is surface area for transport (0.3 $cm^2$), VD is the donor volume (0.3 ml), MD is the total amount of drug on the donor side at t=0. All data represent the mean of 2 inserts. Monolayer integrity is determined by Lucifer Yellow transport.

Human Dofetilide Binding

A cell paste of HEK-293 cells expressing the HERG product can be suspended in 10-fold volume of 50 mM Tris buffer adjusted at pH 7.5 at 25° C. with 2 M HCl containing 1 mM $MgCl_2$, 10 mM KCl. The cells are homogenized using a Polytron homogenizer (at the maximum power for 20 seconds) and centrifuged at 48,000 g for 20 minutes at 4° C. The pellet is resuspended, homogenized and centrifuged once more in the same manner. The resultant supernatant is discarded and the final pellet is resuspended (10-fold volume of 50 mM Tris buffer) and homogenized at the maximum power for 20 seconds. The membrane homogenate is aliquoted and stored at −80° C. until use. An aliquot is used for protein concentration determination using a Protein Assay Rapid Kit and ARVO SX plate reader (Wallac). All the manipulation, stock solution and equipment are kept on ice at all times. For saturation assays, experiments are conducted in a total volume of 200 µl. Saturation is determined by incubating 20 µA of [3H]-dofetilide and 160 µA of membrane homogenates (20-30 µg protein per well) for 60 min at room temperature in the absence or presence of 10 µM dofetilide at final concentrations (20 µl) for total or nonspecific binding, respectively. All incubations are terminated by rapid vacuum filtration over polyetherimide (PEI) soaked glass fiber filter papers using Skatron cell harvester followed by two washes with 50 mM Tris buffer (pH 7.5 at 25° C.). Receptor-bound radioactivity is quantified by liquid scintillation counting using a Packard LS counter.

For the competition assay, compounds are diluted in 96 well polypropylene plates as 4-point dilutions in semi-log format. All dilutions are performed in DMSO first and then transferred into 50 mM Tris buffer (pH 7.5 at 25° C.) containing 1 mM $MgCl_2$, 10 mM KCl so that the final DMSO concentration becomes equal to 1%. Compounds are dispensed in triplicate in assay plates (4 µl). Total binding and nonspecific binding wells are set up in 6 wells as vehicle and 10 µM dofetilide at final concentration, respectively. The radioligand is prepared at 5.6× final concentration and this solution is added to each well (36 µl). The assay is initiated by addition of YSi poly-L-lysine Scintillation Proximity Assay (SPA) beads (50 µl, 1 mg/well) and membranes (110 µl, 20 µg/well). Incubation is continued for 60 min at room temperature. Plates are incubated for a further 3 hours at room temperature for beads to settle. Receptor-bound radioactivity is quantified by counting Wallac MicroBeta plate counter.

HERG Assay

HEK 293 cells which stably express the HERG potassium channel are used for electrophysiological study. The methodology for stable transfection of this channel in HEK cells can be found elsewhere (Z. Zhou et al., 1998, Biophysical Journal, 74, pp 230-241). Before the day of experimentation, the cells are harvested from culture flasks and plated onto glass coverslips in a standard Minimum Essential Medium (MEM) medium with 10% Fetal Calf Serum (FCS). The plated cells are stored in an incubator at 37° C. maintained in an atmosphere of 95%$O_2$/5% $CO_2$. Cells are studied between 15-28 hrs after harvest.

HERG currents are studied using standard patch clamp techniques in the whole-cell mode. During the experiment the cells are superfused with a standard external solution of the following composition (mM); NaCl, 130; KCl, 4; $CaCl_2$, 2; $MgCl_2$, 1; Glucose, 10; HEPES, 5; pH 7.4 with NaOH. Whole-cell recordings are made using a patch clamp amplifier and patch pipettes which have a resistance of 1-3 MOhm when filled with the standard internal solution of the following composition (mM); KCl, 130; MgATP, 5; $MgCl_2$, 1.0; HEPES, 10; EGTA 5, pH 7.2 with KOH. Only those cells with access resistances below 15MΩ and seal resistances>1GΩ are accepted for further experimentation. Series resistance compensation is applied up to a maximum of 80%. No leak subtraction is done. However, acceptable access resistance depends on the size of the recorded currents and the level of series resistance compensation that can safely be used. Following the achievement of whole cell configuration and sufficient time for cell dialysis with pipette solution (>5 min), a standard voltage protocol is applied to the cell to evoke membrane currents. The voltage protocol is as follows. The membrane is depolarized from a holding potential of −80 mV to +40 mV for 1000 ms. This is followed by a descending voltage ramp (rate 0.5 mV msec-1) back to the holding potential. The voltage protocol is applied to a cell continuously throughout the experiment every 4 seconds (0.25 Hz). The amplitude of the peak current elicited around −40 mV during the ramp is measured. Once stable evoked current responses are obtained in the external solution, vehicle (0.5% DMSO in the standard external solution) is applied for 10-20 min by a peristatic pump. Provided there are minimal changes in the amplitude of the evoked current response in the vehicle control condition, the test compound of either 0.3, 1, 3 or 10 mM is applied for a 10 min period. The 10 min period includes the time during which supplying solution is passing through the tube from solution reservoir to the recording chamber via the pump. Exposure time of cells to the compound solution is more than 5 min after the drug concentration in the chamber well reaches the intended concentration. There is a subsequent wash period of a 10-20 min to assess reversibility. Finally, the cells are exposed to high dose of dofetilide (5 mM), a specific IKr blocker, to evaluate the insensitive endogenous current.

All experiments are performed at room temperature (23±1° C.). Evoked membrane currents are recorded on-line on a computer, filtered at 500-1 KHz (Bessel −3 dB) and sampled at 1-2 KHz using the patch clamp amplifier and a specific data analyzing software. Peak current amplitude, which generally occurs at around −40 mV, is measured off line on the computer.

The arithmetic mean of the ten values of amplitude is calculated under vehicle control conditions and in the presence of drug. Percent decrease of IN in each experiment is obtained by the normalized current value using the following formula: IN=(1−ID/IC)×100, where ID is the mean current value in the presence of drug and IC is the mean current value under control conditions. Separate experiments are performed for each drug concentration or time-matched control, and arithmetic mean in each experiment is defined as the result of the study.

Half-life in Human Liver Microsomes (HLM)

Test compounds (1 µM) are incubated with 3.3 mM $MgCl_2$ and 0.78 mg/mL HLM (HL101) in 100 mM potassium phosphate buffer (pH 7.4) at 37° C. on the 96-deep well plate. The reaction mixture is split into two groups, a non-P450 and a P450 group. NADPH is only added to the reaction mixture of the P450 group. An aliquot of samples of the P450 group is collected at 0, 10, 30, and 60 min time point, where 0 min time point indicates the time when NADPH is added into the reaction mixture of the P450 group. An aliquot of samples of non-P450 group is collected at −10 and 65 mM time point. Collected aliquots are extracted with acetonitrile solution containing an internal standard. The precipitated protein is spun down in a centrifuge (2000 rpm, 15 min). The compound concentration in the supernatant is measured by LC/MS/MS system.

The half-life value is obtained by plotting the natural logarithm of the peak area ratio of compounds/internal standard versus time. The slope of the line of best fit through the points yields the rate of metabolism (k). This is converted to a half-life value using following equations:

Half-life=ln 2/k

Mono-iodoacetate (MIA)-induced OA Model

Male 6-weeks-old Sprague-Dawley (SD, Japan SLC or Charles River Japan) rats are anesthetized with pentobarbital. The injection site (knee) of MIA is shaved and cleaned with 70% ethanol. Twenty-five ml of MIA solution or saline is injected in the right knee joint using a 29G needle. The effect of joint damage on the weight distribution through the right (damaged) and left (untreated) knee is assessed using an incapacitance tester (Linton Instrumentation, Norfolk, UK). The force exerted by each hind limb is measured in grams. The weight-bearing (WB) deficit is determined by a difference of weight loaded on each paw. Rats are trained to measure the WB once a week until 20 days post MIA-injection. Analgesic effects of compounds are measured at 21 days after the MIA injection. Before the compound administration, the "pre value" of WB deficit is measured. After the administration of compounds, attenuation of WB deficits is determined as analgesic effects.

Complete Freund's Adjuvant (CFA) Induced Thermal and Mechanical Hyperalgesia in Rats Thermal Hyperalgesia Male 6-week-old SD rats are used. Complete Freund's adjuvant (CFA, 300 mg of *Mycobacterium Tuberculosis* H37RA (Difco, MI) in 100 µL of liquid paraffin (Wako, Osaka, Japan)) is injected into the plantar surface of a hind paw of the rats. Two days after CFA-injection, thermal hyperalgesia is determined by the method described previously (Hargreaves et al., 1988) using the plantar test apparatus (Ugo-Basil, Varese, Italy). Rats are adapted to the testing environment for at least 15 minutes prior to any stimulation. Radiant heat is applied to the plantar surface of a hind paw and paw withdrawal latencies (PWL, seconds) are determined. The intensity of radiant heat is adjusted to produce the stable PWL of 10 to 15 seconds. The test compound is administered in a volume of 0.5 mL per 100 g body weight. PWL are measured after 1, 3 or 5 hours after drug administration.

Mechanical Hyperalgesia

Male 4-week-old SD rats are used. CFA (300 mg of *Mycobacterium Tuberculosis* H37RA (Difco, MI) in 100 µL of liquid paraffin (Wako, Osaka, Japan)) is injected into the plantar surface of a hind paw of the rats. Two days after CFA-injection, mechanical hyperalgesia is tested by measuring paw withdrawal threshold (PWT, grams) to pressure using the analgesy-Meter (Ugo-Basile, Varese, Italy). The animals are gently restrained, and steadily increasing pressure is applied to the dorsal surface of a hind paw via a plastic tip. The pressure required to elicit paw withdrawal is determined. The test compound is administered in a volume of 0.5 mL per 100 g body weight. PWT are measured after 1, 3 or 5 hours after drug administration.

Pharmaceutical Compositions

When employed as pharmaceuticals, the amide compounds of this invention are typically administered in the form of a pharmaceutical composition. Such compositions can be prepared in a manner well known in the pharmaceutical art and comprise at least one active compound.

Generally, the compounds of this invention are administered in a pharmaceutically effective amount. The amount of the compound actually administered will typically be determined by a physician, in the light of the relevant circumstances, including the condition to be treated, the chosen route of administration, the actual compound administered, the age, weight, and response of the individual patient, the severity of the patient's symptoms, and the like.

The pharmaceutical compositions of this invention can be administered by a variety of routes including by way of non limiting example, oral, rectal, transdermal, subcutaneous, intravenous, intramuscular and intranasal. Depending upon the intended route of delivery, the compounds of this invention are preferably formulated as either injectable or oral compositions or as salves, as lotions or as patches all for transdermal administration.

The compositions for oral administration can take the form of bulk liquid solutions or suspensions, or bulk powders. More commonly, however, the compositions are presented in unit dosage forms to facilitate accurate dosing. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. Typical unit dosage forms include prefilled, premeasured ampules or syringes of the liquid compositions or pills, tablets, capsules or the like in the case of solid compositions. In such compositions, the furansulfonic acid compound is usually a minor component (from about 0.1 to about 50% by weight or preferably from about 1 to about 40% by weight) with the remainder being various vehicles or carriers and processing aids helpful for forming the desired dosing form.

Liquid forms suitable for oral administration may include a suitable aqueous or nonaqueous vehicle with buffers, suspending and dispensing agents, colorants, flavors and the like. Solid forms may include, for example, any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate; a glidant such as colloidal silicon dioxide; a sweetening agent such as sucrose or saccharin; or a flavoring agent such as peppermint, methyl salicylate, or orange flavoring.

Injectable compositions are typically based upon injectable sterile saline or phosphate-buffered saline or other injectable carriers known in the art. As before, the active compound in such compositions is typically a minor component, often being from about 0.05 to 10% by weight with the remainder being the injectable carrier and the like.

Transdermal compositions are typically formulated as a topical ointment or cream containing the active ingredient(s), generally in an amount ranging from about 0.01 to about 20% by weight, preferably from about 0.1 to about 20% by weight, preferably from about 0.1 to about 10% by weight, and more preferably from about 0.5 to about 15% by weight. When formulated as a ointment, the active ingredients will typically be combined with either a paraffinic or a water-miscible ointment base. Alternatively, the active ingredients may be formulated in a cream with, for example an oil-in-water cream base. Such transdermal formulations are well-known in the art and generally include additional ingredients to enhance the dermal penetration of stability of the active ingredients or the formulation. All such known transdermal formulations and ingredients are included within the scope of this invention.

The compounds of this invention can also be administered by a transdermal device. Accordingly, transdermal administration can be accomplished using a patch either of the reservoir or porous membrane type, or of a solid matrix variety.

The above-described components for orally administrable, injectable or topically administrable compositions are merely representative. Other materials as well as processing techniques and the like are set forth in Part 8 of *Remington's Pharmaceutical Sciences* 17th edition, 1985, Mack Publishing Company, Easton, Pa., which is incorporated herein by reference.

The compounds of this invention can also be administered in sustained release forms or from sustained release drug delivery systems. A description of representative sustained release materials can be found in *Remington's Pharmaceutical Sciences*.

The following formulation examples illustrate representative pharmaceutical compositions that may be prepared in accordance with this invention. The present invention, however, is not limited to the following pharmaceutical compositions.

Formulation 1—Tablets

A compound of the invention is admixed as a dry powder with a dry gelatin binder in an approximate 1:2 weight ratio. A minor amount of magnesium stearate is added as a lubricant. The mixture is formed into 240-270 mg tablets (80-90 mg of active compound per tablet) in a tablet press.

Formulation 2—Capsules

A compound of the invention is admixed as a dry powder with a starch diluent in an approximate 1:1 weight ratio. The mixture is filled into 250 mg capsules (125 mg of active compound per capsule).

Formulation 3—Liquid

A compound of the invention (125 mg) may be admixed with sucrose (1.75 g) and xanthan gum (4 mg) and the resultant mixture may be blended, passed through a No. 10 mesh U.S. sieve, and then mixed with a previously made solution of microcrystalline cellulose and sodium carboxymethyl:cellulose (11:89, 50 mg) in water. Sodium benzoate (10 mg), flavor, and color are diluted with water and added with stirring. Sufficient water may then added to produce a total volume of 5 mL.

Formulation 4—Tablets

A compound of the invention may be admixed as a dry powder with a dry gelatin binder in an approximate 1:2 weight ratio. A minor amount of magnesium stearate is added as a lubricant. The mixture is formed into 450-900 mg tablets (150-300 mg of active compound) in a tablet press.

Formulation 5—Injection

A compound of the invention is dissolved or suspended in a buffered sterile saline injectable aqueous medium to a concentration of approximately 5 mg/mL.

Formulation 6—Topical

Stearyl alcohol (250 g) and a white petrolatum (250 g) are melted at about 75° C. and then a mixture of a compound of the invention (50 g) methylparaben (0.25 g), propylparaben (0.15 g), sodium lauryl sulfate (10 g), and propylene glycol (120 g) dissolved in water (about 370 g) is added and the resulting mixture is stirred until it congeals.

Methods of Treatment

The present compounds are used as therapeutic agents for the treatment of conditions in mammals. Accordingly, the compounds and pharmaceutical compositions of this invention find use as therapeutics for preventing and/or treating neurodegenerative, autoimmune and inflammatory conditions in mammals including humans. Thus, and as stated earlier, the present invention includes within its scope, and extends to, the recited methods of treatment, as well as to the compounds for use in such methods and for the preparation of medicaments useful for such methods.

In a method of treatment aspect, this invention provides a method of treating a mammal susceptible to or afflicted with a condition associated with arthritis, uveitis, asthma, myocardial infarction, traumatic brain injury, acute spinal cord injury, alopecia (hair loss), inflammatory bowel disease and autoimmune disorders, which method comprises administering an effective amount of one or more of the pharmaceutical compositions just described.

In yet another method of treatment aspect, this invention provides a method of treating a mammal susceptible to or afflicted with a condition that gives rise to pain responses or that relates to imbalances in the maintenance of basal activity of sensory nerves. Compounds have use as analgesics for the treatment of pain of various geneses or etiology, for example acute, inflammatory pain (such as pain associated with osteoarthritis and rheumatoid arthritis); various neuropathic pain syndromes (such as post-herpetic neuralgia, trigeminal neuralgia, reflex sympathetic dystrophy, diabetic neuropathy, Guillian Barre syndrome, fibromyalgia, phantom limb pain, post-masectomy pain, peripheral neuropathy, HIV neuropathy, and chemotherapy-induced and other iatrogenic neuropathies); visceral pain, (such as tht associated with gastroesophageal reflex disease, irritable bowel syndrome, inflammatory bowel disease, pancreatitis, and various gynecological and urological disorders), dental pain and headache (such as migraine, cluster headache and tension headache).

In additional method of treatment aspects, this invention provides methods of treating a mammal susceptible to or afflicted with neurodegenerative diseases and disorders such as, for example Parkinson's disease, Alzheimer's disease and multiple sclerosis; diseases and disorders which are mediated by or result in neuroinflammation such as, for example traumatic brain injury, stroke, and encephalitis; centrally-mediated neuropsychiatric diseases and disorders such as, for example depression mania, bipolar disease, anxiety, schizophrenia, eating disorders, sleep disorders and cognition disorders; epilepsy and seizure disorders; prostate, bladder and bowel dysfunction such as, for example urinary incontinence, urinary hesitancy, rectal hypersensitivity, fecal incontinence, benign prostatic hypertrophy and inflammatory bowel disease; respiratory and airway disease and disorders such as, for example, allergic rhinitis, asthma and reactive airway disease and chronic obstructive pulmonary disease; diseases and disorders which are mediated by or result in inflammation such as, for example rheumatoid arthritis and osteoarthritis, myocardial infarction, various autoimmune diseases and disorders, uveitis and atherosclerosis; itch/pruritus such as, for example psoriasis; alopecia (hair loss); obesity; lipid disorders; cancer; blood pressure; spinal cord injury; and renal disorders method comprises administering an effective condition-treating or condition-preventing amount of one or more of the pharmaceutical compositions just described.

Injection dose levels range from about 0.1 mg/kg/hour to at least 10 mg/kg/hour, all for from about 1 to about 120 hours and especially 24 to 96 hours. A preloading bolus of from about 0.1 mg/kg to about 10 mg/kg or more may also be administered to achieve adequate steady state levels. The maximum total dose is not expected to exceed about 2 g/day for a 40 to 80 kg human patient.

For the prevention and/or treatment of long-term conditions, such as neurodegenerative and autoimmune conditions, the regimen for treatment usually stretches over many months or years so oral dosing is preferred for patient convenience and tolerance. With oral dosing, one to five and especially two to four and typically three oral doses per day are representative regimens. Using these dosing patterns, each dose provides from about 0.01 to about 20 mg/kg of the compound or its derivative, with preferred doses each providing from about 0.1 to about 10 mg/kg and especially about 1 to about 5 mg/kg.

Transdermal doses are generally selected to provide similar, or lower blood levels than are achieved using injection doses.

When used to prevent the onset of a neurodegenerative, autoimmune or inflammatory condition, the compounds or their derivatives of this invention will be administered to a patient at risk for developing the condition, typically on the advice and under the supervision of a physician, at the dosage levels described above. Patients at risk for developing a particular condition generally include those that have a family history of the condition, or those who have been identified by genetic testing or screening to be particularly susceptible to developing the condition.

The compounds of this invention can be administered as the sole active agent or they can be administered in combination with other agents, including other active derivatives. A VR1 antagonist may be usefully combined with another pharmacologically active compound, or with two or more other pharmacologically active compounds, particularly in the treatment of pain. For example, a VR1 antagonist, particularly a compound of formula (I), or a pharmaceutically acceptable salt or solvate thereof, as defined above, may be administered simultaneously, sequentially or separately in combination with one or more agents selected from:

an opioid analgesic, e.g. morphine, heroin, hydromorphone, oxymorphone, levorphanol, levallorphan, methadone, meperidine, fentanyl, cocaine, codeine, dihydrocodeine, oxycodone, hydrocodone, propoxyphene, nalmefene, nalorphine, naloxone, naltrexone, buprenorphine, butorphanol, nalbuphine or pentazocine;

a nonsteroidal antiinflammatory drug (NSAID), e.g. aspirin, diclofenac, diflusinal, etodolac, fenbufen, fenoprofen, flufenisal, flurbiprofen, ibuprofen, indomethacin, ketoprofen, ketorolac, meclofenamic acid, mefenamic acid, meloxicam, nabumetone, naproxen, nimesulide, nitroffurbiprofen, olsalazine, oxaprozin, phenylbutazone, piroxicam, sulfasalazine, sulindac, tolmetin or zomepirac;

a barbiturate sedative, e.g. amobarbital, aprobarbital, butabarbital, butabital, mephobarbital, metharbital, methohexital, pentobarbital, phenobartital, secobarbital, talbutal, theamylal or thiopental;

a benzodiazepine having a sedative action, e.g. chlordiazepoxide, clorazepate, diazepam, flurazepam, lorazepam, oxazepam, temazepam or triazolam;

an H1 antagonist having a sedative action, e.g. diphenhydramine, pyrilamine, promethazine, chlorpheniramine or chlorcyclizine;

a sedative such as glutethimide, meprobamate, methaqualone or dichloralphenazone;

a skeletal muscle relaxant, e.g. baclofen, carisoprodol, chlorzoxazone, cyclobenzaprine, methocarbamol or orphrenadine;

an NMDA receptor antagonist, e.g. dextromethorphan ((+)-3-hydroxy-N-methylmorphinan) or its metabolite dextrorphan ((+)-3-hydroxy-N-methylmorphinan), ketamine, memantine, pyrroloquinoline quinine, cis-4-(phosphonomethyl)-2-piperidinecarboxylic acid, budipine, EN-3231 (MorphiDex®, a combination formulation of morphine and dextromethorphan), topiramate, neramexane or perzinfotel including an NR2B antagonist, e.g. ifenprodil, traxoprodil or (−)-(R)-6-{2-[4-(3-fluorophenyl)-4-hydroxy-1-piperidinyl]-1-hydroxyethyl-3,4-dihydro-2(1H)-quinolinone;

an alpha-adrenergic, e.g. doxazosin, tamsulosin, clonidine, guanfacine, dexmetatomidine, modafinil, or 4-amino-6,7-dimethoxy-2-(5-methane-sulfonamido-1,2,3,4-tetrahydroisoquinol-2-yl)-5-(2-pyridyl)quinazoline;

a tricyclic antidepressant, e.g. desipramine, imipramine, amitriptyline or nortriptyline;

an anticonvulsant, e.g. carbamazepine, lamotrigine, topiratmate or valproate;

a tachykinin (NK) antagonist, particularly an NK-3, NK-2 or NK-1 antagonist, e.g. (aR,9R)-7-[3,5-bis(trifluoromethyl)benzyl]-8,9,10,11-tetrahydro-9-methyl-5-(4-methylphenyl)-7H-[1,4]diazocino[2,1-g][1,7]-naphthyridine-6-13-dione (TAK-637), 5-[[(2R,3S)-2-[(1R)-1-[3,5-bis(trifluoromethyl)phenyl]ethoxy-3-(4-fluorophenyl)-4-morpholinyl]-methyl]-1,2-dihydro-3H-1,2,4-triazol-3-one (MK-869), aprepitant, lanepitant, dapitant or 3-[[2-methoxy-5-(trifluoromethoxy)phenyl]-methylamino]-2-phenylpiperidine (2S,3S);

a muscarinic antagonist, e.g. oxybutynin, tolterodine, propiverine, tropsium chloride, darifenacin, solifenacin, temiverine and ipratropium;

a COX-2 selective inhibitor, e.g. celecoxib, rofecoxib, parecoxib, valdecoxib, deracoxib, etoricoxib, or lumiracoxib;

a coal-tar analgesic, in particular paracetamol;

a neuroleptic such as droperidol, chlorpromazine, haloperidol, perphenazine, thioridazine, mesoridazine, trifluoperazine, fluphenazine, clozapine, olanzapine, risperidone, ziprasidone, quetiapine, sertindole, aripiprazole, sonepiprazole, blonanserin, iloperidone, perospirone, raclopride, zotepine, bifeprunox, asenapine, lurasidone, amisulpride, balaperidone, palindore, eplivanserin, osanetant, rimonabant, meclinertant, Miraxion® or sarizotan;

a beta-adrenergic such as propranolol;

a local anaesthetic such as mexiletine;

a corticosteroid such as dexamethasone;

a 5-HT receptor agonist or antagonist, particularly a 5-HT1B/1D agonist such as eletriptan, sumatriptan, naratriptan, zolmitriptan or rizatriptan;

a 5-HT2A receptor antagonist such as R(+)-alpha-(2,3-dimethoxy-phenyl)-1-[2-(4-fluorophenylethyl)]-4-piperidinemethanol (MDL-100907);

a cholinergic (nicotinic) analgesic, such as ispronicline (TC-1734), (E)-N-methyl-4-(3-pyridinyl)-3-buten-1-amine (RJR-2403), (R)-5-(2-azetidinylmethoxy)-2-chloropyridine (ABT-594) or nicotine;

Tramadol®;

a PDEV inhibitor, such as 5-[2-ethoxy-5-(4-methyl-1-piperazinyl-sulphonyl)phenyl]-1-methyl-3-n-propyl-1,6-dihydro-7H-pyrazolo[4,3-d]pyrimidin-7-one (sildenafil), (6R;12aR)-2,3,6,7,12,12a-hexahydro-2-methyl-6-(3,4-methylenedioxyphenyl)-pyrazino[2',': 6,1]-pyrido[3,4-b]indole-1,4-dione (IC-351 or tadalafil), 2-[2-ethoxy-5-(4-ethyl-piperazin-1-yl-1-sulphonyl)-phenyl]-5-methyl-7-propyl-3H-imidazo[5,1-f][1,2,4]triazin-4-one (vardenafil), 5-(5-acetyl-2-butoxy-3-pyridinyl)-3-ethyl-2-(1-ethyl-3-azetidinyl)-2,6-dihydro-7H-pyrazolo[4,3-d]pyrimidin-7-one, 5-(5-acetyl-2-propoxy-3-pyridinyl)-3-ethyl-2-(1-isopropyl-3-azetidinyl)-2,6-dihydro-7H-pyrazolo[4,3-d]pyrimidin-7-one, 5-[2-ethoxy-5-(4-ethylpiperazin-1-ylsulphonyl)pyridin-3-yl]-3-ethyl-2-[2-methoxyethyl]-2,6-dihydro-7H-pyrazolo[4,3-d]pyrimidin-7-one, 4-[(3-chloro-4-methoxybenzyl)amino]-2-[(2S)-2-(hydroxymethyl)pyrrolidin-1-yl]-N-(pyrimidin-2-ylmethyl)pyrimidine-5-carboxamide, 3-(1-methyl-7-oxo-3-propyl-6,7-dihydro-1H-pyrazolo[4,3-d]pyrimidin-5-yl)-N-[2-(1-methylpyrrolidin-2-yl)ethyl]-4-propoxybenzenesulfonamide;

an alpha-2-delta ligand such as gabapentin, pregabalin, 3-methylgabapentin, (1a,3a,5a)(3-amino-methyl-bicyclo[3.2.0]hept-3-yl)-acetic acid, (3S,5R)-3-aminomethyl-5-methyl-heptanoic acid, (3S,5R)-3-amino-5-methyl-heptanoic acid, (3S,5R)-3-amino-5-methyl-octanoic acid, (2S,4S)-4-(3-chlorophenoxy)proline, (2S,4S)-4-(3-fluorobenzyl)-proline, [(1R,5R,6S)-6-(aminomethyl)bicyclo[3.2.0]hept-6-yl]acetic acid, 3-(1-aminomethyl-cyclohexylmethyl)-4H-[1,2,4]oxadiazol-5-one, C-[1-(1H-tetrazol-5-ylmethyl)-cycloheptyl]-methylamine, (3S,4S)-(1-aminomethyl-3,4-dimethyl-cyclopentyl)-acetic acid, (3S,5R)-3-aminomethyl-5-methyl-octanoic acid, (3S,5R)-3-amino-5-methyl-nonanoic acid, (3S,5R)-3-amino-5-methyl-octanoic acid, (3R,4R,5R)-3-amino-4,5-dimethyl-heptanoic acid and (3R,4R,5R)-3-amino-4,5-dimethyl-octanoic acid;

a cannabinoid;

a serotonin reuptake inhibitor such as sertraline, sertraline metabolite demethylsertraline, fluoxetine, norfluoxetine (fluoxetine desmethyl metabolite), fluvoxamine, paroxetine, citalopram, citalopram metabolite desmethylcitalopram, escitalopram, d,l-fenfluramine, femoxetine, ifoxetine, cyanodothiepin, litoxetine, dapoxetine, nefazodone, cericlamine and trazodone;

a noradrenaline (norepinephrine) reuptake inhibitor, such as maprotiline, lofepramine, mirtazepine, oxaprotiline, fezolamine, tomoxetine, mianserin, buproprion, buproprion metabolite hydroxybuproprion, nomifensine and viloxazine (Vivalan®), especially a selective noradrenaline reuptake inhibitor such as reboxetine, in particular (S,S)-reboxetine;

a dual serotonin-noradrenaline reuptake inhibitor, such as venlafaxine, venlafaxine metabolite O-desmethylvenlafaxine, clomipramine, clomipramine metabolite desmethylclomipramine, duloxetine, milnacipran and imipramine;

an inducible nitric oxide synthase (iNOS) inhibitor such as S-[2-[(1-iminoethyl)amino]ethyl]-L-homocysteine, S-[2-[(1-iminoethyl)-amino]ethyl]-4,4-dioxo-L-cysteine, S-[2-[(1-iminoethyl)amino]ethyl]-2-methyl-L-cysteine, (2S,5S)-2-amino-2-methyl-7-[(1-iminoethyl)amino]-5-heptenoic acid, 2-[[(1R,3S)-3-amino-4-hydroxy-1-(5-thiazolyl)-butyl]thio]-5-chloro-3-pyridinecarbonitrile; 2-[[(1R,3S)-3-amino-4-hydroxy-1-(5-thiazolyl)butyl]thio]-4-chlorobenzonitrile, (2S,4R)-2-amino-4-[[2-chloro-5-(trifluoromethyl)phenyl]thio]-5-thiazolebutanol, 2-[[(1R,3S)-3-amino-4-hydroxy-1-(5-thiazolyl)butyl]thio]-6-(trifluoromethyl)-3 pyridinecarbonitrile, 2-[[(1R,3S)-3-amino-4-hydroxy-1-(5-thiazolyl)butyl]thio]-5-chlorobenzonitrile, N-[4-[2-(3-chlorobenzylamino)ethyl]phenyl]thiophene-2-carboxamidine, or guanidinoethyldisulfide;

an acetylcholinesterase inhibitor such as donepezil;

a prostaglandin E2 subtype 4 (EP4) antagonist such as N-[({2-[4-(2-ethyl-4,6-dimethyl-1H-imidazo[4,5-c]pyridin-1-yl)phenyl]ethyl}amino)-carbonyl]-4-methyl-benzenesulfonamide or 4-[(1S)-1-({[5-chloro-2-(3-fluorophenoxy)pyridin-3-yl]carbonyl}amino)ethyl]benzoic acid;

a leukotriene B4 antagonist; such as 1-(3-biphenyl-4-ylmethyl-4-hydroxy-chroman-7-yl)-cyclopentanecarboxylic acid (CP-105696), 5-]2-(2-Carboxyethyl)-3-[6-(4-methoxyphenyl)-5E-hexenyl]oxyphenoxy]-valeric acid (ONO-4057) or DPC-11870, a 5-lipoxygenase inhibitor, such as zileuton, 6-[(3-fluoro-5-[4-methoxy-3,4,5,6-tetrahydro-2H-pyran-4-yl])phenoxy-methyl]-1-methyl-2-quinolone (ZD-2138), or 2,3,5-trimethyl-6-(3-pyridylmethyl),1,4-benzoquinone (CV-6504);

a sodium channel blocker, such as lidocaine;

a 5-HT3 antagonist, such as ondansetron;

and the pharmaceutically acceptable salts and solvates thereof.

In as much as it may desirable to administer a combination of active compounds, for example, for the purpose of treating a particular disease or condition, it is within the scope of the present invention that two or more pharmaceutical compositions, at least one of which contains a compound in accordance with the invention, may conveniently be combined in the form of a kit suitable for coadministration of the compositions.

Preparation of the Compounds

The compounds of this invention can be prepared from readily available starting materials using the following general methods and procedures. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. The choice of a suitable protecting group for a particular functional group as well as suitable conditions for protection and deprotection are well known in the art. For example, numerous protecting groups, and their introduction and removal, are described in T. W. Greene and P. G. M. Wuts, *Protecting Groups in Organic Synthesis*, Second Edition, Wiley, New York, 1991, and references cited therein.

The target compounds are synthesized by known reactions outlined in the following schemes. The products are isolated and purified by known standard procedures. Such procedures include (but are not limited to) recrystallization, column chromatography or HPLC.

In this specification, especially in "General Synthesis" and "Examples", the following abbreviations can and may be used:

BEP 2-bromo-1-ethylpyridinium tetrafluoroborate

BOP benzotriazol-1-yloxy-tris(dimethylamino)phosphonium hexafluorophosphate

CDI 2-chloro-1,3-dimethylimidazolinium chloride

Co(TPP) 5, 10, 15, 20 tetraphenyl-21H, 23H porphine Co(II)

DCC dicyclohexylcarbodiimide

DCM dichloromethane

DME 1,2-dimethoxyethane, dimethoxyethane

DMF N,N-dimethylformamide

DMSO dimethyl sulfoxide

EDC 1-ethyl-3-(3'-dimethylaminopropyl)carbodiimide hydrogen chloride)

EtOAc ethyl acetate

EtOH ethanol

HBTU O-Benzotriazole-N,N,N',N'-tetramethyl-uronium-hexafluoro-phosphate

HOBt 1-hydroxybenzotriazole

MeOH methanol

NMP N-methyl-2-pyrroliidone

PdCl₂ (pddf).CH₂Cl₂ palladiumdichloro-1,1'-bis(diphenylphosphino)ferrocene-dichloromethane complex THF tetrahydrofuran TFA trifluoroacetic acid General Synthesis The compounds of the present invention may be prepared by a variety of processes well known for the preparation of compounds of this type, for example as shown in the following reaction Schemes. The term "protecting group", as used hereinafter, means a hydroxy or amino protecting group which is selected from typical hydroxy or amino protecting groups described in Protective Groups in Organic Synthesis edited by T. W. Greene et al. (John Wiley & Sons, 1999).

EXAMPLE 1

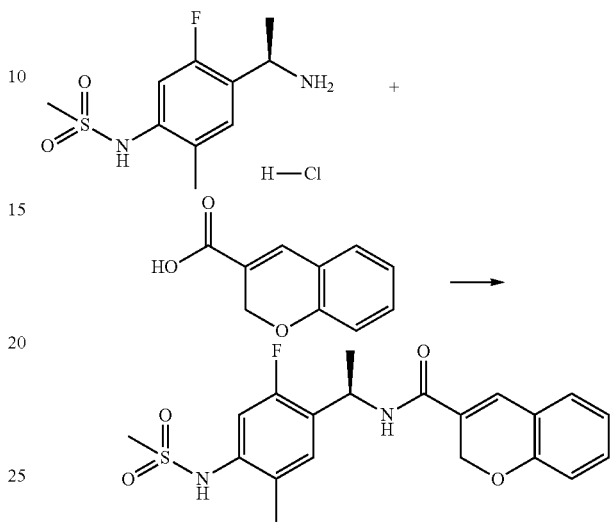

(R)—N-(1-(2-Fluoro-5-methyl-4-(methylsulfonamido)phenyl)ethyl)-2h-chromene-3-carboxamide To a solution of 2H-chromene-3-carboxylic acid (0.015 g, 0.085 mmol), N-[4-((R)-1-aminoethyl)-5-fluoro-2-methylphenyl]methanesulfonamide hydrochloride (20.00 mg, 0.07 mmol) and N,N,N',N'-tetramethyl-O-(7-azabenzotriazol-1-yl)uronium hexafluorophosphate (0.032 g, 0.085 mmol) in N,N-dimethylformamide (0.39 g) was added N,N-diisopropylethylamine (0.046 g, 0.35 mmol). Tetrahydrofuran (0.38 g) was added to dilute solution. The reaction was stirred overnight. It was then concentrated and purified by HPLC to obtain the product (10.8 mg, 37%) a solid. m/z=405.1 (M+1). $^1$H-NMR (400 MHz, DMSO-d) δ 9.19 (s, 1H), 8.61 (d, 1H, J=7.66 Hz), 7.37 (s, 1H), 7.30-7.21 (m, 3H), 7.07 (d, 1H, J=11.41 Hz), 6.96 (dt, 1H, J=7.54 Hz), 6.84 (d, 1H, J=7.81 Hz), 5.25-5.18 (m, 1H), 4.88 (s, 2H), 3.02 (s, 3H), 2.25 (s, 3H), 1.41 (d, 3H, J=7.07 Hz).

EXAMPLE 2

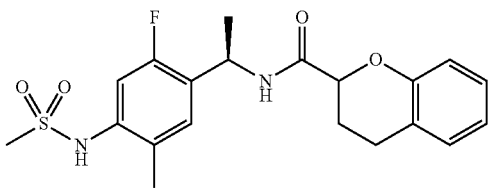

Chroman-2-carboxylic acid [(r)-1-(2-fluoro-4-methanesulfonylamino-5-methylphenyl)ethylamide To a vial containing chroman-2-carboxylic acid (19 mg, 0.1 mmol) was added a solution of HATU (40 mg, 0.1 mmol), DIPEA (42 µl, 0.24 mmol) and DMAP (1 mg, 0.01 mmol) in anhydrous DMF (1.5 mL). After stirring for 5 minutes, a solution of N-[4-((R)-1-aminoethyl)-5-fluoro-2-methylphenyl]methanesulfonamide hydrochloride (25 mg, 0.09 mmol) and DIPEA (21 μl, 0.12 mmol) in anhydrous DMF (1 mL) was added. The reaction was stirred at room temperature overnight, then poured into saturated NaHCO$_3$ solution (30 mL) and extracted with EtOAc (3×30 mL). The combined organics were washed with brine (3×30 mL), dried (MgSO$_4$), filtered and concentrated. Flash chromatography (0 to 3% MeOH in DCM) gave the title compound (14 mg, 37%) as a solid. m/z=407.2 (M+1), r.t.=2.99 mins. $^1$H NMR (400 MHz; d$_6$-DMSO) δ 9.19 (1H, d), 8.38 (1H, dd), 7.29-7.03 (4H, m), 6.92-6.81 (2H, m), 5.21-5.12 (1H, m), 4.62-4.54 (1H, m), 3.01 (3H, d), 2.85-2.73 (1H, m), 2.68-2.60 (1H, m), 2.27 (3H, s), 2.15-2.06 (1H, m), 1.99-1.87 (1H, m), 1.38 (3H, t).

EXAMPLE 3

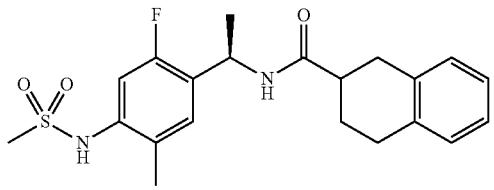

1,2,3,4-Tetrahydronaphthalene-2-carboxylic acid f(r)-1-(2-fluoro-4-methanesulfonylamino-5-methylphenyl)ethylamide To a vial containing 1,2,3,4-tetrahydronaphthalene-2-carboxylic acid (19 mg, 0.1 mmol) was added a solution of HATU (40 mg, 0.1 mmol), DIPEA (42 μl, 0.24 mmol) and DMAP (1 mg, 0.01 mmol) in anhydrous DMF (1.5 mL). After stirring for 5 minutes, a solution of N-[4-((R)-1-aminoethyl)-5-fluoro-2-methylphenyl]methanesulfonamide hydrochloride (25 mg, 0.09 mmol) and DIPEA (21 μl, 0.12 mmol) in anhydrous DMF (1 mL) was added. The reaction was stirred at room temperature overnight, then poured into saturated NaHCO$_3$ solution (30 mL) and extracted with EtOAc (3×30 mL). The combined organics were washed with brine (3×30 mL), dried (MgSO$_4$), filtered and concentrated. Flash chromatography (0 to 4% MeOH in DCM) gave the title compound (21 mg, 56%) as a solid. m/z=405.1 (M+1), r.t.=3.04 mins. $^1$H NMR (400 MHz; d$_7$-DMF) δ 9.61 (1H, s), 8.79 (1H, t), 7.66 (1H, d), 7.51-7.48 (5H, m), 5.56-5.50 (1H, m), 3.45 (3H, d), 3.26-3.17 (4H, m), 3.10-2.97 (1H, m), 2.67 (3H, s), 2.42-2.34 (1H, m), 2.16-2.03 (1H, m), 1.77 (3H, d).

EXAMPLE 4

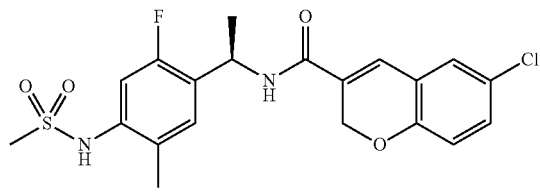

6-Chloro-2h-chromene-3-carboxylic acid [(r)-1-(2-fluoro-4-methanesulfonylamino-5-methylphenyl)ethylamide To a vial containing 6-chloro-2H-chromene-3-carboxylic acid (22 mg, 0.1 mmol) was added a solution of HATU (40 mg, 0.1 mmol), DIPEA (42 μl, 0.24 mmol) and DMAP (1 mg, 0.01 mmol) in anhydrous DMF (1.5 mL). After stirring for 5 minutes, a solution of N-[4-((R)-1-aminoethyl)-5-fluoro-2-methylphenyl]methanesulfonamide hydrochloride (25 mg, 0.09 mmol) and DIPEA (21 μl, 0.12 mmol) in anhydrous DMF (1 mL) was added. The reaction was stirred at room temperature overnight, then poured into saturated NaHCO$_3$ solution (30 mL) and extracted with EtOAc (3×30 mL). The combined organics were washed with brine (3×30 mL), dried (MgSO$_4$), filtered and concentrated. Flash chromatography (0 to 4% MeOH in DCM) gave the title compound (29 mg, 72%) as a solid. m/z=439.2 (M+1), r.t.=3.25 mins. $^1$H NMR (400 MHz; d$_6$-DMSO)S 9.19 (1H, s), 8.67 (1H, d), 7.33 (1H, d), 7.30-7.24 (3H, m), 7.07 (1H, d), 6.88 (1H, d), 5.25-5.18 (1H, m), 4.91 (2H, s), 3.02 (3H, s), 2.27 (3H, s), 1.41 (3H, d).

EXAMPLE 5

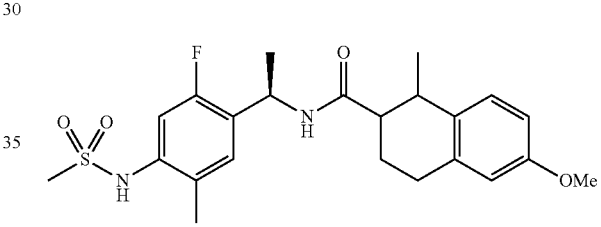

6-Methoxy-1-methyl-1,2,3,4-tetrahydronaphthalene-2-carboxylic acid [(r)-1-(2-fluoro-4-methanesulfonylamino-5-methylphenyl)ethylamide To a vial containing 6-methoxy-1-methyl-1,2,3,4-tetrahydronaphthalene-2-carboxylic acid (12 mg, 0.05 mmol) was added a solution of HATU (24 mg, 0.06 mmol), DIPEA (22 μl, 0.12 mmol) and DMAP (0.5 mg, 0.005 mmol) in anhydrous DMF (1.5 mL). After stirring for 5 minutes, a solution of N-[4-(R)-1-aminoethyl)-5-fluoro-2-methylphenyl]methanesulfonamide hydrochloride (18 mg, 0.06 mmol) and DIPEA (11 μl, 0.06 mmol) in anhydrous DMF (1 mL) was added. The reaction was stirred at room temperature overnight, then poured into saturated NaHCO$_3$ solution (30 mL) and extracted with EtOAc (3×30 mL). The combined organics were washed with brine (3×30 mL), dried (MgSO$_4$), filtered and concentrated. Flash chromatography (0 to 4% MeOH in DCM) gave the title compound (7 mg, 30%) as a solid. m/z=449.5 (M+1), r.t.=3.37 mins. $^1$H NMR (400 MHz; d$_6$-DMSO) δ 9.19 (1H, s), 8.42 (1H, t), 7.26-7.16 (2H, m), 7.07 (1H, d), 6.72-6.69 (1H, m), 6.62-6.59 (1H, m), 5.76 (1H, s), 5.14-5.08 (1H, m), 3.69 (3H, s), 3.30 (3H, s), 3.02 (3H, s), 2.75-2.67 (2H, m), 2.32-2.22 (4H, m), 1.91-1.81 (1H, m), 1.73-1.61 (1H, m), 1.35 (31-1, dd).

EXAMPLE 6

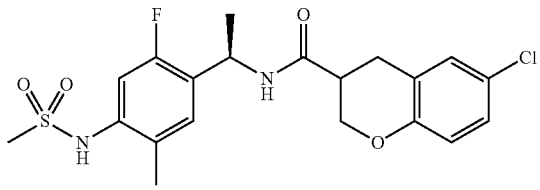

6-Chlorochroman-3-carboxylic acid [(r)-1-(2-fluoro-4-methanesulfonylamino-5-methylphenyl]ethylamide To a vial containing 6-chlorochroman-3-carboxylic acid (45 mg, 0.21 mmol) was added a solution of HATU (81 mg, 0.21 mmol), DIPEA (88 μl, 0.42 mmol) and DMAP (2.1 mg, 0.02 mmol) in anhydrous DMF (1.5 mL). After stirring for 5 minutes, a solution of N-[4-((R)-1-aminoethyl)-5-fluoro-2-methylphenyl]methanesulfonamide hydrochloride (50 mg, 0.2 mmol) and DIPEA (44 μl, 0.21 mmol) in anhydrous DMF (1 mL) was added. The reaction was stirred at room temperature overnight, then poured into saturated NaHCO$_3$ solution (30 mL) and extracted with EtOAc (3×30 mL). The combined organics were washed with brine (3×30 mL), dried (MgSO$_4$), filtered and concentrated. Flash chromatography (0 to 2.5% MeOH in DCM) gave the title compound (44 mg, 50%) as a solid. $^1$H NMR (400 MHz; d$_6$-DMSO) δ 9.19 (1H, s), 8.62-8.59 (1H, m), 7.23-7.19 (2H, m), 7.11-7.05 (2H, m), 6.78 (1H, dd), 5.10-5.04 (1H, m), 4.35-4.29 (1H, m), 3.96-3.91 (1H, m), 3.02 (3H, s), 2.90-2.80 (3H, m), 2.26 (3H, s), 1.37 (3H, d).

EXAMPLE 7

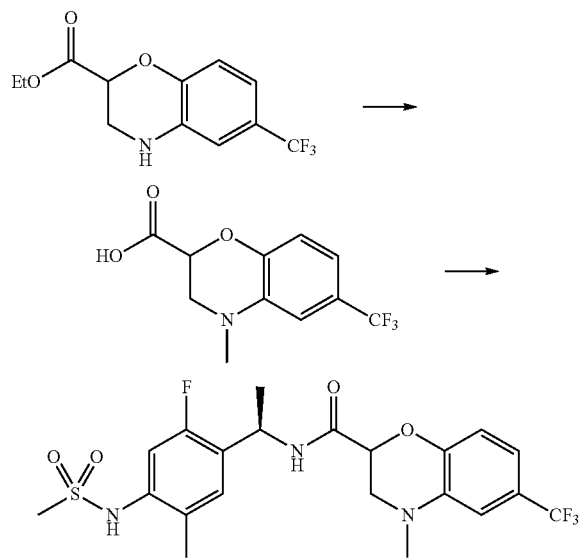

4-Methyl-6-trifluoromethyl-3,4-dihydro-2h-benzo[1,4]oxazine-2-carboxylic acid [(r)-1-(2-fluoro-4-methanesulfonylamino-5-methylphenyl]ethylamide

8A) 4-Methyl-6-trifluoromethyl-3,4-dihydro-2h-benzo[1,4]oxazine-2-carboxylic acid To a solution of 6-trifluoromethyl-3,4-dihydro-2H-benzo[1,4]oxazine-2-carboxylic acid ethyl ester (650 mg, 2.4 mmol) in anhydrous DMF (7 mL) was added K$_2$CO$_3$ (816 mg, 5.9 mmol), followed by iodomethane (294 μL, 4.7 mmol). The reaction was heated in the microwave (300 W, 150° C.) for 1 hour. After cooling, the mixture was poured into water (50 mL), acidified with 2N HCl and extracted with EtOAc (3×50 mL). The combined organics were washed with brine (3×50 mL), dried (MgSO$_4$), filtered and concentrated. Flash chromatography (0 to 12% MeOH in DCM) gave the title compound (90 mg, 10%) as a solid. m/z=262.1 (M+1), r.t.=3.28 mins. $^1$H NMR (400 MHz; d$_6$-DMSO) δ 6.93-6.86 (3H, m), 4.85 (1H, s), 3.45-3.36 (2H, m), 2.86 (3H, s).

8B) 4-Methyl-6-trifluoromethyl-3,4-dihydro-2h-benzo[1,4]oxazine-2-carboxylic acid [(r)-1-(2-fluoro-4-methanesulfonylamino-5-methylphenyl)ethylamide To a vial containing 4-methyl-6-trifluoromethyl-3,4-dihydro-2H-benzo[1,4]oxazine-2-carboxylic acid (39 mg, 0.15 mmol) was added a solution of HATU (62 mg, 0.16 mmol), DIPEA (54 μl, 0.32 mmol) and DMAP (1.5 mg, 0.012 mmol) in anhydrous DMF (1.5 mL). After stirring for 5 minutes, a solution of N-[4-((R)-1-aminoethyl)-5-fluoro-2-methylphenyl]methanesulfonamide hydrochloride (46 mg, 0.16 mmol) and DIPEA (27 μl, 0.16 mmol) in anhydrous DMF (1 mL) was added. The reaction was stirred at room temperature overnight, then poured into saturated NaHCO$_3$ solution (30 mL) and extracted with EtOAc (3×30 mL). The combined organics were washed with brine (3×30 mL), dried (MgSO$_4$), filtered and concentrated. Flash chromatography (0 to 100% EtOAc in hexanes) gave the title compound (34 mg, 45%) as a solid. m/z=490.4 (M+1), r.t.=3.65 mins $^1$H NMR (400 MHz; CDCl$_3$) δ 7.21-7.12 (1H, m), 6.99-6.96 (2H, m), 6.88-6.83 (2H, m), 6.13 (1H, d), 5.27-5.14 (1H, m), 4.81-4.70 (1H, m), 3.59-3.48 (1H, m), 3.39-3.34 (1H, m), 3.05 (3H, d), 2.91 (3H, d), 1.53 (3H, d), 1.49 (3H, d).

EXAMPLE 8

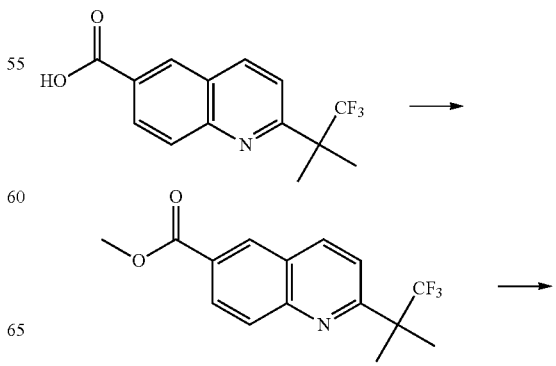

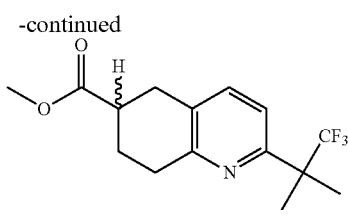

Methyl 2-(1,1,1-trifluoro-2-methylpropan-2-yl)quinoline-6-carboxylate and Methyl 2-(1,1,1-trifluoro-2-methylpropan-2-yl)-5,6,7,8-tetrahydroquinoline-6-carboxylate Methanolic HCl, prepared from methanol (8 mL) and acetyl chloride (1.1 mL, 15 mmol, 3 equiv), was charged to a 30 mL pressure vessel containing 2-(2,2,2-trifluoro-1,1-dimethyl-ethyl)-quinoline-6-carboxylic acid (1.42 g, 5.00 mmol), and the mixture placed in an oil bath at about 60° C. After 1.6 h the mixture was removed from the heat and concentrated to afford the quinoline methyl ester (assumed 5.0 mmol) as a solid, which was used directly in the next step.

A 250 mL flask was charged with the crude methyl ester (assumed 5.00 mmol), platinum dioxide monohydrate (110 mg, 0.50 mmol, 10 mol %) and trifluoroacetic acid (20 mL), then evacuated and flushed with hydrogen 3 times. The mixture was placed in an oil bath at 60° C. and hydrogenated for 14.5 h. The mixture was diluted with water (20 mL), poured into 2M Na$_2$CO$_3$ (170 mL), and extracted with DCM (2×50 mL). The combined organic layers were dried (MgSO$_4$), filtered and concentrated to a yellow oil, which was absorbed on silica. Chromatography on silica (0-10% EtOAc/hexane) afforded the pyridyl ester (0.98 g, 65%) as an oil. $^1$H NMR (400 MHz, CDCl$_3$) δ 9.22 (d, J=8.1 Hz, 1H), 7.48 (d, J=8.1 Hz, 1H), 3.74 (s, 3H), 3.08-2.88 (m, 4H), 2.82-2.72 (m, 1H), 2.36-2.26 (m, 1H), 2.02-1.92 (m, 1H), 1.58 (s, 6H). m/z=302.0 (M+H)$^+$.

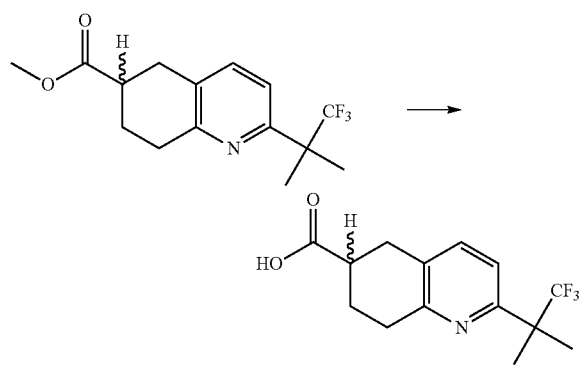

2-(1,1,1-Trifluoro-2-methylpropan-2-yl)-5,6,7,8-tetrahydroquinoline-6-carboxylic acid A solution of methyl 2-(1,1,1-trifluoro-2-methylpropan-2-yl)-5,6,7,8-tetrahydroquinoline-6-carboxylate (0.97 g, 3.2 mmol) in methanol (20 mL) was treated with 1 M aqueous sodium hydroxide (6 mL, 2 equiv), and the mixture was heated to reflux. After 1.5 h the cooled mixture was diluted with water. (40 mL), adjusted to pH 6 with H$_3$PO$_4$, and extracted with DCM (3×20 mL). The combined organic layers were dried (Na$_2$SO$_4$), filtered and concentrated to a solid (0.76 g, 82%). $^1$H NMR (400 MHz, DMSO-d$_6$) δ 12.34 (br s, 1H), 7.55 (d, J=8.1 Hz, 1H), 7.41 (d, J=8.1 Hz, 1H), 2.99-2.83 (m, 4H), 2.77-2.69 (m, 1H), 2.19-2.11 (m, 1H), 1.91-1.81 (m, 1H), 1.54 (s, 6H); m/z=288.4 (M+H)$^+$.

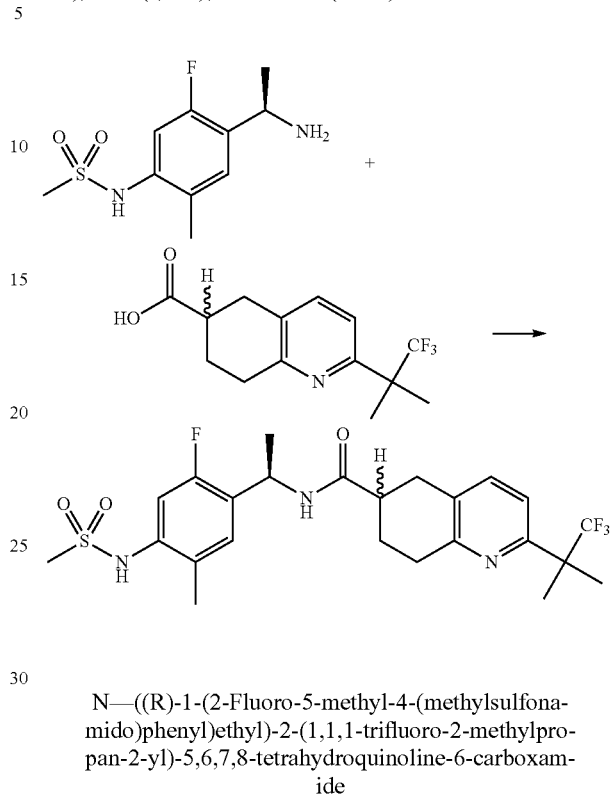

N—((R)-1-(2-Fluoro-5-methyl-4-(methylsulfonamido)phenyl)ethyl)-2-(1,1,1-trifluoro-2-methylpropan-2-yl)-5,6,7,8-tetrahydroquinoline-6-carboxamide A solution of N,N,N',N'-tetramethyl-O-(7-azabenzotriazol-1-yl)uronium hexafluorophosphate (19.8 mg, 0.0522 mmol) and N,N-diisopropylethylamine (28 uL, 0.16 mmol) in N-methylpyrrolidinone (300 uL) was added to (R)-2-(1,1,1-trifluoro-2-methylpropan-2-yl)-5,6,7,8-tetrahydroquinoline-6-carboxylic acid (15 mg, 0.052 mmol) in a 2 mL vial, and the mixture stirred at room temperature for 1 h, before a solution of (R)—N-(4-(1-aminoethyl)-5-fluoro-2-methylphenyl)methanesulfonamide hydrochloride (18 mg, 0.063 mmol) in N-methylpyrrolidinone (200 uL) was added. After 18 h the mixture was filtered and purified by reverse-phase HPLC (30-75% MeCN in 10 mM Et$_2$NH/H$_2$O) to afford the amide as a solid (12.3 mg, 46%). $^1$H NMR (400 MHz, DMSO-d$_6$) δ 9.08 (s, 1H), 8.41 (app dd, J=7.7, 12.0 Hz, 1H), 7.53 (app dd, J=3.3, 8.1 Hz, 1H), 7.35 (d, J=8.1 Hz, 1H), 7.22 (d, J=8.5 Hz, 1H), 7.07 (d, J=11.6 Hz, 1H), 5.09 (app hextet, J=7.3 Hz, 1H), 3.01 (s, 3H), 2.92-2.78 (m, 4H), 2.71-2.61 (m, 1H), 2.26 (s, 3H), 2.06-1.97 (m, 1H), 1.87-1.69 (m, 1H), 1.53 (s, 3H), 1.35 (d, J=7.1 Hz, 3H); m/z=516.3 (M+H)$^+$.

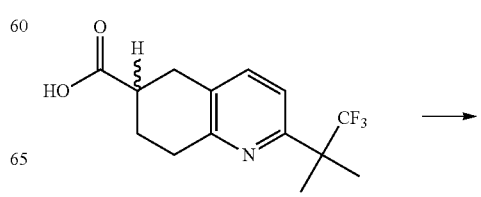

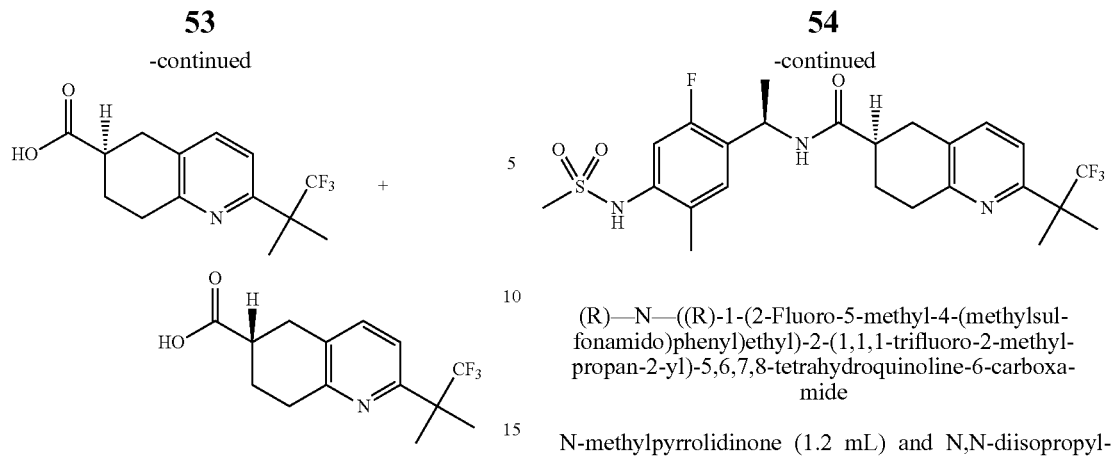

(R)-2-(1,1,1-trifluoro-2-methylpropan-2-yl)-5,6,7,8-tetrahydroquinoline-6-carboxylic acid (3B) and (S)-2-(1,1,1-trifluoro-2-methylpropan-2-yl)-5,6,7,8-tetrahydroquinoline-6-carboxylic acid Separation by chiral HPLC: 2-(1,1,1-trifluoro-2-methylpropan-2-yl)-5,6,7,8-tetrahydroquinoline-6-carboxylic acid (0.720 g) was dissolved in 1/1 IPA/hexane (8 mL). 1100 uL injections were separated on a ChiralPak AD-H 5 um 250×20 mm ID at 0° C. eluting with 0.1% TFA in 96/4 hexane/IPA at 20 mL/min. Peaks eluted at 6.3 and 7.9 min, with UV monitoring at 230 nm. The solutions from the chiral separation were concentrated and each solid was separately dissolved in 20/1 DCM/MeOH (40 mL), and washed with 1 M pH 6 phosphate buffer (30 mL). The aqueous layers were back-extracted with DCM (2×15 mL), and the combined organic layers were dried ($Na_2SO_4$), filtered and concentrated to afford the resolved acids, each as white solids (tentatively identified as (R)-(303 mg, 84%) and (S)- (292 mg, 81%) respectively. Analytical determination of ee: ChiralPak AD-H 250×4.6 mm ID, 5 um, 0.1% TFA in 96/4 hexane/IPA at 1 mL/min at ambient temperature, with UV analysis at 240 nm. Enantiomers eluted at 5.7 and 6.4 min, each with >99.5% ee and were assigned (R)- and (S)-respectively, based on an X-ray structure of the 4-bromophenyl anilide derivative of the first-eluting acid.

EXAMPLE 9

(R)—N—((R)-1-(2-Fluoro-5-methyl-4-(methylsulfonamido)phenyl)ethyl)-2-(1,1,1-trifluoro-2-methylpropan-2-yl)-5,6,7,8-tetrahydroquinoline-6-carboxamide N-methylpyrrolidinone (1.2 mL) and N,N-diisopropylethylamine (87 uL, 0.50 mmol) were added to (R)-2-(1,1,1-trifluoro-2-methylpropan-2-yl)-5,6,7,8-tetrahydroquinoline-6-carboxylic acid (47 mg, 0.16 mmol) and N,N,N',N'-tetramethyl-O-(7-azabenzotriazol-1-yl)uronium hexafluorophosphate (75 mg, 0.20 mmol) in a 4 mL vial, and the mixture stirred at room temperature for 10 min, before a solution of (R)—N-(4-(1-aminoethyl)-5-fluoro-2-methylphenyl)methanesulfonamide hydrochloride (55 mg, 0.19 mmol) in N-methylpyrrolidinone (0.5 mL) was added. After 30 min the mixture was filtered and purified by reverse-phase HPLC (10-75% MeCN in 10 mM $Et_2NH/H_2O$) to afford the amide as a solid (50 mg, 58%). $^1$H NMR (400 MHz, DMSO-$d_6$) δ 9.12 (br s, 1H), 8.39 (d, J=8.1 Hz, 1H), 7.53 (d, J=8.1 Hz, 1H), 7.34 (d, J=8.1 Hz, 1H), 7.22 (d, J=8.6 Hz, 1H), 7.06 (d, J=11.7 Hz, 1H), 5.10 (app pentet, J=7.2 Hz, 1H), 3.00 (s, 3H), 2.93-2.76 (m, 4H), 2.68-2.59 (m, 1H), 2.25, (s, 3H), 2.09-2.03 (m, 1H), 1.88-1.76 (m, 1H), 1.54 (s, 3H), 1.35 (d, J=7.0 Hz, 3H); m/z=515.8 (M+H)$^+$.

EXAMPLE 10

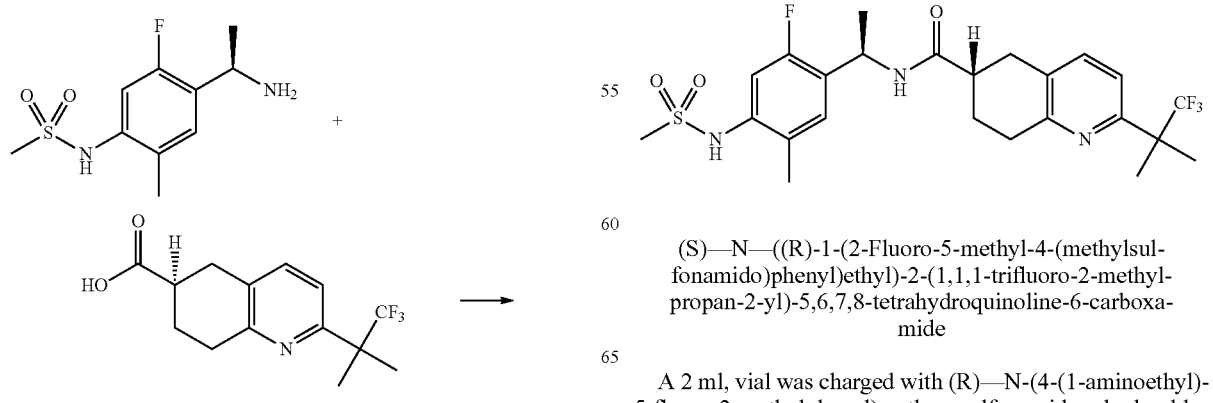

(S)—N—((R)-1-(2-Fluoro-5-methyl-4-(methylsulfonamido)phenyl)ethyl)-2-(1,1,1-trifluoro-2-methylpropan-2-yl)-5,6,7,8-tetrahydroquinoline-6-carboxamide A 2 ml vial was charged with (R)—N-(4-(1-aminoethyl)-5-fluoro-2-methylphenyl)methanesulfonamide hydrochloride (51 mg, 0.18 mmol), (S)-2-(1,1,1-trifluoro-2-methylpropan-2-yl)-5,6,7,8-tetrahydroquinoline-6-carboxylic acid (47 mg, 0.16 mmol) and N,N-diisopropylethylamine (110 uL, 0.65 mmol) and N-methylpyrrolidinone (0.8 mL). A solution of N,N,N',N'-Tetramethyl-O-(7-azabenzotriazol-1-yl)uronium Hexafluorophosphate (75 mg, 0.20 mmol) in N-methylpyrrolidinone (0.4 mL) was added and the resulting mixture was stirred at room temperature. After 30 min the mixture was filtered and purified by reverse-phase HPLC (10-75% MeCN in 10 mM $Et_2NH/H_2O$) to afford the amide as a solid (72 mg, 85%). The sample was dissolved in hot 2/3 IPA/hexane (5 mL). 1.2 mL injections were separated on a ChiralPak AD-H 5 um, 250×20 mm column, eluting with 85/15/0.03 hexane/IPA/$Et_2NH$ at 20 mL/min. Peaks eluted at 7.5 and 8.7 min, with UV monitoring at 254 and 230 nm. The major isomer, eluting at 8.7 min was concentrated to afford the amide as fine plates (47 mg, 56%). $^1H$ NMR (400 MHz, DMSO-$d_6$) δ 9.19 (s, 1H), 8.41 (d, J=7.6 Hz, 1H), 7.53 (d, J=8.1 Hz, 1H), 7.35 (d, J=8.1 Hz, 1H), 7.22 (d, J=8.5 Hz, 1H), 7.07 (d, J=11.6 Hz, 1H), 5.09 (app pentet, J=7.2 Hz, 1H), 3.01 (s, 3H), 2.92-2.78 (m, 4H), 2.71-2.61 (m, 1H), 2.26 (s, 3H), 2.06-1.97 (m, 1H), 1.82-1.69 (m, 1H), 1.53 (s, 3H), 1.35 (d, J=7.1 Hz, 3H); m/z=516.2 (M+H)$^+$.

EXAMPLE 11

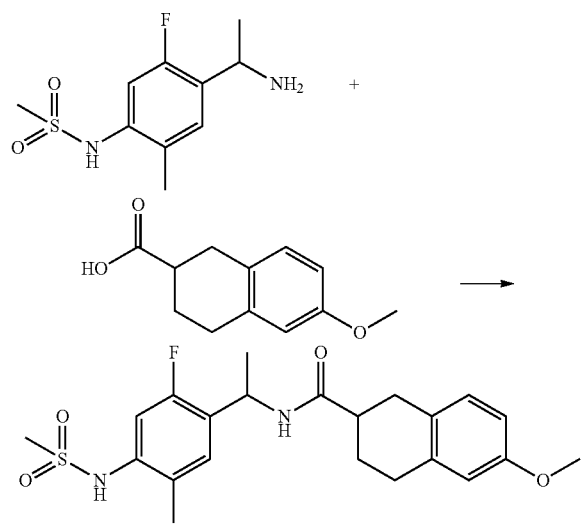

6-Methoxy-1,2,3,4-tetrahydro-naphthalene-2-carboxylic acid [1-(2-fluoro-4-methanesulfonylamino-5-methyl-phenyl)-ethyl]-amide In a 20 ml vial, N-[4-(1-amino-ethyl)-5-fluoro-2-methyl-phenyl]-methanesulfonamide (100 mg, 0.4 mmol), 6-methoxy-1,2,3,4-tetrahydro-naphthalene-2-carboxylic acid (100 mg, 0.49 mmol) and N,N,N',N'-tetramethyl-O-(7-azabenzotriazol-1-yl)uronium hexafluorophosphate (380 mg, 1.0 mmol) were dissolved in N,N-dimethylformamide (8 mL). N,N-Diisopropylethylamine (400 uL, 2.0 mmol) was added while stirring. The reaction was heated for 1 hour at 50° C. After cooling the reaction to room temperature, saturated NaHCO$_3$ solution (20 ml) was poured into the vial and extracted with DCM (3×30 ml). The combined organics was washed once with brine (40 ml), dried over NaSO$_4$, filtered and concentrated. Purification by HPLC yielded a solid (63.1 mg, 30%). m/z=435.2 (M+1). $^1$H-NMR (400 MHz, DMSO-$d_6$) δ 9.24 (s, 1H), 8.34 (t, 1H, J=7.60 Hz), 7.21 (d, 1H, J=8.67 Hz), 7.06 (d, 1H, J=11.56 Hz), 7.00-6.97 (m, 1H), 6.68-6.62 (m, 2H), 5.11-5.06 (m, 1H), 3.68 (s, 3H), 3.00 (d, 3H-1, J=0.97 Hz), 2.77-2.68 (m, 4H), 2.57-2.51 (m, 1H), 2.25 (s, 3H), 1.95-1.88 (m, 1H), 1.70-1.54 (m, 1H), 1.33 (d, 3H, J=7.13 Hz).

EXAMPLE 12

6-(tert-Butoxycarbonyl)quinoline 1-oxide was prepared according to the method of: Bertinato, P; Couturier, M A; Hamanaka, E S; Ewing, M D; Robinson, R P, Jr.; Tickner, D L. "*Preparation of substituted quinolines as MTP/Apo-B secretion inhibitors for treating obesity and associated conditions*" PCT Int. Appl. (2005), WO 2005080373 A1 20050901 CAN 143:248301 AN 2005:962242

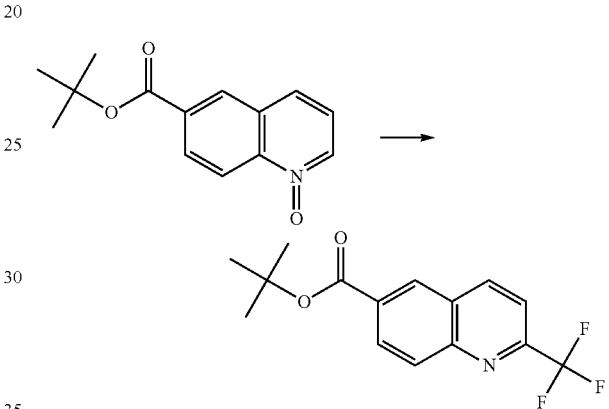

tert-Butyl 2-(trifluoromethyl)quinoline-6-carboxylate

To a solution of 6-(tert-butoxycarbonyl)quinoline 1-oxide (6 g, 20 mmol) and trimethyl(trifluoromethyl)silane (6.15 mL, 41.6 mmol) in THF (100 mL) at 0° C. was added cesium fluoride (400 mg, 2.63 mmol) and the mixture was allowed to warm to room temperature. After 24 h, additional trimethyl (trifluoromethyl)silane (4.70 mL, 31.8 mmol) and cesium fluoride (400 mg) were added and the mixture was aged for an additional 3 days. The mixture was concentrated and the residue taken up in EtOAc (150 mL), washed with sat. aq. NaHCO$_3$ (2×50 mL), brine (2×30 mL), dried (MgSO$_4$), filtered and solvent removed under reduced pressure to give a dark brown oil which was purified by column chromatography eluting with EtOAc/Heptane (70:30) to afford the quinoline oxide (5.4 g, 80%) as a solid. $^1$H NMR (400 MHz, DMSO-$d_6$) δ 8.97 (d, J=8.7 Hz, 1H), 8.80 (d, J=1.8 Hz, 1H), 8.32 (dd, J=1.8, 8.9 Hz, 1H), 8.27 (d, J=8.9 Hz, 1H), 8.10 (d, J=8.7 Hz, 1H), 1.62 (s, 9H); m/z=298.4 (M+H)$^+$.

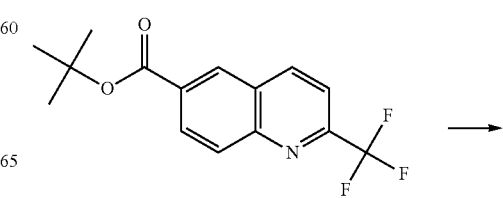

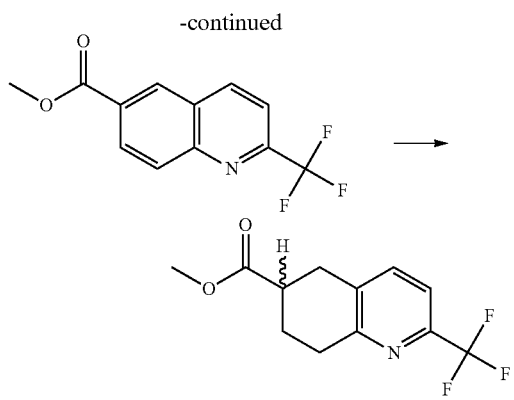

Methyl 2-(trifluoromethyl)quinoline-6-carboxylate (10B) and methyl 2-(trifluoromethyl)-5,6,7,8-tetrahydroquinoline-6-carboxylate Methanolic HCl, prepared from methanol (7 mL) and acetyl chloride (0.80 mL, 11 mmol), was charged to a 30 mL pressure vessel containing tert-butyl 2-(trifluoromethyl)quinoline-6-carboxylate (234 mg, 0.79 mmol), and the mixture placed in an oil bath at 80° C. for 2 h. The mixture was then concentrated to afford the methyl ester as a yellow solid (202 mg, assumed 0.79 mmol), which was used directly in the next step.

A 25 mL flask was charged with the crude methyl ester (assumed 0.79 mmol), platinum dioxide monohydrate (18 mg, 0.079 mmol, 10 mol %) and trifluoroacetic acid (3 mL), then evacuated and flushed with hydrogen 3 times. The mixture was placed in an oil bath at 60° C. and hydrogenated for 4 h. The mixture was diluted with water (20 mL), poured into 2M $Na_2CO_3$ (40 mL), and extracted with DCM (2×30 mL). The combined organic layers were dried ($Na_2SO_4$), filtered and concentrated to an orange oil, which was absorbed on silica. Chromatography on silica (0-35% EtOAc/hexane) followed by reverse-phase HPLC (50-98% MeCN in 10 mM $Et_2NH/H_2O$) afforded the trifluoromethyl-tetrahydroquinoline as a solid (6 mg, 3%); $^1H$ NMR (400 MHz, $CDCl_3$) δ 7.57 (d, J=7.9 Hz, 1H), 7.45 (d, J=7.9 Hz, 1H), 3.75 (s, 3H), 3.17-2.97 (m, 4H), 2.88-2.79 (m, 1H), 2.38-2.29 (m, 1H), 2.09-1.98 (m, 1H); m/z=260.0 $(M+H)^+$.

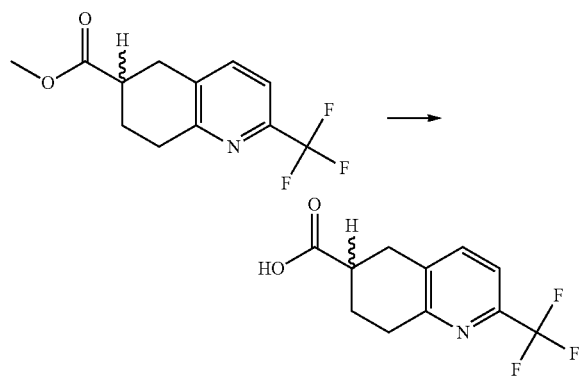

2-(Trifluoromethyl)-5,6,7,8-tetrahydroquinoline-6-carboxylic acid

A 25 mL flask was charged with methyl 2-(trifluoromethyl)-5,6,7,8-tetrahydroquinoline-6-carboxylate (6 mg, 0.02 mmol), methanol (3 mL) and 1 M aqueous sodium hydroxide (0.23 mL, 10 equiv), and the mixture heated in an oil bath at 90° C. The mixture was removed from the heat after 1.5 h, diluted with 1M $NaH_2PO_4$ (10 mL), buffered to pH 3 with 1M $H_3PO_4$, then extracted with DCM (3×20 mL). The combined organic extracts were dried ($Na_2SO_4$), filtered, and concentrated to afford the acid as a white solid (6 mg, 100%). $^1H$ NMR (400 MHz, $CDCl_3$) δ 7.59 (d, J=8.0 Hz, 1H), 7.46 (d, J=8.0 Hz, 1H), 3.21-3.02 (m, 4H), 2.95-2.84 (m, 1H), 2.42-2.32 (m, 1H), 2.14-2.03 (m, 1H), 1.10 (br s, 11-1); m/z=246.4 $(M+H)^f$.

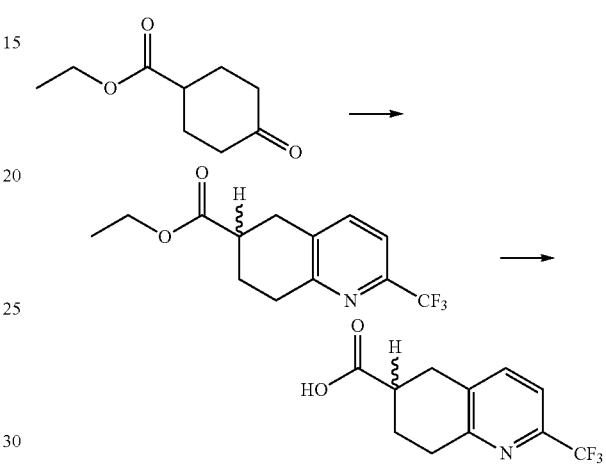

Alternative Preparation of 2-(trifluoromethyl)-5,6,7,8-tetrahydroquinoline-6-carboxylic acid a. Ethyl 2-(trifluoromethyl)-5,6,7,8-tetrahydroquinoline-6-carboxylate

A mixture of ethyl 4-oxocyclohexanecarboxylate (3.0 g, 17 mmol), pyrrolidine (3.6 mL, 43 mmol, 2.5 equiv.) and toluene (50 mL) was heated to reflux with azeotropic removal of water. After 17 h the reaction was judged complete, and the cooled mixture was concentrated. The residue was taken up in ether (100 mL), dried ($MgSO_4$), filtered and concentrated to afford crude enamine as an oil (3.97 g). The crude enamine (assumed 17 mmol) was dissolved in 1,4-dioxane (50 mL), and the solution cooled to 10° C., before a solution of 4-ethoxy-1,1,1-trifluorobut-3-en-2-one (3.5 g, 21 mmol) in 1,4-dioxane (10 mL) was added dropwise over 10 min to the yellow suspension, which rapidly clarified and darkened to a deep red-brown. The mixture was allowed to warm to room temperature overnight. After 18 h ammonium acetate (2.7 g, 35 mmol, 2 equiv.) was added, and the mixture heated to reflux for 2.5 h. The mixture was concentrated to an oil. Chromatography on silica (0-20% EtOAc/hexane) afforded the desired trifluoromethylpyridine as an oil (1.27 g, 27%). $^1H$ NMR (400 MHz, $CDCl_3$) [δ] 7.57 (d, J=7.9 Hz, 1JH), 7.44 (d, J=7.9 Hz, 1H), 4.20 (q, J=7.2 Hz, 2H), 3.18-2.96 (m, 4H), 2.85-2.76 (m, 1H), 2.48-2.39 (M, 1H), 2.09-1.97 (m, 1H), 1.29 (t, J=7.2 Hz, 3H); m/z=274.2 $(M+H)^+$.

b. 2-(Trifluoromethyl)-5,6,7,8-tetrahydroquinoline-6-carboxylic acid

A mixture of ethyl 2-(trifluoromethyl)-5,6,7,8-tetrahydroquinoline-6-carboxylate (0.47 g, 1.7 mmol), 1 M aqueous sodium hydroxide (3.4 mL, 3.4 mmol, 2 equiv.) and methanol (10 mL), was heated at reflux for 16 h. The mixture was concentrated to remove MeOH, diluted with 1M aqueous NaH₂PO₄ (15 mL) and buffered to pH 3 with 1M H₃PO₄, depositing a voluminous precipitate. The mixture was extracted with DCM (3×30 mL), and the combined organic layers were dried (Na₂SO₄), filtered and concentrated. The solid residue was purified by reverse-phase HPLC (40-55% acetonitrile in 0.1% HCO₂H/H₂O). The combined HPLC fractions were concentrated to remove acetonitrile, buffered with 1M NaH₂PO₄ (10 mL) and extracted with DCM (3×30 mL). The combined organic layers were dried (Na₂SO₄), filtered and concentrated to afford the acid as a solid (324 mg, 77%). $^1$H NMR (400 MHz, DMSO-d$_6$) [δ] 12.45 (s, 1H), 7.82 (d, J=7.9 Hz, 1H), 7.63 (d, J=7.9 Hz, 1H), 3.12-2.86 (m, 4H), 2.83-2.76 (m, 1H), 2.22-2.14 (m, 1H), 1.97-1.86 (m, 1H); m/z=246.1 (M+H)$^+$.

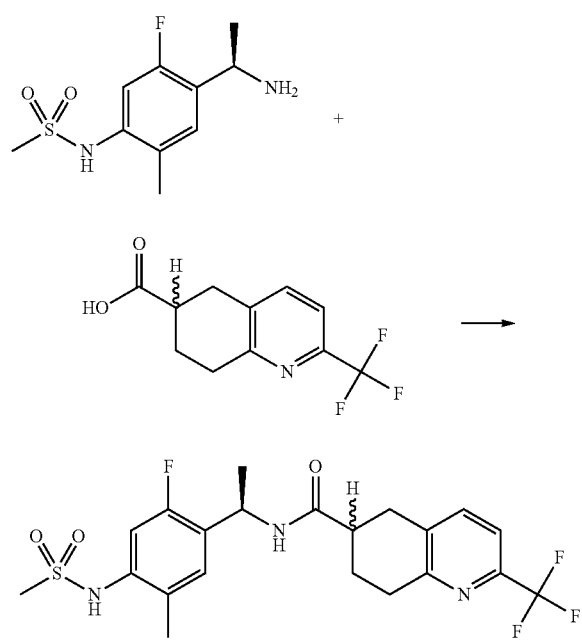

N—((R)-1-(2-Fluoro-5-methyl-4-(methylsulfonamido)phenyl)ethyl)-2-(trifluoromethyl)-5,6,7,8-tetrahydroquinoline-6-carboxamide A 2 mL vial was charged with (R)—N-(4-(1-aminoethyl)-5-fluoro-2-methylphenyl)methanesulfonamide hydrochloride (14 mg, 0.049 mmol) and N,N,N',N'-tetramethyl-O-(7-azabenzotriazol-1-yl)uronium hexafluorophosphate (17 mg, 0.044 mmol). A solution of 2-(trifluoromethyl)-5,6,7,8-tetrahydroquinoline-6-carboxylic acid (6.0 mg, 0.024 mmol) and N,N-diisopropylethylamine (21 uL, 0.12 mmol) in N-methylpyrrolidinone (0.4 mL, 4 mmol) was added, and the mixture stirred to dissolution. After 40 min the mixture was filtered and purified by reverse-phase HPLC (10-75% MeCN in 10 mM Et₂NH/H₂O) to afford the amide as a solid (8.4 mg, 72%). $^1$H NMR (400 MHz, CD₃OD) δ 7.73 (app t, J=8.3 Hz, 1H), 7.53 (dd, J=3.8, 8.0 Hz, 1H), 7.23 (d, J=8.3 Hz, 1H), 7.14 (dd, J=1.4, 11.7 Hz, 1H), 5.19 (app pentet, J=7.0 Hz, 1H), 3.17-2.94 (m, 4H), 2.98 (s, 3H), 2.82-2.71 (m, 1H), 2.32 (s, 3H), 2.23-2.12 (m, 1H), 2.07-1.89 (m, 1H), 1.47 (d, J=7.0 Hz, 3H); m/z=474.4 (M+H)$^+$.

EXAMPLE 13

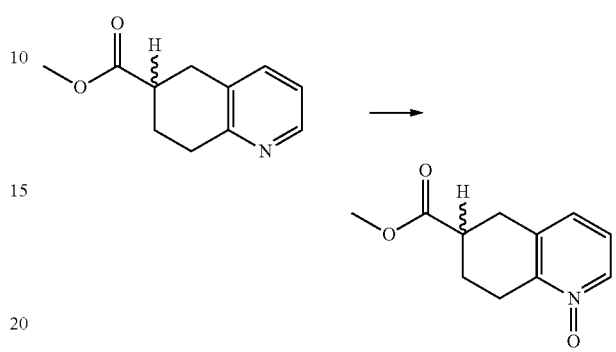

6-(Methoxycarbonyl)-5,6,7,8-tetrahydroquinoline 1-oxide

A 1-L flask was charged with methyl 5,6,7,8-tetrahydroquinoline-6-carboxylate (12.53 g, 65.52 mmol), chloroform (400 mL) and m-chloroperbenzoic acid (22.6 g, 91.7 mmol). The resulting solution was stirred at room temperature for 1 hour then dimethyl sulfoxide (2.8 mL, 39 mmol) was added to quench any remaining m-chloroperbenzoic acid and stirred at room temperature for 30 minutes. The mixture was poured into 2M Na₂CO₃ (400 mL). The aqueous layer was extracted with CHCl₃ (3×200 mL), dried (Na₂SO₄), filtered and concentrated to afford a white solid (16.67 g). Chromatography on silica (0-15% MeOH in DCM) produced an off white solid (13.90 g, greater than theoretical), which was carried forward without additional purification. m/z=208.3 (M+H)$^+$. NMR (400 MHz, CDCl₃) δ 8.16 (d with fine str., J=5.8 Hz, 1H), 7.10-7.03 (m, 2H), 3.74 (s, 3H), 3.20 (app dt, J=13.9, 5.6 Hz, 1H), 3.11-2.99 (m, 2H), 2.93-2.82 (m, 1H), 2.79-2.71 (m, 1H), 2.39-2.30 (m, 1H), 2.05-1.92 (m, 1H).

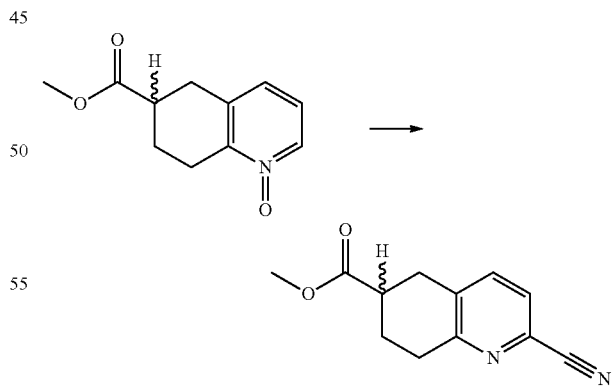

Methyl 2-cyano-5,6,7,8-tetrahydroquinoline-6-carboxylate

A 150 mL pressure vessel was charged with 6-(methoxycarbonyl)-5,6,7,8-tetrahydroquinoline 1-oxide (13.58 g, 65.52 mmol), triethylamine (18 mL, 130 mmol), trimethylsilyl cyanide (26.2 mL, 196 mmol) and acetonitrile (33 mL), and the mixture was heated at 130° C. for 21 h. Slowly quenched reaction into 2M Na$_2$CO$_3$ (250 mL) then diluted with DCM (500 mL). The mixture was filtered through celite and the filter cake washed with DCM (2×200 mL) and water (100 mL). The aqueous layer was extracted with additional DCM (100 mL×2). The combined organics was washed with 1M Na$_2$CO$_3$ (200 mL) and 1 M NaH$_2$PO$_4$ (150 mL×2), dried (Na$_2$SO$_4$), filtered and evaporated. The residue was purified by silica chromatography (100% hexanes to 100% DCM to 20% MeOH in DCM). Additional purification by silica chromatography (0-100% EtOAc in hexanes) yielded a pale yellow solid (3.32 g, 23%). m/z=217.5 (M+H)$^+$. $^1$H NMR (400 MHz, CDCl$_3$) δ 7.54 (d, J=7.9 Hz, 1H), 7.47 (d, J=7.9 Hz, 1H), 3.74 (s, 3H), 3.18-2.94 (m, 4H), 2.88-2.78 (m, 1H), 2.35-2.26 (m, 1H), 2.09-1.97 (m, 1H).

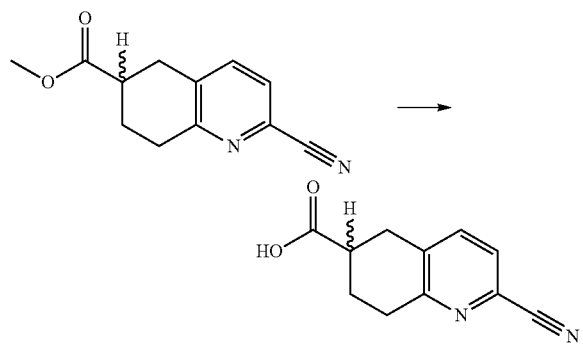

2-Cyano-5,6,7,8-tetrahydroquinoline-6-carboxylic acid

A mixture of lithium iodide (10.3 g, 77.0 mmol), methyl 2-cyano-5,6,7,8-tetrahydroquinoline-6-carboxylate (3.32 g, 15.4 mmol) and pyridine (39 mL, 480 mmol) was divided evenly between two 35 mL vials and the mixtures submitted to microwave irradiation for 4 hr at 130° C. The reactions were combined and concentrated to ~15 mL. The residue was diluted with water (50 mL) and DCM (200 mL) and 1M citric acid (150 mL) was added until a pH of 4 was attained. The aqueous was extracted with additional DCM (200 mL) and the combined organics was washed with 0.25 M citric acid (150 mL). The citric acid wash was back extracted with DCM (50 mL) and the combined organics were dried ((Na$_2$SO$_4$), filtered and evaporated. The residue was dissolved in DCM (200 mL) and washed with 0.5 M citric acid (50 mL×2). Each citric acid wash was back extracted with DCM (25 mL) and the combined organics dried (Na$_2$SO$_4$), filtered and evaporated to obtain a yellow solid (2.54 g, 82%). m/z=201.2 (M−H)$^−$. $^1$H NMR (400 MHz, DMSO-d6) δ 12.47 (br s, 1H), 7.80 (d, J=8.1 Hz, 1H), 7.77 (d, J=8.1 Hz, 1H), 3.12-2.84 (m, 4H), 2.83-2.74 (m, 1H), 2.22-2.13 (m, 1H), 1.94-1.83 (m, 1H).

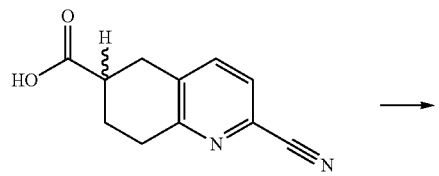

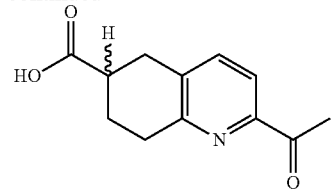

2-Acetyl-5,6,7,8-tetrahydroquinoline-6-carboxylic acid

To a 250 mL flak was added 2-cyano-5,6,7,8-tetrahydroquinoline-6-carboxylic acid (2.50 g, 12.4 mmol) and tetrahydrofuran (52 mL, 640 mmol). The system was purged with nitrogen and cooled to 0° C. 3M of methylmagnesium chloride in tetrahydrofuran (11.1 mL, 37.1 mmol) was added dropwise over 5 minutes. The mixture was stirred at 0° C. for 5 minutes then allowed to warm to room temperature. After a total of 2.5 hours the reaction was carefully quenched by dropwise addition of 1 M citric acid until a pH of 3.5 was obtained (~50 mL). The mixture was extracted with EtOAc (200 mL then 100 mL), and the aqueous layer was, saturated with salt and extracted with 3:1 CHCl$_3$/IPA (2×100 mL). The combined organics was dried (Na$_2$SO$_4$), filtered and evaporated to obtain an orange solid (5.39 g). The residue was purified by silica chromatography [0-100% EtOAc/AcOH (200/1) in hexanes] to obtain a light yellow powder (2.27 g, 84%). m/z=220.4 (M+H)$^+$, m/z=218.3 (M−H)$^−$. $^1$H NMR (400 MHz, CDCl$_3$) δ 12.43 (br s, 1H), 7.71 (s, 2H), 3.10-2.93 (m, 4H), 2.82-2.74 (m, 1H), 2.23-2.06 (m, 1H), 1.97-1.85 (m, 1H).

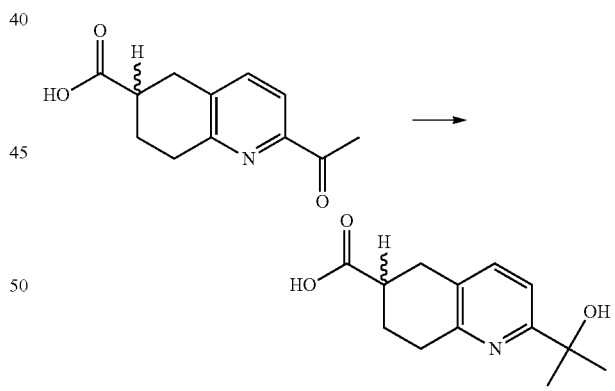

2-(2-hydroxypropan-2-yl)-5,6,7,8-tetrahydroquinoline-6-carboxylic acid

To a 25 mL flask was added 2-acetyl-5,6,7,8-tetrahydroquinoline-6-carboxylic acid (146 mg, 0.667 mmol) and tetrahydrofuran (2.7 mL). The system was purged with nitrogen and cooled to 0° C. 3M of methylmagnesium chloride in tetrahydrofuran (0.598 mL, 2.00 mmol) was added dropwise over 3 minutes. The mixture was stirred at 0° C. for 5 minutes then allowed to warm to room temperature. Additional THF (5 mL) was added and the mixture was sonicated for 1 minute to break up solids. After a total of 2 hours the reaction was carefully quenched by dropwise addition of 1M NaH$_2$PO$_4$ (10 mL). The mixture was diluted with DCM (10 mL) and citric acid (0.5 mL) was added to obtain a pH of 4. The layers were separated and the aqueous was extracted with 3:1 DCM/THF (10 mL) followed by with 3:1 CHCl$_3$/IPA (15 mL×2), dried (Na$_2$SO$_4$), filtered and evaporated to obtain a reddish foam (160 mg, theoretical yield), which was used directly in the next step. m/z=236.2 (M+H)$^+$. $^1$H NMR (400 MHz, CD$_3$OD) δ 7.55 (d, J=8.1 Hz, 1H), 7.39 (d, J=8.1 Hz, 1H), 3.10-2.90 (m, 4H), 2.85-2.74 (m, 1H), 2.32-2.25 (m, 1H), 2.06-1.95 (m, 1H), 1.51 (s, 6H).

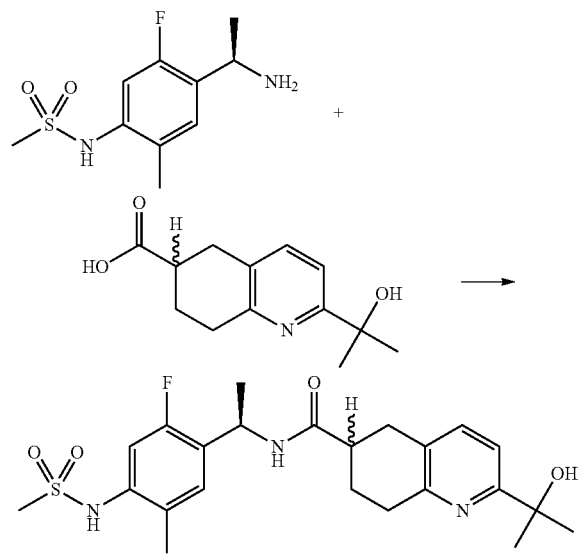

N—((R)-1-(2-fluoro-5-methyl-4-(methylsulfona-mido)phenyl)ethyl)-2-(2-hydroxypropan-2-yl)-5,6,7,8-tetrahydroquinoline-6-carboxamide A 4-mL vial was charged with (R)—N-(4-(1-aminoethyl)-5-fluoro-2-methylphenyl)methanesulfonamide hydrochloride (95 mg, 0.34 mmol) and N,N,N',N'-tetramethyl-O-(7-azabenzotriazol-1-yl)uronium hexafluorophosphate (130 mg, 0.34 mmol). A solution of 2-(2-hydroxypropan-2-yl)-5,6,7,8-tetrahydroquinoline-6-carboxylic acid (66 mg, 0.28 mmol) and N,N-diisopropylethylamine (290 µL, 1.7 mmol) in N-methylpyrrolidinone (850 µL) was added and the mixture stirred at room temperature for 1 hour. The reaction was quenched with water (100 µL), filtered and purified by reverse-phase HPLC (10-75% MeCN in 10 mM Et$_2$NH/H$_2$O) to afford the amide as a light yellow solid (70 mg, 54%). Additional purification by silica chromatography was performed (0-100% EtOAc in hexanes) to obtain a white solid (45 mg, 35%). m/z=464.6 (M+H)$^+$. $^1$H NMR (400 MHz, DMSO-d6) δ 9.19 (br s, 1H), 8.41 (app dd J=7.8 Hz, J=11.0 Hz, 1H), 7.45 (app dd, J=3.0 Hz, J=8.0 Hz, 1H), 7.36 (app dd, J=1.5 Hz, J=8.0 Hz, 1H), 7.23 (d, J=8.5 Hz, 1H), 7.07 (d, J=11.5 Hz, 1H), 5.17-5.04 (m, 2H) 3.02 (s, 3H), 2.92-2.73 (m, 4H), 2.68-2.57 (m, 1H), 2.26 (s, 3H), 2.09-1.96 (m, 1H), 1.88-1.66 (m, 1H), 1.39 (s, 3H), 1.39 (s, 3H), 1.35 (d, J=7.0 Hz, 3H).

EXAMPLES 14 & 15

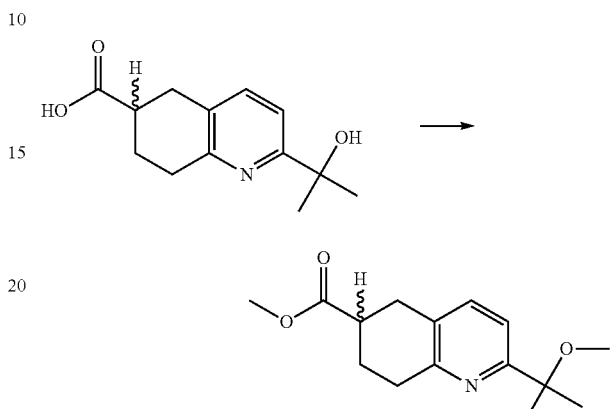

Methyl 2-(2-methoxypropan-2-yl)-5,6,7,8-tetrahydroquinoline-6-carboxylate

A 25 mL flask was charged with 2-(2-hydroxypropan-2-yl)-5,6,7,8-tetrahydroquinoline-6-carboxylic acid (78 mg, 0.33 mmol), N,N-dimethylformamide (3.3 mL, 43 mmol), K$_2$CO$_3$ (230 mg, 1.6 mmol) and methyl iodide (62 µL, 0.99 mmol) and the mixture stirred at room temperature for 40 hrs. The mixture was filtered and the filtrate was added to a cooled (0° C.) suspension of sodium hydride (40 mg, 0.99 mmol) in DMF (1 mL) and THF (1 mL), and the resulting mixture was stirred at room temperature for 20 minutes. Methyl iodide (41 µL, 0.66 mmol) in DMF (500 µL) was added dropwise and the resulting mixture stirred at room temperature for 20 hours. The reaction was carefully quenched by dropwise addition of 1M NaH$_2$PO$_4$ (4 mL) then diluted with brine (20 mL). Saturated NaHCO$_3$ was added until a pH of 8 was attained and the mixture was extracted with EtOAc (25 mL). The aqueous layer was diluted with additional brine (25 mL) and extracted with EtOAc (25 mL). The combined organics were washed with brine (3×50 mL), dried (Na$_2$SO$_4$), filtered and concentrated. The residue was purified by silica chromatography (0-100% EtOAc in hexanes) to obtained a colorless oil (16 mg, 18%). m/z=264.2 (M+H)$^+$. $^1$H NMR (400 MHz, CDCl$_3$) δ 7.38 (d, J=8.0 Hz, 1H), 7.28 (d, J=8.1 Hz, 1H), 3.74 (s, 3H), 3.15 (s, 3H), 3.08-2.87 (m, 4H), 2.83-2.73 (m, 1H), 2.36-2.24 (m, 1H), 2.03-1.90 (m, 1H), 1.53 (s, 6H).

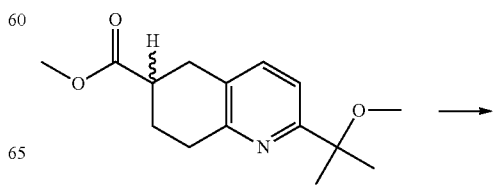

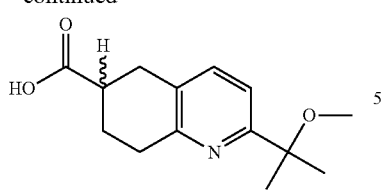

2-(2-methoxypropan-2-yl)-5,6,7,8-tetrahydroquinoline-6-carboxylic acid

A 4-mL vial with stir bar was charged with methyl 2-(2-methoxypropan-2-yl)-5,6,7,8-tetrahydroquinoline-6-carboxylate (16 mg, 0.061 mmol), methanol (450 μL) and 4M sodium hydroxide (150 μL, 0.61 mmol). The mixture was stirred at room temperature for 1 hour then quenched into 1M $NaH_2PO_4$ (2 mL) and 1M citric acid was added to obtain pH 4-5. The mixture was extracted with EtOAc (3 mL×3), dried ($Na_2SO_4$), filtered and evaporated to obtain a colorless oil (24 mg), which was used directly in the next step. m/z=250.3 $(M+H)^+$. $^1$H NMR (400 MHz; $CD_3OD$) δ 8.32 (d, J=8.3 Hz, 1H), 7.83 (d, J=8.3 Hz, 1H), 3.3.0 (s, 3H), 3.29-3.15 (m, 4H), 3.00-2.90 (m, 1H), 2.41-2.31 (m, 1H), 2.17-2.04 (m, 1H), 2.04 (s, 2H), 1.66 (s, 6H).

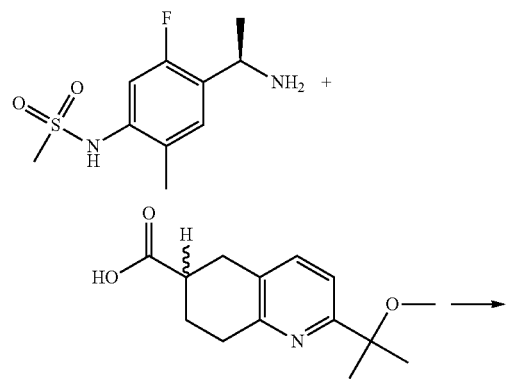

(S)—N—((R)-1-(2-fluoro-5-methyl-4-(methylsulfonamido)phenyl)ethyl)-2-(2-methoxypropan-2-yl)-5,6,7,8-tetrahydroquinoline-6-carboxamide (A, 15) and (R)—N—((R)-1-(2-fluoro-5-methyl-4-(methylsulfonamido)phenyl)ethyl)-2-(2-methoxypropan-2-yl)-5,6,7,8-tetrahydroquinoline-6-carboxamide (B, 14)

A 2-mL vial was charged with N-[4-((R)-1-Aminoethyl)-5-fluoro-2-methylphenyl]methanesulfonamide hydrochloride (86.2 mg, 0.305 mmol) and N,N,N',N'-tetramethyl-O-(7-azabenzotriazol-1-yl)uronium hexafluorophosphate (116 mg, 0.305 mmol). A solution of 2-(2-methoxypropan-2-yl)-5,6,7,8-tetrahydroquinoline-6-carboxylic acid.0.5[C6H8O7] (assumed 0.061 mmol) and N,N-diisopropylethylamine (74 μL, 0.43 mmol) in N-methylpyrrolidinone (300 μL) was added and the reaction was stirred at room temperature for 15 minutes. The reaction was quenched with water (100 μL), diluted with NMP (400 μL), filtered and purified by reverse-phase HPLC (10-75% MeCN in 10 mM $Et_2NH/H_2O$) to afford a mixture of A (19) and B (18) as a light yellow solid (14 mg, 48%). Additional reverse-phase HPLC (15-30% MeCN in 10 mM $Et_2NH/H_2O$) purification separated the diastereomers, tentatively assigned as (A, 15) (4.7 mg, 16%) and (B, 14) (6.0 mg, 21%) both as white solids. (A, 15) $^1$H NMR (400 MHz, $CD_3OD$) δ 7.47 (d, J=8.0 Hz, 1H), 7.28 (d, J=8.0 Hz, 1H), 7.23 (d, J=8.3 Hz, 1H), 7.13 (d, J=11.7 Hz, 1H), 5.20 (q, J=7.0 Hz, 1H) 3.11 (s, 3H), 2.98 (s, 3H), 3.07-2.79 (m, 4H), 2.74-2.63 (m, 1H), 2.31 (s, 3H), 2.20-2.10 (m, 1H), 2.02-1.87 (m, 1H), 1.51 (s, 3H), 1.50 (s, 3H), 1.47 (d, J=7.0 Hz, 3H); m/z=478.2 $(M+H)^+$.

(B, 14) $^1$H NMR (400 MHz, $CD_3OD$) δ 7.49 (d, J=8.0 Hz, 1H), 7.29 (d, J=8.0 Hz, 1H), 7.23 (d, J=8.3 Hz, 1H), 7.13 (d, J=11.7 Hz, 1H), 5.19 (q, J=7.0 Hz, 1H) 3.11 (s, 3H), 2.98 (s, 3H), 3.05-2.83 (m, 4H), 2.76-2.64 (m, 1H), 2.31 (s, 3H), 2.15-2.05 (m, 1H), 1.96-1.82 (m, 1H), 1.51 (s, 3H), 1.50 (s, 3H), 1.46 (d, J=7.0 Hz, 3H); m/z=478.1 $(M+H)^+$.

EXAMPLE 16

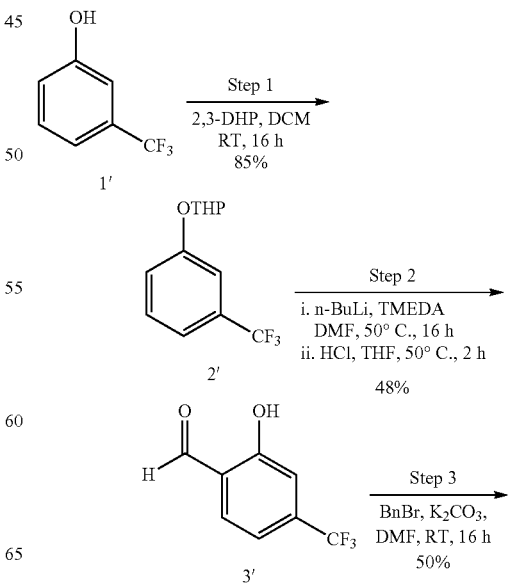

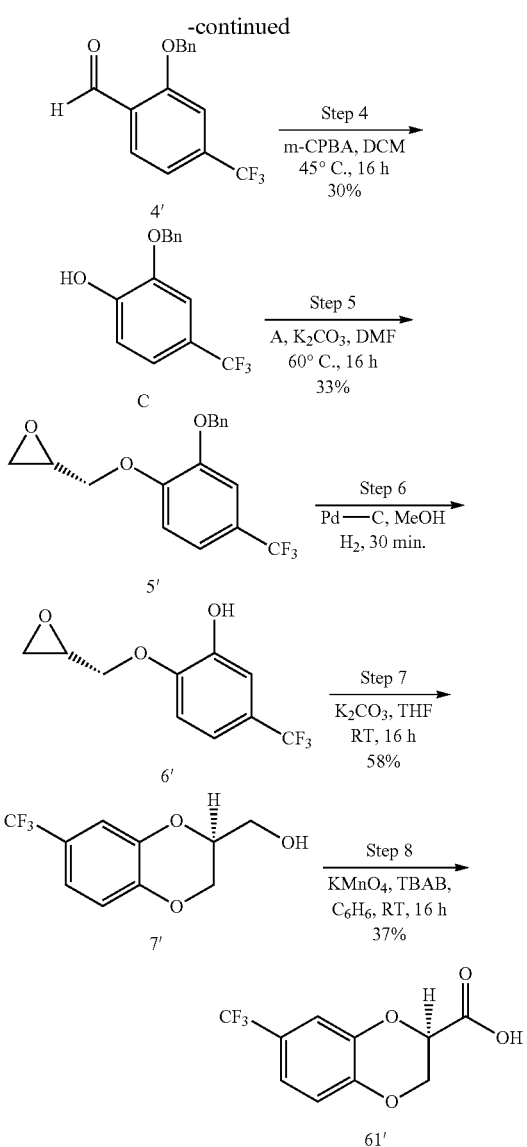

¹H NMR (CDCl₃, 300 MHz): δ 1.55-1.76 (m, 3H), 1.85-1.89 (m, 2H), 1.92-2.06 (m, 1H), 3.60-3.64 (m, 1H), 3.83-3.91 (m, 1H), 5.44-5.46 (m, 1H), 7.21-7.40 (m, 4H).

2-Hydroxy-4-trifluoromethylbenzaldehyde (3')

n-BuLi (40 mL, 1.6 M) was added drop wise at −10° C. under nitrogen atmosphere to TMEDA (11.88 g, 102 mmol) and stirred for 30 min, then compound 2' was added slowly by maintaining the reaction at −10° C. After 2 h DMF (5 mL) was added and the resultant reaction mixture was stirred at 50° C. for 16 h. After completion of the reaction (TLC), the reaction mixture was diluted with water and extracted with EtOAc (3×). The organic layer was dried over anhy. Na₂SO₄ and concentrated under reduced pressure. The obtained residue was dissolved in THF (100 mL) and dil HCl (32 mL in 21 mL of water) was added. The resultant mixture was stirred for 2 h at 50° C. After that the reaction mixture was extracted with EtOAc (3×) and the combined organic layers were washed with brine and dried over Na₂SO₄ and concentrated under reduced pressure. Purification by flash chromatography (SiO₂, 60-120 mesh, 2% EtOAc in Pet ether) afforded the title compound 3' as a pale yellow liquid (6.7 g, 48%).

¹H NMR (CDCl₃, 300 MHz): δ 7.20-7.30 (m, 1H), 7.69-7.73 (m, 2H), 9.99 (s, 1H), 11.0 (s, 1H); MS: [M−1]⁺=189.

2-Benzyloxy-4-trifluoromethyl-benzaldehyde (4')

To a stirring solution of compound 3' (10.0 g, 52 mmol) in dry DCM (60 mL) were added K₂CO₃ (8.84 g, 63 mmol) and benzylbromide (7.45 mL, 63.0 mmol) at RT and the resultant reaction mixture was stirred at RT for 16 h. After completion of the reaction (TLC), the reaction mixture was diluted With EtOAc, washed with water and brine solution. The EtOAc layer was dried over anhy. Na₂SO₄ and concentrated under reduced pressure. Purification by flash chromatography (SiO₂, 60-120 mesh, 1% EtOAc in Pet ether) afforded the title compound 4' as an off white solid (7.3 g, 50%).

¹H NMR (CDCl₃, 300 MHz): δ 5.23 (s, 2H), 7.25-7.37 (m, 2H), 7.40-7.46 (m, 5H), 7.95 (d, 1H, J=8.3 Hz), 10.55 (s, 1H).

2-Benzyloxy-4-trifluoromethyl-phenol (C)

To a stirring solution of compound 4' (40 g, 142 mmol) in dry DCM (600 mL) was added m-CPBA (60%, 98.2 g, 571 mmol) portion wise at RT under nitrogen atmosphere and the reaction mixture was heated to reflux for 16 h. After completion of the reaction, the reaction mixture was diluted with DCM and washed with sat NaHCO₃ solution. The DCM layer was dried over Na₂SO₄ and concentrated under reduced pressure. Purification by flash chromatography (SiO₂, 60-120 mesh, 5% EtOAc in Pet ether) afforded the title compound C as an off white solid (11.40 g, 30%).

¹H NMR (CDCl₃, 300 MHz): δ 5.13 (s, 2H), 5.91 (s, 1H), 6.99 (d, 1H; J=8.3 Hz), 7.17-7.28 (m, 2H), 7.38-7.47 (m, 5H); MS: [M−1]⁺=267.

(S)-2-((2-(Benzyloxy)-4-(trifluoromethyl)phenoxy) methyl)oxirane (5')

To a stirring solution of compound C (3.0 g, 11.0 mmol) in DMF (15 mL) were added K₂CO₃ (1.56 g, 11.0 mmol) and (R)-glycidyl-p-toluene sulfonate (A) (2.5 g, 11.0 mmol) and the resulting reaction mixture was heated to 60° C. for 16 h. After completion of the reaction (TLC), the reaction mixture was cooled to RT, diluted with water (50 mL) and extracted 2-(3-Trifluoromethyl-phenoxy)-tetrahydropyran (2')

To a stirring solution of 3-Trifluoromethylphenol 1' (37.0 g, 228.0 mmol) in dry DCM was added THP (47.96 g, 570 mmol) at RT under nitrogen atmosphere. To the resultant reaction mixture catalytic amount of 4 M HCl in dioxane was added and the reaction mixture was stirred at RT for 16 h. After completion of the reaction (TLC), the reaction mixture was diluted with DCM and washed with NaHCO₃ solution. The organic layer was dried over Na₂SO₄ and concentrated under reduced pressure. Purification by flash chromatography (SiO₂, 60-120 mesh, 2% EtOAc in Pet ether) afforded the title compound 2' as a pale yellow liquid (48 g, 85%).

with EtOAc (3×). The combined EtOAc layers were washed with brine, dried over Na₂SO₄ and concentrated under reduced pressure. Purification by flash chromatography (SiO₂, 60-120 mesh, 5% EtOAc in Pet ether) afforded the title compound 5' as an off white solid (1.2 g, 33%).

¹H NMR (CDCl₃, 300 MHz): δ 2.75-2.78 (m, 1H), 2.88-2.90 (m, 1H), 3.35-3.39 (m, 1H), 4.03-4.08 (m, 1H), 4.31-4.36 (m, 1H), 5.14 (s, 2H), 6.99 (d, 1H, J=8.2 Hz), 7.16-7.25 (m, 2H), 7.30-7.46 (m, 5H).

(S)-2-(Oxiran-2-ylmethoxy)-5-(trifluoromethyl)phenol (6')

To a stirring solution of compound 5' (2.4 g, 7.0 mmol) in MeOH (20 mL) was added Pd—C (250 mg) and the resultant reaction mixture was stirred under hydrogen atmosphere for 1 h at RT. After completion of the reaction (TLC), the reaction mixture was filtered through celite bed and the filtrate was concentrated under reduced pressure to afford the title compound 6 as a solid (1.7 g, 47% yield).

¹H NMR (CDCl₃, 300 MHz): δ 2.80-2.83 (m, 1H), 2.88-2.98 (m, 1H), 3.39-3.40 (m, 1H), 4.01-4.06 (m, 1H), 4.38-4.41 (m, 1H), 6.91-6.96 (m, 1H), 7.10-7.18 (m, 2H).

(S)-(7-(Trifluoromethyl)-2,3-dihydrobenzo[b][1,4]dioxin-2-yl)methanol (7')

To a stirring solution of compound 6' (1.7 g, 7.0 mmol) in THF (20 mL) was added sat. K₂CO₃ (9.0 mL) and the resultant reaction mixture was stirred at RT for 16 h. After completion of the reaction (TLC), the reaction mixture was diluted with water (50 mL) and extracted with EtOAc (3×). The combined EtOAc layers were dried over Na₂SO₄ and concentrated under reduced pressure. Purification by flash chromatography (SiO₂, 60-120 mesh, 4% EtOAc in Pet ether) afforded the title compound 7 as a yellow liquid (980 mg, 58%).

¹H NMR (CDCl₃, 300 MHz): δ 1.91 (t, 1H, J=5.8 Hz), 3.83-3.95 (m, 2H), 4.25-4.37 (m, 2H), 4.12-4.20 (m, 1H), 6.94 (d, 1H; J=8.7 Hz), 7.10-7.20 (m, 2H).

(R)-7-(Trifluoromethyl)-2,3-dihydrobenzo[b][1,4]dioxine-2-carboxylic acid (61')

To a stirring solution of compound 7' (980 mg, 5.0 mmol) in benzene (13 mL) at 10° C. were added aq KMnO₄ (1.32 g, 8 mmol) and TBAB (135 mg, 0.4 mmol) and the resultant reaction mixture was stirred at RT for 16 h. After completion of the reaction (TLC), the reaction mixture was filtered through celite and washed with EtOAc. The pH of the filtrate was adjusted to 2 with conc. HCl. The aqueous layer was extracted with EtOAc (3×), the combined EtOAc layer were dried over anhy. Na₂SO₄ and concentrated under reduced pressure to afford the title compound 61' as an off white solid (340 mg, 37%).

¹H NMR (DMSO, 300 MHz): δ 4.34 (dd, 1H, J₁=11.94, J₂=3.1 Hz), 4.53 (dd, 1H, J₁=11.94, J₂=3.1 Hz), 5.17 (m, 1H), 7.05 (d, 1H; J=8.3 Hz); 7.18-7.28 (m, 2H); 13.46 (br s, 1H).

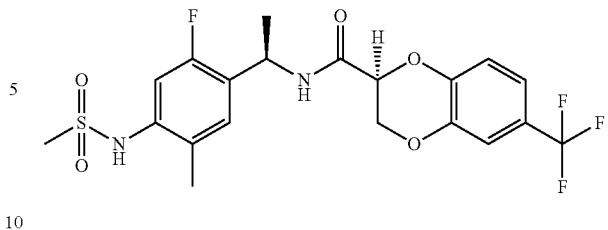

Synthesis of (S)—N—((R)-1-(2-fluoro-5-methyl-4-(methylsulfonamido)phenyl)ethyl)-6-(trifluoromethyl)-2,3-dihydrobenzo[b][1,4]dioxine-2-carboxamide A solution of (R)—N-(4-(1-aminoethyl)-5-fluoro-2-methylphenyl)methanesulfonamide hydrochloride (48 mg, 0.17 mmol) in N,N-dimethylformamide (3 mL) was stirred for 5 mins. (S)-6-trifluoromethyl-2,3-dihydrobenzo[b][1,4]dioxine-2-carboxylic acid (40 mg, 0.1 mol), N,N,N',N'-tetramethyl-O-(7-azabenzotriazol-1-yl)uronium hexafluorophosphate (200 mg, 0.4 mmol) and N,N-diisopropylethylamine (50 μL, 0.3 mmol) was added and the reaction was stirred at 50° C. overnight. Purification by HPLC afforded the final compound. m/z=477.1 (M+H)⁺. ¹H NMR (400 MHz; DMSO-d₆) δ 9.16 (s, 1H), 8.66 (t, 1H, J=8.3 Hz), 7.38 (d, 1H, J=2.2 Hz), 7.28-7.21 (m, 2H), 7.05-7.01 (m, 1H), 6.88 (d, 1H, J=8.5 Hz), 5.17-5.08 (m, 1H), 5.04-5.01 (m, 1H), 4.45-4.41 (m, 1H) 4.37-4.31 (m, 1H), 2.99 (s, 3H), 2.09 (s, 3H), 1.37 (d, 3H, J=6.9 Hz).

EXAMPLE 17

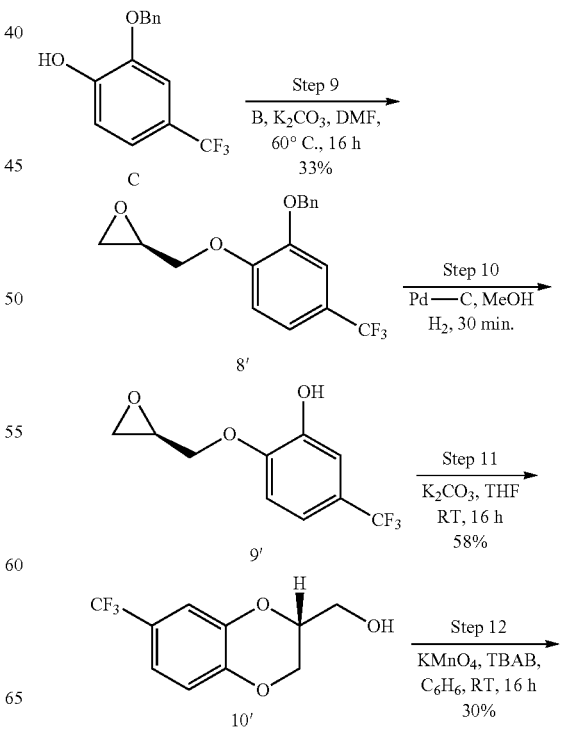

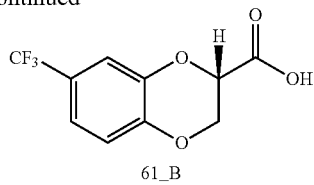

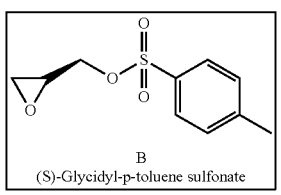

(R)-2-((2-(benzyloxy)-4-(trifluoromethyl)phenoxy) methyl)oxirane (8')

The title compound was prepared from compound C and (S)-glycidyl-p-toluene sulfonate (B) employing the procedure used for the preparation of compound 5'.

$^1$H NMR (CDCl$_3$, 300 MHz): δ 2.75-2.78 (m, 1H), 2.88-2.90 (m, 1H), 3.35-3.39 (m, 1H), 4.03-4.08 (m, 1H), 4.31-4.36 (m, 1H), 5.14 (s, 2H), 6.99 (d, 1H, J=8.2 MHz), 7.16-7.25 (m, 2H), 7.30-7.46 (m, 5H).

(R)-2-(oxiran-2-ylmethoxy)-5-(trifluoromethyl)phenol (9')

The title compound was prepared from compound 8' employing the procedure used for the preparation of compound 6'.

$^1$H NMR (CDCl$_3$, 300 MHz): δ 2.80-2.83 (m, 1H), 2.88-2.98 (m, 1H), 3.39-3.40 (m, 1H), 4.01-4.06 (m, 1H), 4.38-4.41 (m, 1H), 6.91-6.96 (m, 1H), 7.10-7.18 (m, 2H).

(R)-(7-(trifluoromethyl)-2,3-dihydrobenzo[b][1,4]dioxin-2-yl)methanol (10')

The title compound was prepared from compound 9' employing the procedure used for the preparation of compound 7'.

H$^1$ NMR (CDCl$_3$, 300 MHz): δ 1.91 (t, 1H, J=5.8 Hz); 3.83-3.95 (m, 2H); 4.10-4.20 (m, 1H), 4.25-4.37 (m, 2H); 6.94 (d, 1H; J=8.7 Hz); 7.10-7.17 (m, 2H).

(S)-7-(trifluoromethyl)-2,3-dihydrobenzo[b][1,4]dioxine-2-carboxylic acid (61_B)

To a stirring solution of compound 10' (1.3 g, 5.0 mmol) in benzene (17 mL) at 10° C. were added aq KMnO$_4$ (1.75 g, 11 mmol) and TBAB (178 mg, 0.5 mmol) and the resultant reaction mixture was stirred at RT for 16 h. After completion of the reaction (TLC), the reaction mixture was filtered through celite and washed with EtOAc. The pH of the filtrate was adjusted to 2 with conc. HCl. The aqueous layer was extracted with EtOAc (3×), the combined EtOAc layer were dried over anhy. Na$_2$SO$_4$ and concentrated under reduced pressure to afford the title compound 61_B as an off white solid (410 mg, 30%).

$^1$H NMR (DMSO, 300 MHz): δ 4.34 (dd; 1H, J1=11.9H, J2=3.1 Hz), 4.53 (dd, 1H, J1=11.9H, J2=3.1 Hz), 5.17 (m, 1H); 7.05 (d, 1H; J=8.3 Hz), 7.18-7.28 (m, 2H), 13.46 (br s, 1H).

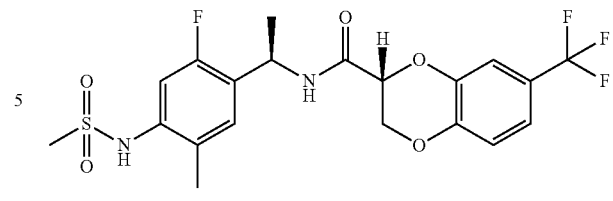

Synthesis of (R)—N—((R)-1-(2-fluoro-5-methyl-4-(methylsulfonamido)phenyl)ethyl)-7-(trifluoromethyl)-2,3-dihydrobenzo[b][1,4]dioxine-2-carboxamide Procedure same as in example 16 to give the compound. m/z=477.3 (M+H)$^+$. $^1$H NMR (400 MHz; DMSO-d$_6$) δ 9.20 (s, 1H), 8.65 (d, 1H, J=7.7 Hz), 7.33 (d, 1H, J=2.2 Hz), 7.26 (d, 1H, J=8.5 Hz), 7.20 (dd, 1H, J=8.6 Hz), 7.09-7.04 (m, 2H), 5.13-5.06 (m, 1H), 4.95-4.93 (m, 1H), 4.43 (dd, 1H), 4.35 (dd, 1H), 3.02 (s, 3H), 2.26 (s, 3H), 1.35 (d, 3H, J=7.1 Hz).

EXAMPLE 18

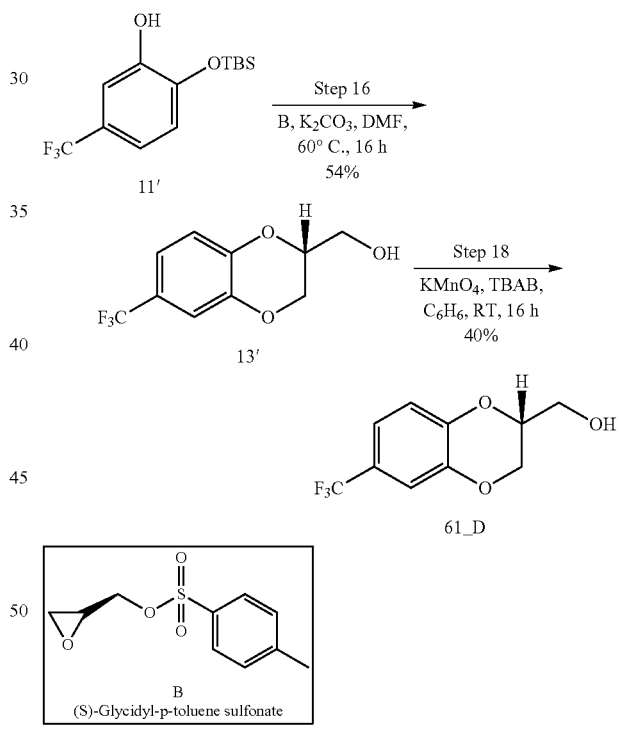

(R)-(6-(trifluoromethyl)-2,3-dihydrobenzo[b][1,4]dioxin-2-yl)methanol (13')

The title compound was prepared from compound 11' and (S)-glycidyl-p-toluene sulfonate (B) employing the procedure used for the preparation of compound 12' (see Example 19).

$^1$H NMR (CDCl$_3$, 300 MHz): δ 1.91 (t, 2H; J=6 MHz), 3.83-3.98 (m, 2H), 4.10-4.18 (m, 1H), 4.20-4.39 (m, 2H), 6.95-6.99 (m, H), 7.12-7.18 (m, 2H).

(S)-6-(trifluoromethyl)-2,3-dihydrobenzo[b][1,4]dioxine-2-carboxylic acid (61_D)

The title compound was prepared from compound 13' employing the procedure used for the preparation of compound 61_C (see Example 19).

¹H NMR (DMSO, 300 MHz): δ 4.31-4.37 (m, 1H), 4.51-4.56 (m, 1H), 5.17-5.20 (m, 1H), 7.04-7.29 (m, 3H), 13.51 (s, 1H).

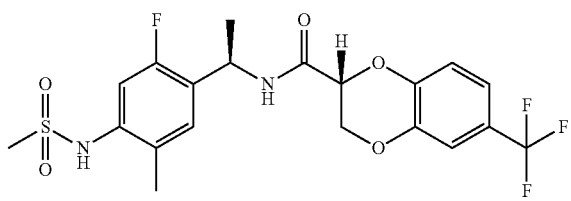

Synthesis of (R)—N—((R)-1-(2-fluoro-5-methyl-4-(methylsulfonamido)phenyl)ethyl)-6-(trifluoromethyl)-2,3-dihydrobenzo[b][1,4]dioxine-2-carboxamide Procedure same as in example 16 to give the compound. m/z=477.3 (M+H)⁺. ¹H NMR (400 MHz; DMSO-d₆) δ 9.20 (s, 1H), 8.69-8.64 (m, 1H), 7.33 (d, 1H, J=2.19 Hz), 7.27-7.16 (m, 2H), 7.09-7.04 (m, 2H), 5.13-5.06 (m, 1H), 4.97-4.93 (m, 1H), 4.45-4.33 (m, 2H), 3.02 (s, 3H), 2.26 (s, 3H), 1.35 (dd, 3H, J=6.98 Hz).

EXAMPLE 19

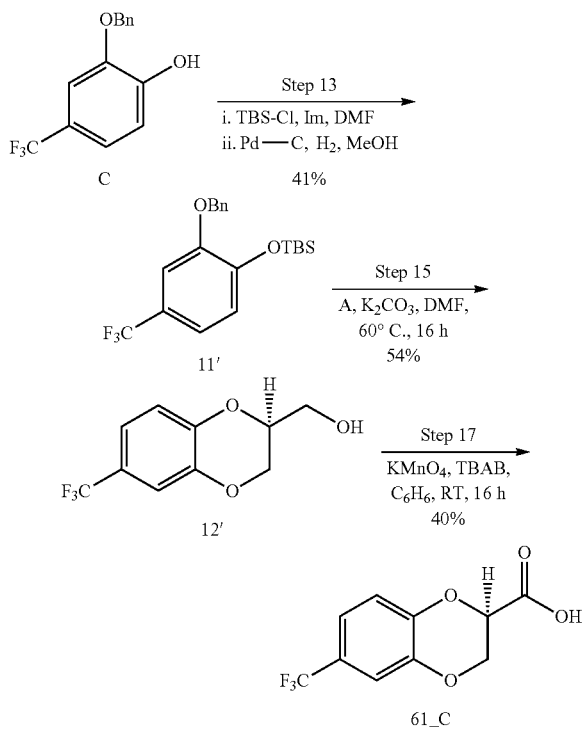

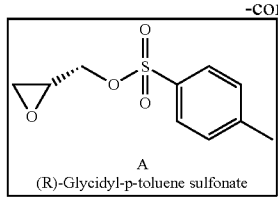

(R)-Glycidyl-p-toluene sulfonate

2-(tert-butyldimethylsilyloxy)-5-trifluoromethylphenol (11')

To a stirring solution of compound C (15.0 g, 55.9 mmol) in dry DMF (100 mL) at RT was added imidazole (11.4 g, 167.0 mmol) and after 30 min TBDMS-Cl (25.3 g, 167.0 mmol) was added and the resultant reaction mixture was heated to 60° C. for 16 h. After completion of the reaction (TLC), the reaction mixture was diluted with EtOAc and washed with water and sat. NaHCO₃ solution. The combined EtOAc layers were dried over Na₂SO₄ and concentrated under reduced pressure to afford 13.5 g of crude product.

To a solution of the above crude product in MeOH (100 mL) was added Pd—C (1.35 g) and the resultant reaction mixture was stirred under hydrogen atmosphere for 1 h at RT. After completion of the reaction (TLC), the reaction mixture was filtered through celite bed and the filtrate was concentrated under reduced pressure to afford the title compound 11' as a solid (6.7 g, 41% yield).

¹H NMR (CDCl₃, 300 MHz): δ 0.17 (s, 6H), 0.96 (s, 9H), 6.92-7.20 (m, 3H).

(S)-(6-(trifluoromethyl)-2,3-dihydrobenzo[b][1,4]dioxin-2-yl)methanol (12')

To a stirring solution of compound 11' (5.0 g, 17.0 mmol) in DMF (15 mL) were added K₂CO₃ (11.98 g, 85 mmol) and (R)-Glycidyl-p-toluene sulfonate (B) (3.9 g, 17 mmol) (2.5 g, 11.0 mmol) and the resulting reaction mixture was heated to 60° C. for 16 h. After completion of reaction (TLC), the reaction mixture was cooled to RT, diluted with water (50 mL) and extracted with EtOAc (3×). The combined EtOAc layers were washed with brine, dried over anhy. Na₂SO₄ and concentrated under reduced pressure. Purification by flash chromatography (SiO₂, 60-120 mesh, 3% EtOAc in Pet ether) afforded the title compound 12' as an off white solid (2.1 g, 54%).

¹H NMR (CDCl₃, 300 MHz): δ 1.89 (t, 1H; J=6.3 MHz), 3.86-3.94 (m, 2H), 4.13-4.19 (m, 1H), 4.28-4.39 (m, 2H), 6.95-6.99 (m, 1H), 7.11-7.18 (m, 2H).

(R)-6-(trifluoromethyl)-2,3-dihydrobenzo[b][1,4]dioxine-2-carboxylic acid (61_C)

To a stirring solution of compound 12' (2.5 g, 10.0 mmol) in benzene (17 mL) at 10° C. were added aq KMnO₄ (3.37 g, 21 mmol) and TBAB (343 mg, 1 mmol) and the resultant reaction mixture was stirred at RT for 16 h. After completion of the reaction (TLC), the reaction mixture was filtered through celite and washed with EtOAc. The pH of the filtrate was adjusted to 2 with conc. HCl. The aqueous layer was extracted with EtOAc (3×), the combined EtOAc layer were dried over anhy. Na₂SO₄ and concentrated under reduced pressure to afford the title compound 61_C as an off white solid (1.1 g, 40%).

H¹ NMR (DMSO, 300 MHz): δ 4.31-4.37 (m, 1H), 4.51-4.56 (m, 1H), 5.17-5.20 (m, 1H), 7.04-7.29 (m, 3H), 13.51 (s, 1H).

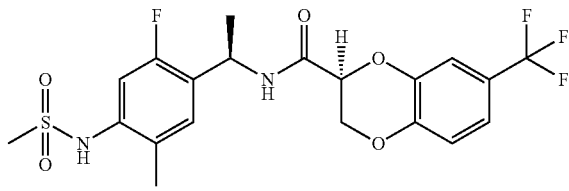

Synthesis of (S)—N—((R)-1-(2-fluoro-5-methyl-4-(methylsulfonamido)phenyl)ethyl)-7-(trifluoromethyl)-2,3-dihydrobenzo[b][1,4]dioxine-2-carboxamide Procedure same as in example 16 to give the compound. m/z=477.3 (M+H)⁺. ¹H NMR (400 MHz; DMSO-d₆) δ 9.15 (s, 1H), 8.65 (d, 1H, J=7.9 Hz), 7.38 (d, 1H, J=2.1 Hz), 7.22 (d, 1H, J=8.5 Hz), 7.05-7.01 (m, 2H), 6.88 (d, 1H, J=8.6 Hz), 5.17-5.10 (m, 1H), 5.02-5.01 (m, 1H), 4.44 (dd, 1H), 4.35 (dd, 1H), 2.99 (s, 3H), 2.09 (s, 3H), 1.37 (d, 3H, J=7.1 Hz).

EXAMPLE 20

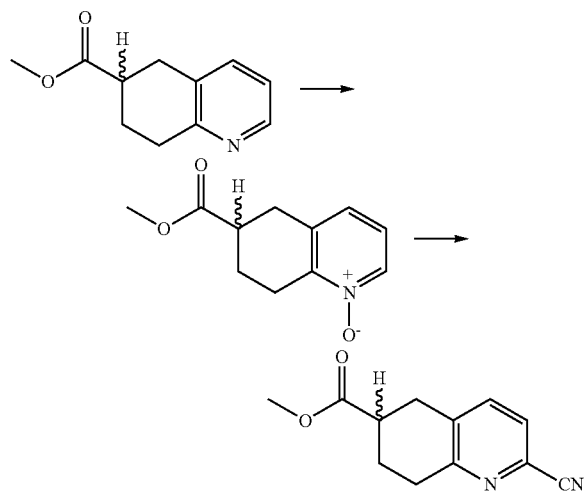

6-(Methoxycarbonyl)-5,6,7,8-tetrahydronuinoline 1-oxide and Methyl 5,6,7,8-tetrahydroquinoline-6-carboxylate To a solution of methyl 5,6,7,8-tetrahydroquinoline-6-carboxylate (3.21 g, 16.8 mmol) in Chloroform (100 mL, 1000 mmol) at room temperature, m-Chloroperbenzoic acid (4.96 g, 20.1 mmol) was added and the resulting solution was stirred at this temperature for 1.5 h: The reaction was quenched by addition of Dimethyl sulfoxide (0.36 mL, 5.1 mmol) and stirred at room temperature for 1 hr. The reaction mixture was poured into 1M Na₂CO₃ and the organic layers were extracted. The aqueous layer was extracted with CHCl₃ and the combined organic layers were dried (Na₂SO₄), filtered and concentrated in vacuo to afford the title product (3.49 g, 100%) as a yellow oil that was used without further purification into the next step. m/z=208.4 (M+H)⁺.

To a solution of 6-(methoxycarbonyl)-5,6,7,8-tetrahydroquinoline 1-oxide (13.58 g, 65.52 mmol) in acetonitrile (33 mL, 630 mmol), triethylamine (18 mL, 130 mmol), and trimethylsilyl cyanide (26.2 mL, 196 mmol) were added. The resulting mixture was heated at 120° C. in the microwave for 3 hr. The reaction was quenched by careful addition of 1M Na₂CO₃ and diluted with CH₂Cl₂. The combined organic layers were extracted and washed with 1 M NaH₂PO₄, dried (Na₂SO₄), filtered, concentrated in vacuo and purified by column chromatography twice (CH₂Cl₂:MeOH, 0-5% first; Hex:EtOAc, 50-100% second) to afford the title product (3.32 g, 23% yield) as a pale yellow solid. ¹H NMR (400 MHz, DMSO-d₆) S 7.54 (d, J=7.9 Hz, 1H), 7.47 (d, J=7.9 Hz, 1H), 3.74 (s, 3H), 3.18-2.94 (m, 4H), 2.88-2.78 (m, 1H), 2.35-22.26 (m, 1H), 2.09-1.97 (m, 1H). m/z=217.5 (M+H)⁺.

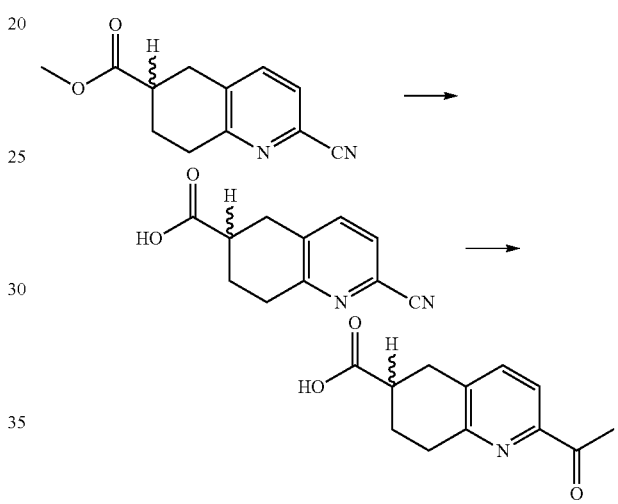

Cyano-5,6,7,8-tetrahydroquinoline-6-carboxylic acid and 2-Acetyl-5,6,7,8-tetrahydroquinoline-6-carboxylic acid A solution of methyl 2-cyano-5,6,7,8-tetrahydroquinoline-6-carboxylate (226 mg, 0.00104 mol), Lithium iodide (699 mg, 0.00522 mol), and Pyridine (2500 uL, 0.031 mol) was heated at 130° C. in the microwave for 3 hr. The reaction mixture was concentrated in vacuo and the residue was dissolved with CH₂Cl₂. The organic layers were washed with 0.5 M citric acid, dried (Na₂SO4), filtered and concentrated in vacuo to afford the title product (2.54 g, 82%) as a yellow solid that was used without further purification into the next step. m/z=203.3 (M⁺H)⁺.

To a cooled solution of 2-cyano-5,6,7,8-tetrahydroquinoline-6-carboxylic acid (2.50 g, 12.4 mmol) in Tetrahydrofuran (52 mL, 640 mmol) at 0° C., 3 M of Methylmagnesium Chloride in Tetrahydrofuran (11.1 mL, 37.1 mmol) was slowly added and the mixture was stirred at 0° C. for 5 minutes and then allowed to warm to room temperature. After 2 hr the reaction was quenched by addition of 1M citric acid and diluted with EtOAc. The organic layers were extracted with CHCl₃:IPA (3:1), dried (Na₂SO₄), filtered, concentrated in vacuo and purified by column chromatography (Hex:EtOAc, 20-60%) to afford the title product (2.27 g, 84%) as a yellow powder. ¹H NMR (400 MHz, CDCl₃) δ 12.43 (br s, 1H), 7.71 (s, 2H), 3.10-2.93 (m, 4H), 2.82-2.74 (m, 1H), 2.23-2.06 (m, 1H), 1.97-1.85 (m, 1H). m/z=220.3 (M+H)+.

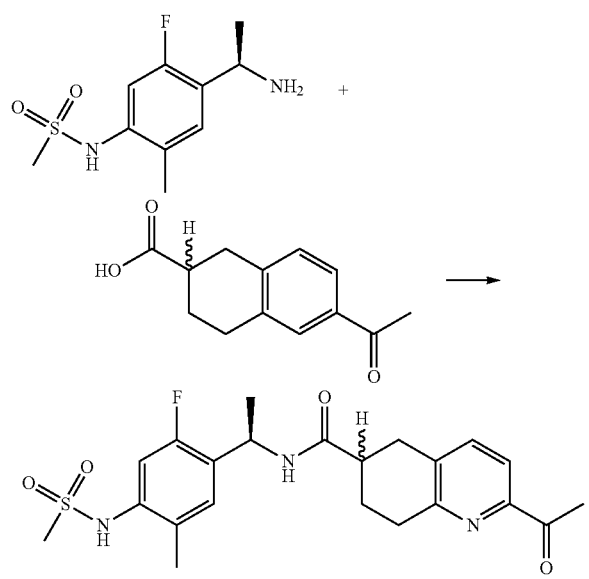

2-Acetyl-N—((R)-1-(2-fluoro-5-methyl-4-(methylsulfonamido)phenyl)ethyl)-5,6,7,8-tetrahydroquinoline-6-carboxamide To a mixture of N-[4-((R)-1-Aminoethyl)-5-fluoro-2-methylphenyl]methanesulfonamide hydrochloride (55.3 mg, 0.195 mmol), 2-acetyl-5,6,7,8-tetrahydroquinoline-6-carboxylic acid (45 mg, 0.20 mmol) and N,N,N',N'-Tetramethyl-O-(7-azabenzotriazol-1-yl)uronium Hexafluorophosphate (110 mg, 0.29 mmol) in N-Methylpyrrolidinone (192 uL, 1.99 mmol), N,N-Diisopropylethylamine (0.10 mL, 0.59 mmol) was added and the reaction was heated at 60° C. 4 h. The crude was diluted with EtOAc and washed with 1N HCl, 1M NaHCO$_3$ and brine. The combined organic layers were dried (MgSO$_4$), filtered and concentrated in vacuo to afford the title product (80 mg, 90%) as a brown oil that was used without further purification into the next step. m/z=448.4 (M+H)+.

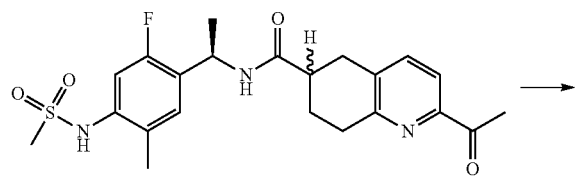

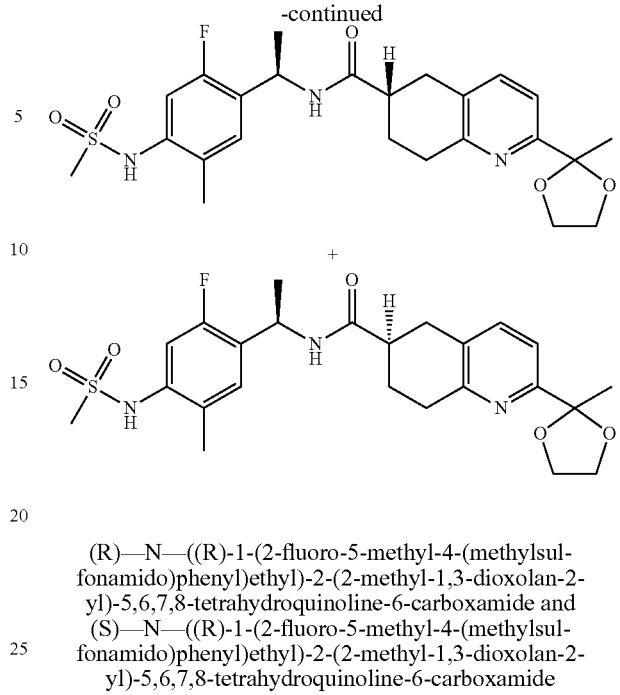

(R)—N—((R)-1-(2-fluoro-5-methyl-4-(methylsulfonamido)phenyl)ethyl)-2-(2-methyl-1,3-dioxolan-2-yl)-5,6,7,8-tetrahydroquinoline-6-carboxamide and
(S)—N—((R)-1-(2-fluoro-5-methyl-4-(methylsulfonamido)phenyl)ethyl)-2-(2-methyl-1,3-dioxolan-2-yl)-5,6,7,8-tetrahydroquinoline-6-carboxamide A solution of 2-acetyl-N—((R)-1-(2-fluoro-5-methyl-4-(methylsulfonamido)phenyl)ethyl)-5,6,7,8-tetrahydroquinoline-6-carboxamide (85 mg, 0.19 mmol), 1,2-ethanediol (0.04 mL, 0.8 mmol) and p-Toluenesulfonic Acid (3 mg, 0.02 mmol) in Benzene (7 mL, 80 mmol) was heated at 115° C. for 16 h using a Dean-Stark trap. The crude was concentrated in vacuo and purified by reverse-phase HPLC (10-50% MeCN in 10 mM Et$_2$NH/H$_2$O) to yield both diastereomers (10 mg, 9%) and (8 mg, 8%) as white solids. $^1$H NMR (400 MHz, DMSO-d$_6$) δ 9.14 (bs, 1H), 8.23 (d, J=8.1 Hz, 1H), 7.48 (d, J=8.1 Hz, 1H), 7.24 (d, J=8.1 Hz, 1H), 6.98 (d, J=9.2 Hz, 1H), 6.90 (d, J=8.1 Hz, 1H), 5.07-4.99 (m, 1H), 3.99-3.93 (m, 2H), 3.85-3.77 (m, 2H), 3.42 (q, J=7.1 Hz, 2H), 2.91-2.77 (m, 4H), 2.68 (s, 3H), 2.60-2.65 (m, 1H), 2.25 (s, 1H), 2.06 (s, 3H), 2.00-1.97 (m, 1H), 1.79-1.73 (m, 1H), 1.58 (s, 3H), 1.30 (d, J=7.0 Hz, 3H), 1.13 (t, J=7.0 Hz, 4H); m/z=492.1 (M+H)+. $^1$H NMR (400 MHz, DMSO-d$_6$) δ 9.17 (bs, 1H), 8.39 (d, J=8.1 Hz, 1H), 7.76 (d, J=8.1 Hz, 1H), 7.48 (d, J=8.1 Hz, 1H), 7.23 (d, J=9.2 Hz, 1H), 7.05 (d, J=8.1 Hz, 1H), 5.07-4.99 (m, 1H), 3.97-3.95 (m, 2H), 3.82-3.79 (m, 2H), 3.33 (s, 2H), 2.91-2.77 (m, 4H), 2.68 (s, 3H), 2.60-2.65 (m, 1H), 2.25 (s, 1H), 2.06 (s, 3H), 2.00-1.97 (m, 1H), 1.79-1.73 (m, 1H), 1.58 (s, 3H), 1.30 (d, J=7.0 Hz, 3H), 1.13 (t, J=7.0 Hz, 4H); m/z=491.8 (M+H)+.

EXAMPLE 21

Preparation of 6-trifluoromethyl-2,3-dihydro[1,4]dioxino[2,3-b]pyridine-3-carboxylic acid [(R)-1-(2-fluoro-4-methanesulfonylamino-5-methylphenyl)ethyl]amide

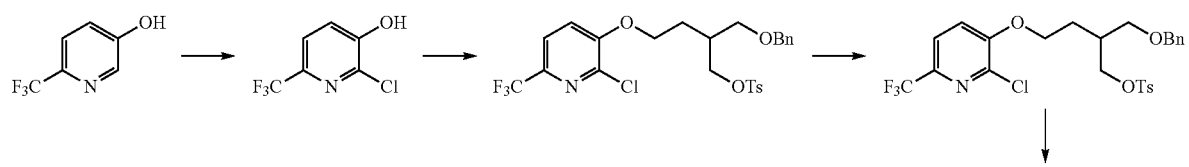

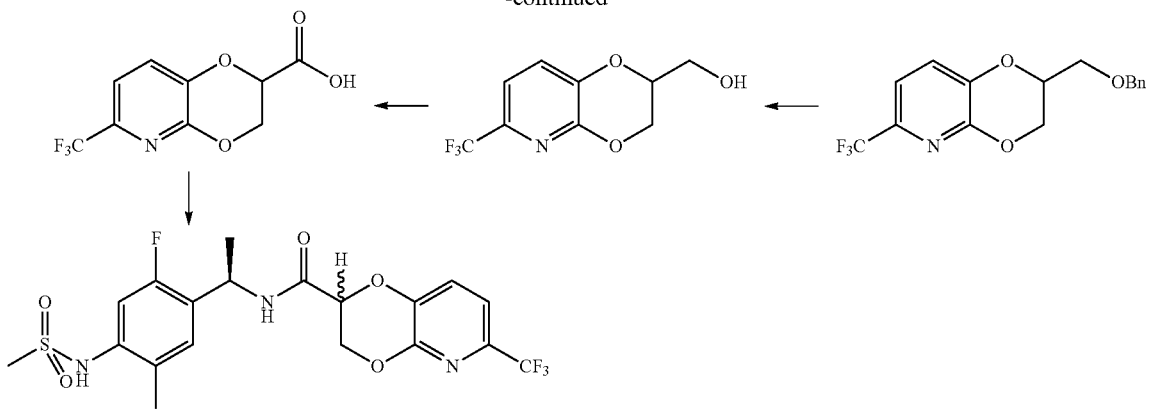

a. 1-Benzyl-3-tritylglycerol

To a stirred suspension of triphenylmethyl chloride (59.6 g, 0.21 mol) and triethylamine (32.6 mL, 0.23 mol) in tert-butyl alcohol (80 mL) at 60° C. was added a solution of 1-benzyloxy-2,3-propanediol (37.1 g, 0.20 mol) in tert-butyl alcohol (20 mL). The reaction was heated at reflux for 24 hours. The reaction mixture was evaporated to dryness, then purified using flash chromatography (0 to 30% EtOAc in hexanes) to afford the title compound (68 g, 75%) as an oil. m/z not found, r.t.=4.32 mins. $^1$H NMR (400 MHz; CDCl$_3$) δ 7.46-7.41 (6H, m), 7.36-7.22 (14H, m), 4.52 (2H, s), 4.02-3.95 (1H, m), 3.63-3.54 (2H, m), 3.26-3.18 (2H, m), 2.40 (1H, s).

b. Methanesulfonic acid 2-benzyloxy-1-trityloxymethylethyl ester

To a solution of 1-benzyl-3-tritylglycerol (17.5 g, 0.41 mol) in anhydrous dichloromethane (200 mL) at 0° C. was added triethylamine (8 mL, 0.58 mol) followed by methanesulfonyl chloride (4.1 mL, 0.54 mol). The reaction was stirred at 0° C. for 1 hour, then at room temperature for 2 hours. The reaction mixture was washed with 1N hydrochloric acid (30 mL), dried (Na$_2$SO$_4$), filtered and concentrated. Crystallisation using diisopropyl ether gave the title compound (15.2 g, 72%) as a solid. m/z not found, r.t.=4.41 mins. NMR (400 MHz; CDCl$_3$) δ7.43-7.41 (6H, m), 7.38-7.23 (14H, m), 4.90-4.83 (1H, m), 4.52 (2H, m), 3.75-3.63 (2H, m), 3.41-3.33 (2H, m), 3.02 (3H, s).

c. 2-Chloro-6-(trifluoromethyl)pyridin-3-ol

A solution of 6-(trifluoromethyl)pyridine-3-ol (7 g, 40 mmol) and sodium carbonate (4.5 g, 4.2 mmol) in water (200 mL) was cooled in an ice bath. 0.7N Sodium hypochlorite solution (63.9 mL, 4.29 mmol) was added portionwise over 30 minutes, and the reaction stirred at 0° C. for 2 hours. The reaction mixture was acidified using acetic acid, and extracted into EtOAc (3×50 mL). The combined organics were washed with brine (2×50 mL), dried (MgSO$_4$), filtered and concentrated. The product was purified by flash chromatography (0 to 25% EtOAc in hexanes) giving the title compound (1.6 g, 20%) as a solid. $^1$H NMR (400 MHz; CDCl$_3$) δ 7.61 (1H, d), 7.45 (1H, d), 5.83 (1H, s).

d. Preparation of 3-(1-benzyloxy)-3-(trityloxy)propan-2-yloxy)-2-chloro-6-(trifluoromethyl)pyridine To a stirred suspension of 95% sodium hydride (442 mg, 0.17 mol) in anhydrous DMF (50 mL) was added a solution of 2-chloro-6-(trifluoromethyl)pyridin-3-ol (3.46 g, 0.17 mol) in anhydrous DMF (10 mL), portionwise over 5 minutes. The reaction mixture was heated to 60° C., and a solution of methanesulfonic acid 2-benzyloxy-1-trityloxymethylethyl ester (6.29 g, 0.12 mol) in anhydrous DMF (20 mL) was added. The reaction was heated at reflux for 4 hours, then allowed to cool and evaporated to dryness. Water (50 mL) was added, and the product extracted into EtOAc (3×50 mL) and the combined organics were washed with brine (3×50 mL), dried (MgSO$_4$), filtered and concentrated. Flash chromatography (0 to 30% EtOAc in hexanes) gave the title compound (3.09 g, 33%) as a light brown oil. m/z=604.5 (M+1), r.t.=4.46 mins. $^1$H NMR (400 MHz; CDCl$_3$) δ7.42-7.20 (2H, m), 4.64-4.60 (1H, m), 4.53 (2H, s), 3.67 (2H, dd), 3.48-3.41 (2H, m).

e. Preparation of 3-(benzyloxy)-2-(2-chloro-6-(trifluoromethyl)pyridine-3-yloxy)propan-1-ol To a solution of 3-(1-benzyloxy)-3-(trityloxy)propan-2-yloxy)-2-chloro-6-(trifluoromethyl)pyridine (3 g, 4 mmol) in tetrahydrofuran (80 mL) was added 4N hydrochloric acid (20 mL). The reaction was heated at reflux for 4 hours, then cooled. The reaction mixture was poured into saturated NaHCO$_3$ solution (100 mL) and extracted with EtOAc (3×50 mL). The combined organics were washed with brine (3×30 mL), dried (MgSO$_4$), filtered and concentrated. Flash chromatography (0 to 30% EtOAc in hexanes) gave the title compound (1.16 g, 80%) as an oil. m/z=362.2 (M+1), r.t.=3.25 mins. $^1$H NMR (400 MHz; CDCl$_3$) δ55 (2H, s), 7.37-7.31 (3H, m), 7.29-7.25 (2H, m), 4.62-4.57 (1H, m), 4.56 (2H, s), 3.94-3.91 (2H, m), 3.76 (2H, m), 1.23 (1H, t).

f. Preparation of 2-(benzyloxymethyl)-6-(trifluoromethyl)-2,3-dihydro[1,4]dioxino[2,3-b]pyridine To a stirred suspension of sodium hydride (75 mg, 3.1 mmol) in anhydrous 1,2-dimethoxyethane (30 mL) was added a solution of 3-(benzyloxy)-2-(2-chloro-6-(trifluoromethyl)pyridine-3-yloxy)propan-1-ol (1.13 g, 3.1 mmol) in anhydrous 1,2-dimethoxyethane (30 mL), dropwise over 5 minutes. The reaction was heated at reflux for 90 minutes, then allowed to cool. The reaction mixture was poured into saturated NaHCO$_3$ solution (50 mL) and extracted with EtOAc (3×30 mL). The combined organics were washed with brine (3×30 mL), dried (MgSO$_4$), filtered and concentrated. Flash chromatography (0 to 20% EtOAc in hexanes) gave the title compound (450 mg, 43%) as an oil. m/z=325.6 (M+1), r.t.=3.46 mins. $^1$H NMR (400 MHz; CDCl$_3$) δ57.36-7.25 (7H, m), 4.62 (2H, d), 4.60-4.53 (1H, m, 4.43 (1H, dd), 4.18 (1H, dd), 3.87 (1H, dd), 3.74 (1H, dd).

g. Preparation of (6-trifluoromethyl-2,3-dihydro[1,4]dioxino[2,3-b]pyridine-2-yl)methanol To a stirred solution of 2-benzyloxymethyl-6-trifluoromethyl-2,3-dihydro[1,4]dioxino[2,3-b]pyridine (420 mg, 1.3 mmol) in ethanol (50 mL) was added 10% palladium on carbon (10 mg, cat.). The reaction mixture was evacuated and purged with hydrogen six times, then stirred for 3 hours under a hydrogen atmosphere. The reaction mixture was filtered through celite, washing with EtOH (60 mL), and the filtrate evaporated to dryness. Trituration using DCM/hexanes gave the title compound (250 mg, 78%) as a solid. m/z=236.2 (M+1), r.t.=2.46 mins. $^1$H NMR (400 MHz; CDCl$_3$) δ7.38-7.28 (2H, m), 4.50-4.46 (1H, m), 4.41 (1H, dd), 4.20 (1H, dd), 4.04 (1H, dd), 3.90 (1H, dd).

h. Preparation of 7-trifluoromethyl-2,3-dihydro[1,4]dioxino[2,3-b]pyridine-3-carboxylic acid (6-Trifluoromethyl-2,3-dihydro[1,4]dioxino[2,3-b]pyridine-2-yl)methanol (250 mg, 1.1 mmol) was partially dissolved in 0.62N potassium hydroxide in water (10.2 mL, 6.4 mmol). Potassium permanganate (370 mg, 2.3 mmol) was added in one portion, and the reaction was stirred at room temperature for 2 hours. The reaction mixture was acidified with acetic acid and diluted with water (30 mL), then extracted into EtOAc (3×20 mL). the combined organics were washed with brine (20 mL), dried (MgSO$_4$), filtered and concentrated. Trituration using DCM/hexanes gave the title compound (200 mg, 70%) as a solid. m/z=248.0 (M−1), r.t.=2.86 mins. $^1$H NMR (400 MHz; DMSO-d$_6$) δ13.7 (1H, br. s), 7.51 (1H, dd), 7.46 (1H, d), 5.40 (1H, t), 4.58 (1H, dd), 4.42 (1H, dd).

i. Preparation of 6-trifluoromethyl-2,3-dihydro[1,4]dioxino[2,3-b]pyridine-2-carboxylic acid [(R)-1-(2-fluoro-4-methanesulfonylamino-5-methylphenyl)ethyl]amide To a solution of N-[4-((R)-1-Aminoethyl)-5-fluoro-2-methylphenyl]methanesulfonamide hydrochloride (25 mg, 0.09 mmol), 6-trifluoromethyl-2,3-dihydro[1,4]dioxino[2,3-b]pyridine-2-carboxylic acid (20 mg, 0.08 mmol), 4-dimethylaminopyridine (0.8 mg, 0.8 mop and N,N-diisopropylethylamine (50 μL, 0.29 mmol) in anhydrous DMF (1 mL) was added HATU (34 mg, 0.09 mmol). The reaction was stirred overnight at room temperature, then poured into saturated NaHCO$_3$ solution (20 mL) and extracted with EtOAc (3×20 mL). The combined organics were washed with brine (3×30 mL), dried (MgSO$_4$), filtered and concentrated. Flash chromatography (0 to 3.5% MeOH in DCM) gave the title compound (24 mg, 60%) as a solid. m/z=478.2 (M+1), r.t.=2.98 mins. $^1$H NMR (400 MHz; DMSO-d$_6$) δ9.20 (1H, dd), 8.82 (1H, dd), 7.51-7.43 (2H, m), 7.27 (0.5H, d), 7.14 (0.5H, d), 7.07 (1H, dd), 5.20-5.17 (1H, m), 5.09 (1H, t), 4.48-4.42 (2H, m), 3.01 (3H, d), 2.27 (1.5H, s), 2.21 (1.5H, s), 1.38 (3H, d).

EXAMPLE 22

Preparation of (R)-6-Trifluoromethyl-2,3-dihydrobenzo[1,4]dioxine-2-carboxylic acid [(R)-1-(3-fluoro-4-methanesulfonylaminophenyl)ethyl]amide

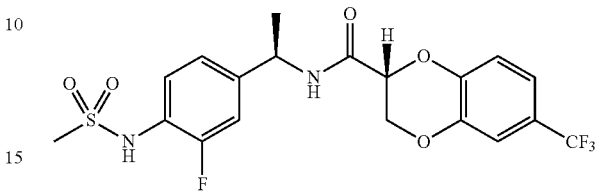

To a solution of N-[4-(R)-1-Aminoethyl)-2-fluorophenyl]methanesulfonamide hydrochloride (54 mg, 0.20 mmol), 6-trifluoromethyl-2,3-dihydro[1,4]dioxino[2,3-b]pyridine-2-carboxylic acid (50 mg, 0.20 mmol), 4-dimethylaminopyridine (2.0 mg, 1.6 μmol) and N,N-diisopropylethylamine (126 μL, 0.72 mmol) in anhydrous DMF (2 mL) was added HATU (84 mg, 0.09 mmol). The reaction was stirred overnight at room temperature, then poured into saturated NaHCO$_3$ solution (20 mL) and extracted with EtOAc (3×30 mL). The combined organics were washed with brine (3×30 mL), dried (MgSO$_4$), filtered and concentrated. Flash chromatography (0 to 3.5% MeOH in DCM) gave the title compound (38 mg, 39%) as a solid. m/z=463.1 (M+1), r.t.=3.12 mins. $^1$H NMR (400 MHz; DMSO-d$_6$) δ9.56 (1H, s), 8.66 (1H, d), 7.35-7.15 (5H, m), 7.07 (1H, d), 4.97-4.94 (2H, m), 4.44 (1H, dt), 4.44-4.36 (1H, m), 3.01 (3H, s), 1.36 (3H, d).

EXAMPLE 23

Preparation of (R)-6-Trifluoromethyl-2,3-dihydrobenzo[1,4]dioxine-2-carboxylic acid [R)-1-(3-chloro-4-methanesulfonylaminophenyl)ethyl]amide

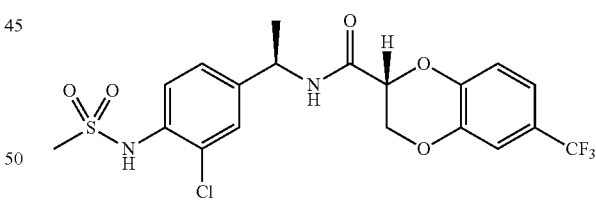

To a solution of N-[4-((R)-1-Aminoethyl)-2-chlorophenyl]methanesulfonamide hydrochloride (57.4 mg, 0.20 mmol), 6-trifluoromethyl-2,3-dihydro[1,4]dioxino[2,3-b]pyridine-2-carboxylic acid (50 mg, 0.20 mmol), 4-dimethylaminopyridine (2.0 mg, 1.6 umol) and N,N-diisopropylethylamine (126 uL, 0.72 mmol) in anhydrous DMF (2 mL) was added HATU (84 mg, 0.09 mmol). The reaction was stirred overnight at room temperature, then poured into saturated NaHCO$_3$ solution (20 mL) and extracted with EtOAc (3×30 mL). The combined organics were washed with brine (3×30 mL), dried (MgSO$_4$), filtered and concentrated. Flash chromatography (0 to 3% MeOH in DCM) gave the title compound (37 mg, 36%) as a solid. m/z=479.2 (M+1), r.t.=3.19 mins. $^1$H NMR (400 MHz; DMSO-d$_6$) δ9.45 (1H, s), 8.67

(1H, d), 7.49 (1H, s), 7.40 (1H, d), 7.33-7.15 (3H, m), 7.07 (1H, d), 4.95-4.85 (2H, m), 4.45-4.30 (2H, m), 3.03 (3H, s), 1.35 (3H, d).

Representative Example for Assignment of Stereochemistry

Assignment of stereochemistry for (R)-2-(1,1,1-trifluoro-2-methylpropan-2-yl)-5,6,7,8-tetrahydroquinoline-6-carboxylic acid Preparation of (R)—N-(4-bromophenyl)-2-(1,1,1-trifluoro-2-methylpropan-2-yl)-5,6,7,8-tetrahydroquinoline-6-carboxamide

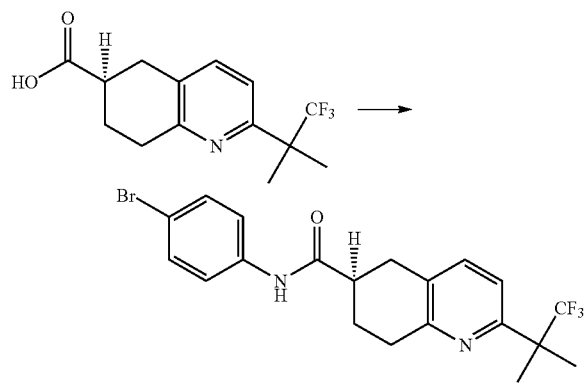

(R)-2-(1,1,1-Trifluoro-2-methylpropan-2-yl)-5,6,7,8-tetrahydroquinoline-6-carboxylic acid (30 mg), 4-bromoaniline (17.9 mg), propanephosphonic acid cyclic anhydride (50% wt solution in dichloroethane) (0.093 mL), triethylamine (0.044 mL), and dioxane (2 mL) were combined and heated in a microwave at 14° C. for 20 mins. The solution was evaporated and the residue dissolved in ethyl acetate and extracted with sodium carbonate soln (2×20 ml) and brine (3×20 ml). The organic layer was separated, dried (Na2SO4), filtered and evaporated to give a gum which solidified on standing. Yield 40 mg.

Crystallization of the crude bromophenyl compound by slow evaporation from methanol resulted in single crystals suitable for X-ray.

X-ray structure of (R)—N-(4-bromophenyl)-2-(1,1,1-trifluoro-2-methylpropan-2-yl)-5,6,7,8-tetrahydroquinoline-6-carboxamide Single Crystal X-ray Analysis.

A representative crystal was surveyed and a 1 Å data set (maximum sin $\Theta/\lambda=0.5$) was collected on a Bruker APEX II/R diffractometer. The crystals were mostly aggregates of single crystals (not twins) and gave a very complex diffraction pattern. A very small crystal proved to be a true single crystal with a marginal diffraction pattern (few high angle reflections). The crystal was triclinic with eight molecules in the asymmetric unit. Friedel pairs were collected in order to facilitate the determination of the absolute configuration. Atomic scattering factors were taken from the International Tables for Crystallography (International Tables for Crystallography, Vol. C, pp. 219,500, Kluwer Academic Publishers, 1992). All crystallographic calculations were facilitated by the SHELXTL system (SHELXTL, Version 5.1, Bruker AXS, 1997). All diffractometer data were collected at room temperature.

A trial structure was obtained by direct methods. This trial structure refined routinely. Hydrogen positions were calculated wherever possible. The methyl hydrogens were located by difference Fourier techniques and then idealized. The hydrogen parameters were added to the structure factor calculations but were not refined. The shifts calculated in the final cycles of least squares refinement were all less than 0.1 of the corresponding standard deviations. The final R-index was 7.31%. A final difference Fourier revealed no missing or misplaced electron density.

The refined structure was plotted using the SHELXTL plotting package (FIG. 1). The absolute configuration was determined by the method of Flack (H. D. Flack, *Acta Crystallogr.*, A39, 876, 1983). All eight molecules were the same enantiomer.

Figure 1:

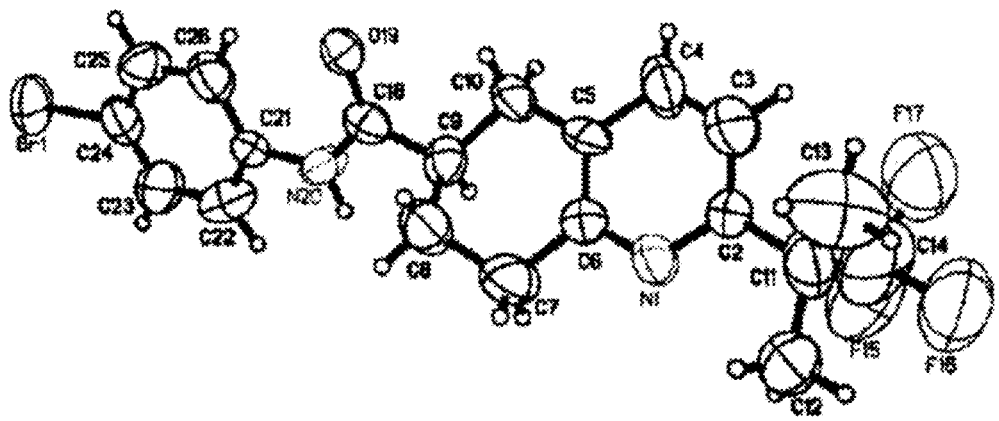

General Method for Automated Parallel LC-MS Purification of Libraries

The libraries were purified using a Perkin Elmer API100 mass spectrometer coupled to Shimadzu LC pumps. The chromatographic method employed was 10-100% gradient of acetonitrile to water over 8 minutes at a flow rate of 6 ml per minute. The column used was a 10×50 mm YMC C18 and the compounds were collected using a Gilson 204 fraction collector.

Following the methods described above and the appropriate reagents, starting materials and purification methods known to those skilled in the art, the amide compounds of this invention were or can be prepared.

The synthetic and biological examples presented herein are offered to illustrate this invention and are not to be construed in any way as limiting the scope of this invention. In the examples below, all temperatures are in degrees Celsius (unless otherwise indicated).

The compounds that have been prepared in accordance with the invention are presented in Table 1, below. The syntheses of these representative compounds were carried out in accordance with the methods set forth above, and activity of the compounds was measured by percent inhibition in a calcium uptake assay, the details of which are described below.

Calcium Uptake Assay.

Functional activity of compounds against the VR1 receptor was determined by measuring changes in intracellular calcium in HEK 293 cells expressing hVR1. Compounds were examined for their ability to inhibit agonist-induced calcium influx. Relative levels of $[Ca^{2+}]$ were monitored in a 96-well format using a calcium-sensitive fluorescence dye and a FLIPR TETRA, Molecular Devices.

Cell Line and Culture Conditions:

Cells that express high levels of VR1 were obtained by generation of a cell line from human keratinocytes with heterologous expression of VR1 under control of an inducible promoter. Specifically, cells expressing human VR1 under the control of the human cytomegalovirus immediate-early (CMV) promoter and two tetracycline operator 2 (TetO2) sites were made using the T-REx System (Invitrogen, Carlsbad, Calif., USA). Details and methods concerning this system are published (Hum. Gene Ther. 9, pp. 1939-1950, 1998; Annu. Rev. Microbiol. 48, pp. 345-369, 1994; Mol. Biol. 169, pp. 707-721, 1983). Human VR1 was subcloned into the T-REx System pcDNA5/TO vector (Invitrogen Cat# V1033-20) which was transfected into the T-REx System human keratinocyte cell line (Invitrogen Cat# R710-07) from which a stable cell line was established which expresses VR1 after induction by exposure to tetracycline or doxycycline (Hum. Gene Ther. 9, pp. 1939-1950, 1998; instructions that come with purchase of products noted above). Cells were maintained in a $CO_2$ incubator (5% $CO_2$) at 37° C. in culture medium containing DMEM with phenol red (Mediatech Cat #: 15-017-CV) supplemented with 10% heat-inactivated Fetal Bovine Serum, 5% Penicillin-streptomycin (Mediatech Cat #: 30-002-CI), 5% Glutamax® (L-Alanyl-L-Glutamine, Mediateach Cat #: 25-015-CI), 200 µg/ml hygromycin (Mediatech #:30-240-CR), 0.5 µg/ml blasticidin (Invitrogen #46-1120)).

Determination of $IC_{50}$ Values Against Agonist Stimulation

For assay preparation, cells expressing human VR1 as described above were plated in 96-well plates (Becton Dickinson [BD] poly-D-lysine coated 96-well plates, cat#356692) at 55,000 cells per well in culture media (described above) that also contained 1 ug/ml doxycycline. Plated cells were then placed in an incubator (5% $CO_2$) and incubated for 20-26 hours at 37° C., until the cells had grown to near confluency. Media was then aspirated from cells and 50 uL of dye-containing buffer (from Molecular Devices FLIPR Calcuim 4 Assay kit, cat# R8141) was added to each well. Cells were then left in the dark at room temperature for 1.5-2 hours. Cell plates were then placed in the FLIPR TETRA (Molecular Devices, CA, USA). Test compounds and agonists were added to wells using the liquid handling capability of the FLIPR TETRA. Calcuim responses of the cells were monitored by fluorescence readout of dye signal. Test compounds in saline (130 mM NaCl, 17 g/L sucrose, 1.8 g/L glucose, 8.8 mM HEPES, 3 mM KCl, 0.60 mM MgCl, 1.0 mM $CaCl_2$; adjust to pH 7.4 using NaOH; 0.03% BSA added on the day of the experiment), or vehicle control in saline, were pre-incubated at the desired final concentrations in the dark at room temperature for 2 or 30 minutes with cells already containing the above mentioned dye buffer (dye solution was diluted 1:1 in culture wells with saline containing 2× the final concentration of test compound). Compound $IC_{50}$ experiments were run using an agonist concentration at or near the $EC_{50}$ of the agonist. One agonist used was capsaicin at a final concentration of either 10 nM or the $EC_{50}$ of capsaicin as determined by running a dose response curve of capsaicin on the day of the experiment (which yielded $EC_{50}$ values ranging between 2.5 nM and 11 nM depending on the day). Another agonist was protons via a low pH solution (saline solution described above plus 10 mM citric acid buffered to pH 5.7 with HCl instead of buffering to a neutral pH with NaOH as done for normal saline). Compounds were tested at various concentration ranges, depending upon potency of compound. After the 2 minute or 30 minute compound pre-treatment, treatment solution was then added to cells by adding a volume of treatment solution equal to the pretreatment solution already on the cells. The treatment solution consisted of the test compound at the same target concentration as in pre-treatment in addition to agonist: either capsaicin at 2× the final desired concentration in saline to yield 1× final when diluted with the solution already in the wells or treatment solution was made without capsaicin and instead compound was appropriately diluted into the saline buffer described above for low pH agonism. Recordings were made to measure the fluorescence signal ($\lambda$ex=470-495 nm, $\lambda$em=515-575 nm) for at least 2 minutes after agonist addition (enough time for the fluorescence response to reach and then decline from the absolute maximum, agonist-induced signal attained). The percent inhibition value of the test compound at a given concentration tested was calculated as:

$$\% \text{ inhibition} = 100 \times \left[ 1 - \frac{\left(\frac{\text{Response of Agonist with Compound} -}{\text{Response of Vehicle alone}}\right)}{\left(\frac{\text{Response of Agonist with Vehicle} -}{\text{Response of Vehicle alone}}\right)} \right]$$

Where, response was calculated as the difference between the maximum fluorescence signal obtained after agonist addition and the signal level seen at baseline before agonist, but after antagonist, addition (the absolute minimum level of fluorescence signal observed in the 10 seconds prior to agonist addition). $IC_{50}$ values were calculated by curve fitting estimation. Percent inhibition data across the compound concentrations tested were used to create a dose-response curve of the test compound against the agonist. These data were then fit to a 4-parameter sigmoidal curve (variable slope) equation using Graphpad Prism software (by Graphpad Software, San Diego, Calif.): y=Bottom+(Top-Bottom)/(1-10^((logIC$_{50-x}$)*Hillslope), where x=log(concentration). The results obtained with representative compounds of the invention, prepared according to the methods descrbed herein, are set forth in Table 1, below.

In Table 1, activity of each compound is expressed as follows:

\+ compound with IC$_{50}$>1000 nM (Capsaicin)
++ compound with IC$_{50}$ 501-1000 nM (Capsaicin)
+++ compound with IC$_{50}$ 101-500 nM (Capsaicin)
++++ compound with IC$_{50}$<100 nM (Capsaicin)

\* compound with IC$_{50}$>1000 nM (Low pH)
\** compound with IC$_{50}$ 501-1000 nM (Low pH)
\*** compound with IC$_{50}$ 101-500 nM (Low pH)
\**** compound with IC$_{50}$<100 nM (Low pH)

TABLE 1

| | AMIDE COMPOUNDS | | | | |
|---|---|---|---|---|---|
| ID | Structure | MW (Calcd) | MS (Obs) | IC$_{50}$ (nM) Capsaicin | IC$_{50}$ (nM) Low pH |
| 1 | Chiral | 404.46 | 405.10 | ++++ | *** |
| 2 | Chiral | 406.48 | 407.20 | +++ | * |
| 3 | Chiral | 404.50 | 405.10 | ++++ | *** |
| 4 | Chiral | 438.91 | 439.20 | ++++ | **** |
| 5 | Chiral | 448.56 | 449.50 | +++ | * |
| 6 | Chiral | 440.92 | 441.40 | ++++ | **** |

TABLE 1-continued

AMIDE COMPOUNDS

| ID | Structure | | MW (Calcd) | MS (Obs) | IC$_{50}$ (nM) Capsaicin | IC$_{50}$ (nM) Low pH |
|---|---|---|---|---|---|---|
| 7 | 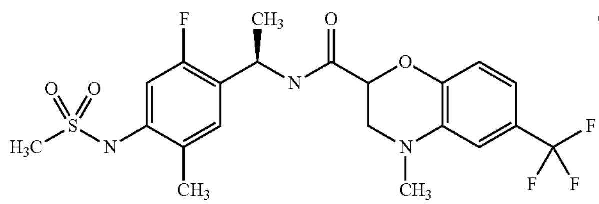 | Chiral | 489.49 | 490.40 | ++++ | **** |
| 8 | 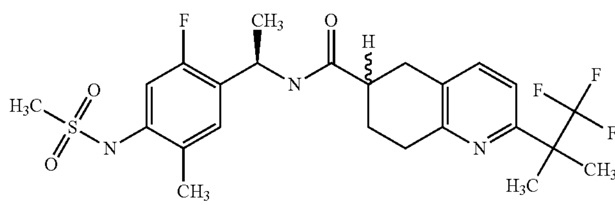 | Chiral | 515.57 | 516.30 | ++++ | |
| 9 | 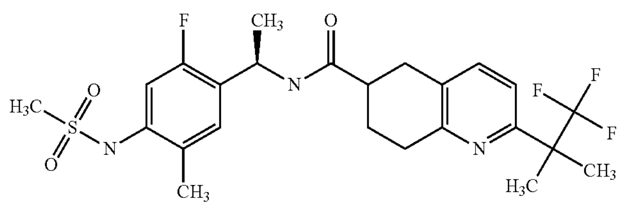 | | 515.57 | 516.20 | ++++ | **** |
| 10 | 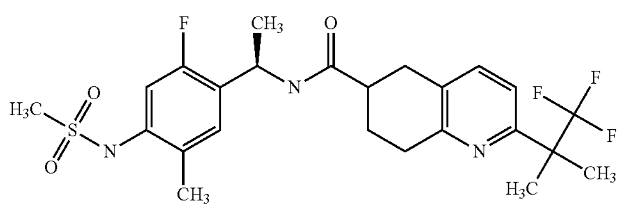 | | 515.57 | | ++++ | **** |
| 11 | 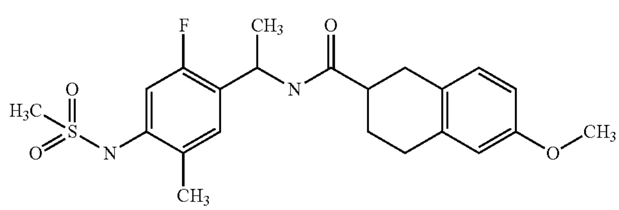 | | 434.53 | 435.20 | +++ | |
| 12 | 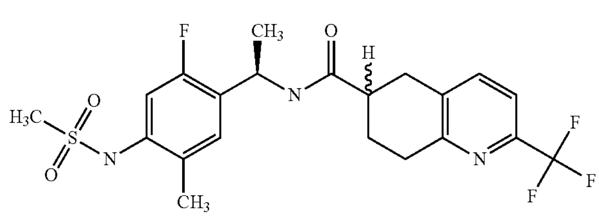 | Chiral | 473.49 | 474.40 | ++++ | |
| 13 | 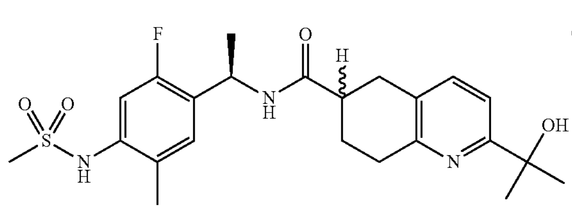 | Chiral | 440.46 | | +++ | |

TABLE 1-continued

| | AMIDE COMPOUNDS | | | | |
|---|---|---|---|---|---|
| ID | Structure | MW (Calcd) | MS (Obs) | IC$_{50}$ (nM) Capsaicin | IC$_{50}$ (nM) Low pH |
| 14 | Chiral | 477.6 | 477.9 | +++ | *** |
| 15 | Chiral | 477.6 | 477.8 | ++++ | **** |
| 16 | Chiral | 476.45 | 477.1 | +++ | |
| 17 | Chiral | 476.45 | 477.3 | ++++ | |
| 18 | Chiral | 476.45 | 477.3 | ++++ | |
| 19 | Chiral | 476.45 | 477.3 | +++ | |
| 20 | Chiral | 491.58 | 491.8 | +++ | |

TABLE 1-continued

AMIDE COMPOUNDS

| ID | Structure | | MW (Calcd) | MS (Obs) | IC$_{50}$ (nM) Capsaicin | IC$_{50}$ (nM) Low pH |
|---|---|---|---|---|---|---|
| 21 | 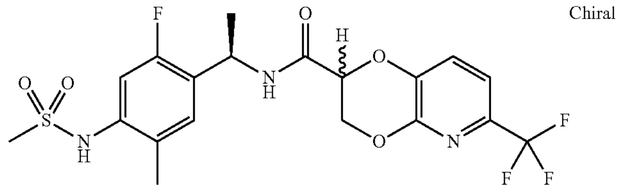 | Chiral | 477.43 | 478.2 | +++ | |
| 22 | 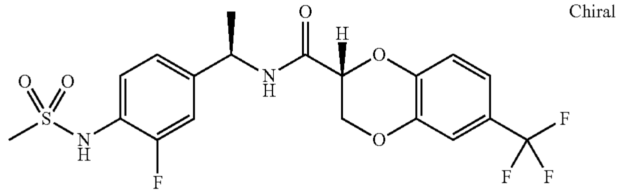 | Chiral | 462.42 | 463.1 | ++++ | |
| 23 | 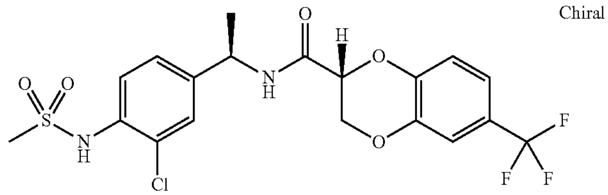 | Chiral | 478.87 | 479.2 | ++++ | |

Determination of pA$_2$ Values Against Capsaicin Stimulation pA$_2$ values of antagonists against the capsaicin agonist dose-response are determined using a Ca$^{2+}$ imaging assay with cells expressing high levels of human VR1 (for explanation of theory behind pA$_2$ determinations, see *A Pharmacological Primer: Theory, Applications, and Methods* 2$^{nd}$ edition by Terry P. Kenakin, pp. 102-108, Academic Press, New York, 2006).

Cell preparation, test compound additions, and capsaicin additions are all performed as mentioned above for the IC$_{50}$ determinations, however instead of running a dose-range of test compound against one concentration of agonist, a dose-range of capsaicin is run against vehicle and a few concentrations of test compound. After test compound addition, capsaicin plus the appropriate concentration of antagonist in saline is added at varying concentrations to achieve final concentrations covering the range of 17 pM-3 uM final capsaicin and the same final concentration of antagonist, or vehicle control, that is already in the well from the antagonist pre-incubation step described above. Changes in the fluorescence signal (λex=470-495 nm, λem=515-575 nm) are monitored throughout the experiment before agonist addition and for at least 2 min after agonist addition (enough time for the fluorescence response to reach and then decline from the absolute maximum, agonist-induced signal attained). For each well, final relative fluorescence units (RFUs) are calculated as the difference between the maximum fluorescence signal obtained in the experiment after agonist addition and the signal level seen at baseline before agonist, but after antagonist, addition (the absolute minimum level of fluorescence signal observed in the 10 seconds prior to agonist addition). These final RFU values are plotted against the corresponding capsaicin concentrations to obtain dose response curves across the capsaicin dose range tested; one dose response curve for each concentration of antagonist tested and one for the capsaicin dose-response without any antagonist (vehicle control). Data are fit to an ideal curve utilizing the 4-parameter sigmoid curve-fit function in GraphPad Prism software (version 4, GraphPad Software, Inc., San Diego, Calif., USA) from which an EC$_{50}$ value is obtained. The dose ratio (DR) is then calculated for each concentration of antagonist tested as the ratio of the EC$_{50}$ value of the dose-response curve of capsaicin in the presence of a given concentration of antagonist divided by the EC$_{50}$ value of the dose-response curve of capsaicin without antagonist (vehicle control). For each antagonist, at least three concentrations are tested. Dose Ratio values are then used to make a standard Schild plot–log [antagonist concentration] plotted against log[DR–1], see Kenakin reference above for theoretical background and method. A linear regression curve-fit is then performed on these plotted points. If the linear regression provided an $R^2$ value 0.8 AND there are at least two concentrations of antagonist tested that provided a DR value greater than 1, then pA$_2$ values are calculated and reported as pA$_2$=Log(DR–1)–Log[antagonist] for the lowest concentration of antagonist tested for which (DR–1)>0. If these conditions are not met, then the antagonist is rerun in a pA$_2$ assay using different antagonist concentrations until the above conditions are met.

Half-life in Human Liver Microsomes (HLM)

Exemplary compounds of the invention are tested (1 μM), and are incubated with 3.3 mM MgCl$_2$ and 0.78 mg/mL HLM (HL101) in 100 mM potassium phosphate buffer (pH 7.4) at 37° C. on the 96-deep well plate. The reaction mixture is split into two groups, a non-P450 and a P450 group. NADPH is only added to the reaction mixture of the P450 group. An aliquot of samples of the P450 group is collected at 0, 10, 30, and 60 minute time points, where the 0 minute time point indicated the time when NADPH is added into the reaction mixture of the P450 group. An aliquot of samples of the non-P450 group is collected at −10 and 65 minute time points. Collected aliquots are extracted with an acetonitrile solution containing an internal standard. The precipitated protein is spun down in a centrifuge (2000 rpm, 15 min). The compound concentration in supernatant is measured by LC/MS/MS system. The half-life value ($T_{1/2}$) is obtained by plotting the natural logarithm of the peak area ratio of compounds/internal standard versus time. The slope of the line of best fit through the points yields the rate of metabolism (k). This is converted to a half-life value using following equations: Half-life=ln 2/k.

Pharmacokinetic Evaluation of Compounds Following Intravenous and Oral Administration in Rats.

Male Sprague-Dawley rats are acclimatized for at least 24 hours prior to experiment initiation. During acclimation period, all animals receive food and water ad libitum. However, food but not water is removed from the animal's cages at least 12 hours before initiation of the experiment. During the first 3 hours of experimentation, the animals receive only water ad libitum. At least three animals each are tested for intravenous and oral dosage. For intravenous formulation, compounds are dissolved (0.25 to 1 mg/mL) in a mixture of 3% dimethyl sulfoxide, 40% PEG 400 and the rest percentage of 40% Captisol in water (w/v). For oral formulation, compounds of this invention are dissolved (2 mg/mL) in a mixture of 5% of 10% Tween 80 in water (v/v) and 95% of 0.5% methyl cellulose in water (w/v). The animals are weighed before dosing. The determined body weight is used to calculate the dose volume for each animal.

For intravenous dosing: Dose volume (mL/kg)=1 mg/kg/formulation concentration (mg/mL).

In instances where the formulation concentrations are less than 0.5 mg/mL, the dosing volume is about 2 mL/kg. PO rats are typically dosed through oral gavage at 2.5 mL/kg to achieve a dose level of 5 mg/kg. For IV dosing, blood samples are collected (using a pre-heparinized syringe) via the jugular vein catheter at 2, 5, 15, 30, 60, 120, 180, 300, 480, and 1440 minutes post dosing. For PO dosing, blood samples are collected (using a pre-heparinized syringe) via the jugular vein catheter before dosing and at 5, 15, 30, 60, 120, 180, 300, 480, and 1440 minutes post dosing. About 250 uL of blood is obtained at each time point from the animal. Equal volumes of 0.9% normal saline are replaced to prevent dehydration. The whole blood samples are maintained on ice until centrifugation. Blood samples are then centrifuged at 14,000 rpm for 10 minutes at 4° C. and the upper plasma layer transferred into a clean vial and stored at −80° C. The resulting plasma samples are then analyzed by liquid chromatography-tandem mass spectrometry. Following the measurement of plasma samples and dosing solutions, plasma concentration-time curve is plotted. Plasma exposure is calculated as the area under the concentration-time curve extrapolated to time infinite ($AUC_{inf}$). The $AUC_{inf}$ is averaged and the oral bioavailability (% F) for individual animal is calculated as:

AUCinf(IV,average)/AUCinf(PO), normalized to their respective dose levels.

The % F is reported as the mean % F of all oral dosed animals.

EXAMPLE 1

Calcium Imaging Assay

VR1 protein is a heat-gated cation channel that exchanges approximately ten calcium ions for every sodium ion resulting in neuronal membrane depolarization and elevated intracellular calcium levels. Therefore the functional activity of compounds at the VR1 receptor may be determined by measuring changes in intracellular calcium levels in neurons such as the dorsal root ganglion.

DRG neurons are grown on PDL coated 96-well black-walled plates, in the presence of DMEM medium containing 5% Penstrep, 5% Glutamax, 200 μg/ml hygromycin, 5 μg/ml blasticide and 10% heat inactivated FBS. Prior to assay, cells are loaded with 5 μg/ml Fura2 in normal saline solution at 37° C. for 40 minutes. Cells are then washed with normal saline to remove dye before commencement of the experiment.

The plated neurons are transferred into a chamber on the stage of a Nikon eclipse TE300 microscope after which neurons are allowed to attain a stable fluorescence for about 10 minutes before beginning the experiment. The assay consists of two stages, a pretreatment phase followed by a treatment phase. First, a solution of the test compound is added from a multivalve perfusion system to the cells for 1 minute (pretreatment). Immediately following, capsaicin (250 nM) is added in the presence of the test compound (treatment) for a specific period between 20 and 60 seconds.

Fura2 is excited at 340 and 380 nM to indicate relative calcium ion concentration. Changes in wavelength measurements are made throughout the course of the experiment. The fluorescence ratio is calculated by dividing fluorescence measured at 340 nM by that at 380 nM. Data are collected using Intelligent Imaging's Slidebook software. All compounds that inhibit capsaicin induced calcium influx greater than 75% are considered positives.

EXAMPLE 2

High Throughput Analysis of VR1 Antagonists for Determination of in vitro Efficacy Using a Calcium Imaging Assay Inhibition of the capsaicin response in the presence and absence of the test compound was measured and assessed, using the method for calcium uptake assay, described hereinabove with respect to the data presented in Table 1. No such reduction in response is observed in the absence of the test compound.

EXAMPLE 3

Whole-cell Patch Clamp Electrophysiology

Dorsal root ganglion (DRG) neurons are recovered from either neonatal or adult rats and plated onto poly-D-lysine coated glass coverslips. The plated neurons are transferred into a chamber to allow drug solutions to be added to the cells using a computer-controlled solenoid-valve based perfusion system. The cells are imaged using standard DIC optics. Cells are patched using finely-pulled glass electrodes. Voltage-clamp electrophysiology experiments are carried out using an Axon Instruments Multiclamp amplified controlled by pCLAMP8 software.

The cells are placed into a whole-cell voltage clamp and held at a voltage of −80 mV while monitoring the membrane current in gap-free recording mode. 500 nM capsaicin is added for 30 seconds as a control. Test compounds at various concentrations are added to the cells for 1 minute prior to a 30 second capsaicin application. Differences between control experiments and drug positive capsaicin experiments are used to determine the efficacy of each test compound. All compounds that inhibit capsaicin induced current greater than 50% are considered positives.

All publications, patents and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims. All such modifications coming within the scope of the appended claims are intended to be included therein.

The chemical names of compounds given in this application were generated using Open Eye Software's Lexichem naming tool, Symyx Renaissance Software's Reaction Planner or MDL's ISIS Draw Autonom Software tool and not verified. Preferably, in the event of inconsistency, the depicted structure governs.

The invention claimed is:
1. A compound of a formula:

(I)

or a pharmaceutically acceptable salt thereof, and stereoisomers and tautomers thereof; wherein:
W represents O, $CR^{8a}R^{8b}$, or $NR^{8c}$;
X represents N, O, $CR^{8a}$, $CR^{8a}R^{8b}$, or $NR^{8c}$;
Y represents $CR^{8d}R^{8e}$;
at least one of W', X', and Y' represents N and the rest each independently represents $CR^8$;
Z represents $CR^8$ or N; provided that W', X' and Y' are not all N at the same time;
$R^1$ and $R^2$ each independently represent hydrogen, halogen, hydroxy, substituted or unsubstituted alkyl, substituted or unsubstituted alkoxy, alkylthio, alkylsulfinyl or alkylsulfonyl;
$R^3$ represents hydrogen, halogen, hydroxy, substituted or unsubstituted alkyl, substituted or unsubstituted alkoxy, acyl, substituted or unsubstituted amino, substituted or unsubstituted alkylamino, substituted or unsubstituted dialkylamino, substituted or unsubstituted cycloalkyl, substituted or unsubstituted heterocycloalkyl, or substituted or unsubstituted heteroaryl;
$R^4$ and $R^5$ each independently represent hydrogen or substituted or unsubstituted alkyl;
$R^7$ represents $(C_1-C_6)$alkyl;
each $R^8$ independently represents hydrogen, halogen, hydroxy, substituted or unsubstituted alkyl, substituted or unsubstituted alkoxy, acyl, substituted or unsubstituted amino, substituted or unsubstituted alkylamino, substituted or unsubstituted dialkylamino, substituted or unsubstituted cycloalkyl, substituted or unsubstituted heterocycloalkyl, substituted or unsubstituted aryl, substituted or unsubstituted heteroaryl, alkylthio, alkylsulfinyl or alkylsulfonyl;

each $R^{8a}$, $R^{8b}$, $R^{8d}$, $R^{8e}$ and $R^{8f}$ independently represents hydrogen, halo, hydroxy, or substituted or unsubstituted alkyl; provided that when the dotted bond is a double bond $R^{8f}$ is absent;
$R^{8c}$ represents hydrogen, or substituted or unsubstituted alkyl; and
the dotted bond represents a single or a double bond; provided that
i) when W and X both are O, and Y' is $CR^8$; then at least one of $R^3$ and $R^8$ is other than H; and
ii) when W and X both are $CH_2$, W' is N, and Y' is $CR^8$; then at least one of $R^3$ and $R^8$ is other than H.

2. A compound according to claim 1 wherein (II)

W, W', X, X', Y', Z, and $R^7$ are as in claim 1;
$R^1$ and $R^2$ each independently represent hydrogen, halogen, hydroxy, $(C_1-C_6)$alkyl, $(C_1-C_6)$alkoxy, hydroxy $(C_1-C_6)$alkoxy, $(C_1-C_6)$alkoxy-$(C_1-C_6)$alkyl, $(C_1-C_6)$alkoxy-$(C_1-C_6)$alkoxy, halo$(C_1-C_6)$alkyl, $(C_1-C_6)$alkylthio, $(C_1-C_6)$alkylsulfinyl or $(C_1-C_6)$alkylsulfonyl;
$R^3$ represents
  hydrogen, halogen, hydroxy, $(C_1-C_6)$alkyl, halo$(C_1-C_6)$alkyl, hydroxy$(C_1-C_6)$alkyl, halo hydroxy$(C_1-C_6)$alkyl, $(C_1-C_6)$alkoxy, hydroxy$(C_1-C_6)$alkoxy, $(C_1-C_6)$alkoxy-$(C_1-C_6)$alkyl, $(C_1-C_6)$acyl, $(C_1-C_6)$alkoxy-$(C_1-C_6)$alkoxy, [$(C_1-C_6)$alkyl]NH—, [$(C_1-C_6)$alkyl]$_2$N—, [hydroxy$(C_1-C_6)$alkyl]NH—, substituted or unsubstituted 3-6 membered cycloalkyl, [3-6 membered cycloalkyl]oxy, or [3-6 membered heterocycloalkyl]oxy or
  3-6 membered heterocycloalkyl, unsubstituted or substituted with halo, $(C_1-C_6)$alkyl, halo$(C_1-C_6)$alkyl, hydroxy$(C_1-C_6)$alkyl, $(C_1-C_6)$alkoxy, [$(C_1-C_6)$alkyl]$_2$N—, or hydroxy, or
  3-6 membered heteroaryl, 3-6 membered cycloalkyl $(C_1-C_6)$alkyl, or 3-6 membered cycloalkyl hydroxy $(C_1-C_6)$alkyl;
$R^4$ represents hydrogen, $(C_1-C_6)$alkyl, halogen, halo$(C_1-C_6)$alkyl, or hydroxy$(C_1-C_6)$alkyl;
each $R^8$ independently represents
  hydrogen, halogen, hydroxy, $(C_1-C_6)$alkyl, $(C_1-C_6)$alkoxy, hydroxy$(C_1-C_6)$alkoxy, $(C_1-C_6)$alkoxy-$(C_1-C_6)$alkyl, $(C_1-C_6)$alkoxy-$(C_1-C_6)$alkoxy, halo$(C_1-C_6)$alkyl, halo hydroxy$(C_1-C_6)$alkyl, $(C_1-C_6)$alkylthio, $(C_1-C_6)$alkylsulfinyl, [$(C_1-C_6)$alkyl]NH—, [$(C_1-C_6)$cycloalkyl]NH—, [$(C_1-C_6)$alkyl]$_2$N—, [hydroxy$(C_1-C_6)$alkyl]NH—, [3-6 membered cycloalkyl]oxy, [3-6 membered heterocycloalkyl]oxy or
  3-6 membered heterocycloalkyl, unsubstituted or substituted with halo, $(C_1-C_6)$alkyl, $(C_1-C_6)$alkoxy, halo $(C_1-C_6)$alkyl, hydroxy$(C_1-C_6)$alkyl, aryl$(C_1-C_6)$alkyl, [$(C_1-C_6)$alkyl]$_2$N—, $(C^1-C_6)$carbalkoxy, hydroxy, aryl, $(C_1-C_6)$alkylaryl, halo$(C_1-C_6)$alkylaryl, haloaryl, $(C_1-C_6)$alkoxyaryl, or 3-10 membered heteroaryl, 3-6 membered cycloalkyl ($C_1$-$C_6$)alkyl, or 3-6 membered cycloalkyl hydroxy ($C_1$-$C_6$)alkyl or ($C_1$-$C_6$)alkylsulfonyl;

each $R^{8a}$, $R^{8b}$, $R^{8d}$, $R^{8e}$ and $R^{8f}$ independently represents hydrogen, halo, hydroxy, ($C_1$-$C_6$)alkyl, hydroxy($C_1$-$C_6$) alkyl, ($C_1$-$C_6$)alkoxy-($C_1$-$C_6$)alkyl, or halo($C_1$-$C_6$) alkyl; provided that when the dotted bond is a double bond $R^{8f}$ is absent;

$R^{8c}$ represents hydrogen, ($C_1$-$C_6$)alkyl, hydroxy($C_1$-$C_6$) alkyl, ($C_1$-$C_6$)alkoxy-($C_1$-$C_6$)alkyl, cycloalkyl, or halo ($C_1$-$C_6$)alkyl; and the dotted bond represents a single or a double bond.

3. A compound according to claim 1, wherein one of W', X', Y' and Z represent N and the rest each independently represent $CR^8$.

4. A compound according to claim 1, wherein two of W', X', Y' and Z represent N and the rest each independently represent $CR^8$.

5. A compound according to claim 1, wherein W and X each independently represent $CR^{8a}R^{8b}$; and the dotted bond is a single bond.

6. A compound according to claim 1, wherein W and X each independently represent $CH_2$; and the dotted bond is a single bond.

7. A compound according to claim 1, wherein W represents $CR^{8a}R^{8b}$; X represents $CR^{8a}$; and the dotted bond is a double bond.

8. A compound according to claim 1, wherein W represents $CH_2$; X represents CH; and the dotted bond is a double bond.

9. A compound according to claim 1, wherein X represents $NR^{8c}$; and the dotted bond is a single bond.

10. A compound according to claim 1, wherein X represents O; and the dotted bond is a single bond.

11. A compound according to claim 1, wherein W represents $NR^{8c}$.

12. A compound according to claim 1, wherein W represents O.

13. A compound according to claim 1, wherein Y represents $CR^{8d}R^{8e}$.

14. A compound according to claim 1, wherein Y represents $CH_2$.

15. A compound according to claim 1 wherein the compound is according to formulae IIa, IIb, IIc, IId, IIe, IIf, IIg, IIh or IIi:

IIa
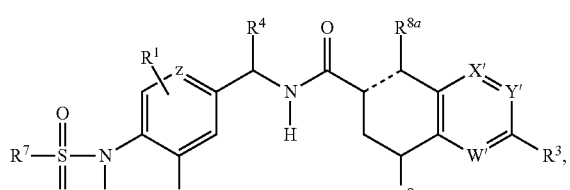

IIb
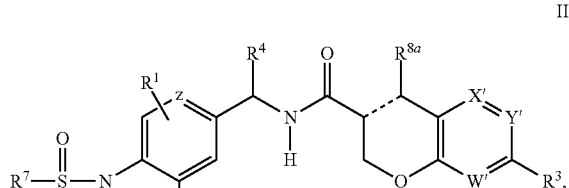

IIc
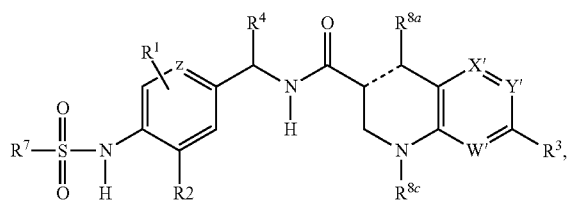

IId
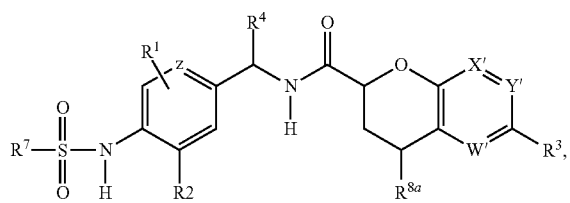

IIe
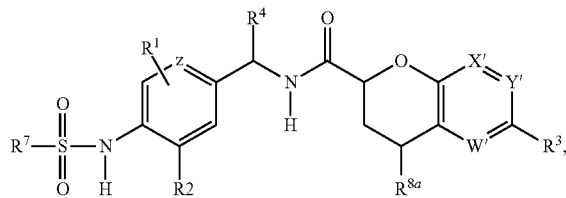

IIf
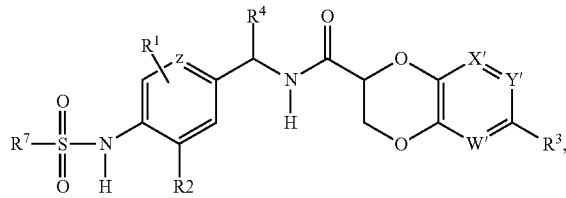

IIg
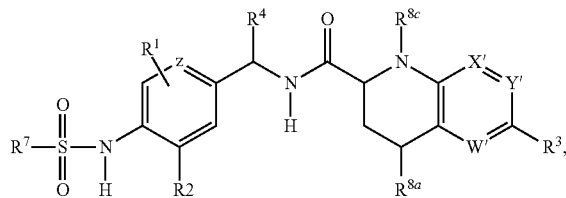

IIh
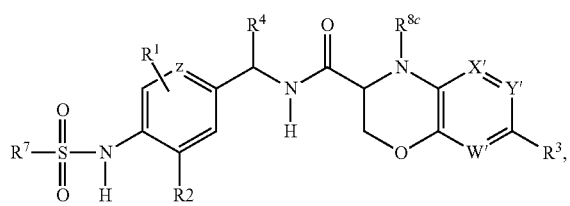

IIi
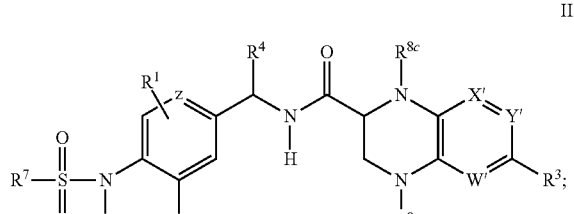

or a pharmaceutically acceptable salt, and stereoisomers and tautomers thereof, wherein W', X', Y', Z, $R^1$, $R^2$, $R^3$, $R^4$, $R^7$, $R^{8a}$ and $R^{8c}$ are as in claim 1.

16. A compound according to claim 1, wherein $R^1$ represents hydrogen, halogen or ($C_1$-$C_6$)alkyl.

17. A compound according to claim 1, wherein $R^1$ represents H or F.

18. A compound according to claim 15, wherein the compound is according to formula IIa, IIb or IIc and the dotted bond is a single bond.

19. A compound according to claim 15 wherein the compound is according to formula IIa, IIb or IIc and the dotted bond is a double bond.

20. A compound according to claim 15 wherein one of W', X', and Y' represents N and the rest each independently represents $CR^8$.

21. A compound according to claim 15 wherein W' is N and each of X', and Y' is independently $CR^8$.

22. A compound according to claim 15 wherein W' is N and each of X', and Y' is independently CH.

23. A compound according to claim 1 wherein the compound is according to formulae IVa, IVb, IVc, IVd, IVe, IVf, IVg, IVh or IVi:

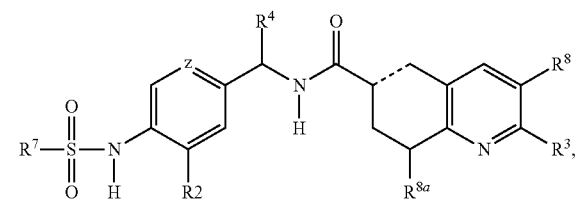

IVa

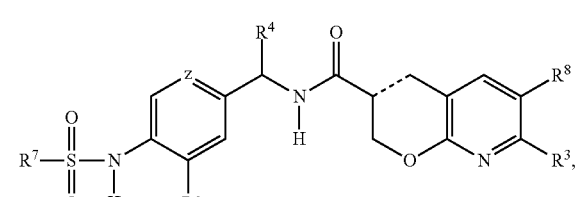

IVb

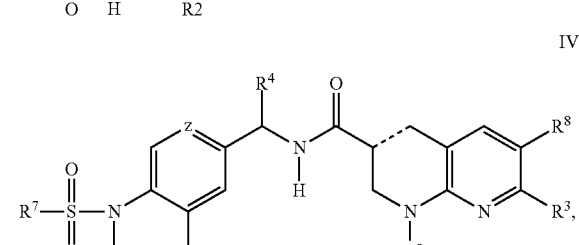

IVc

IVd

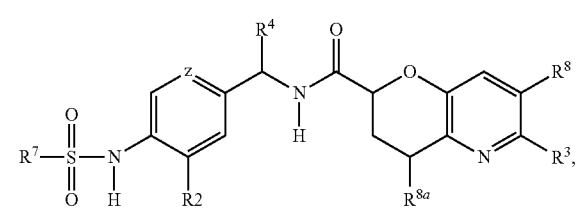

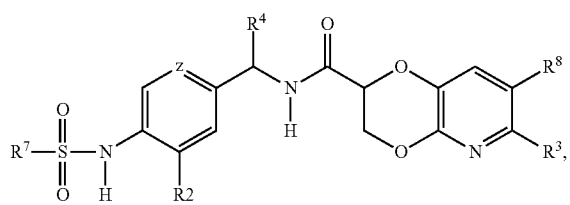

IVe

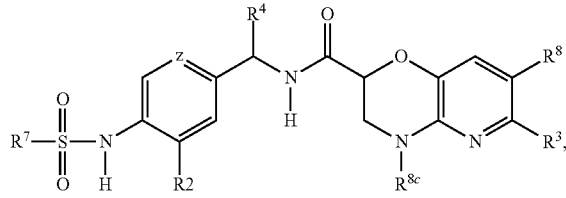

IVf

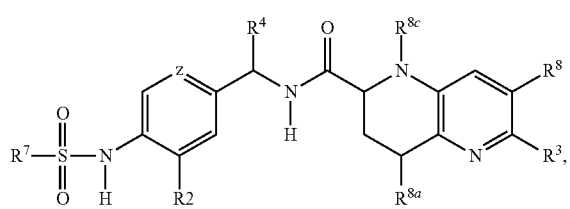

IVg

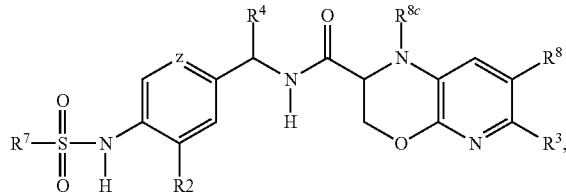

IVh

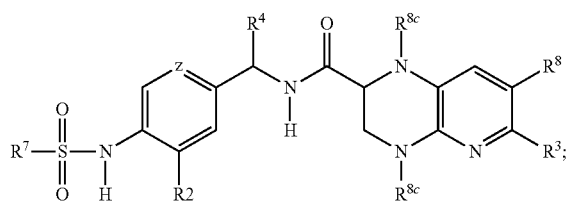

IVi or a pharmaceutically acceptable salt, and stereoisomers and tautomers thereof, wherein Z, $R^2$, $R^3$, $R^4$, $R^7$, $R^8$, and $R^{8C}$ are as in claim 1.

24. A compound according to claim 1 wherein the compound is according to formulae Va, Vb, Vc, Vd, Ve, Vf, Vg, Vh or Vi:

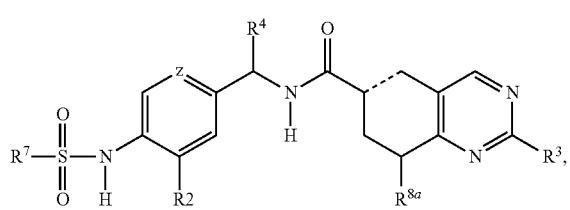

Va or a pharmaceutically acceptable salt, and stereoisomers and tautomers thereof, wherein Z, $R^2$, $R^3$, $R^4$, $R^7$, and $R^{8c}$ are as in claim 1.

25. A compound according to claim 1 wherein Z represents CH, CF or CCl.

26. A compound according to claim 1 wherein Z represents N.

27. A compound according to claim 1 wherein $R^2$ represents halogen, ($C_1$-$C_6$)alkyl, halo($C_1$-$C_6$)alkyl or hydroxy ($C_1$-$C_6$)alkyl.

28. A compound according to claim 1 wherein $R^2$ represents F or methyl.

29. A compound according to claim 1 wherein $R^2$ represents Me and Z represents CF.

30. A compound according to claim 1 wherein the compound is according to formula IVa-IVc, and Va-Vc, and the dotted bond is a single bond.

31. A compound according to claim 23 or 27 wherein the compound is according to formula IVa-IVc, and Va-Vc, and the dotted bond is a double bond.

32. A compound according to claim 1 wherein $R^3$ or $R^8$ is H.

33. A compound according to claim 1 wherein $R^3$ or $R^8$ independently represents OMe, OEt, COMe, $NMe_2$, or $NEt_2$.

34. A compound according to claim 1 wherein $R^3$ or $R^8$ is independently F, Br, or Cl.

35. A compound according to claim 1 wherein $R^3$ or $R^8$ is independently Me, i-Pr, t-Bu, 1-methyl-1-trifluoromethyl-ethyl, or 1-methyl-1-hydroxyethyl.

36. A compound according to claim 1 wherein $R^3$ or $R^8$ is independently $CF_3$.

37. A compound according to claim 1 wherein $R^3$ or $R^8$ is independently 3-6 membered cycloalkyl.

38. A compound according to claim 1 wherein $R^3$ or $R^8$ is independently cyclopropyl, 1-methylcyclopropyl, 1-hydroxycyclopropyl, 1-trifluoromethylcyclopropyl, cyclobutyl or cyclopentyl.

39. A compound according to claim 1 wherein $R^3$ or $R^8$ is independently 3-6 membered heterocycloalkyl.

40. A compound according to claim 1 wherein $R^3$ or $R^8$ is independently 41. A compound according to claim 1 wherein $R^3$ or $R^8$ is independently —C(OMe)(Me)CF$_3$, —C(OH)(Me)CF$_3$, —C(Me)$_2$OH or —C(Me)(OH)-cyclopropyl.

42. A compound according to claim 1 wherein $R^4$ is hydrogen.

43. A compound according to claim 1 wherein $R^4$ is (C$_1$-C$_6$)alkyl.

44. A compound according to claim 1 wherein $R^4$ is methyl.

45. A compound according to claim 1 wherein $R^7$ is alkyl.

46. A compound according to claim 1 wherein $R^7$ is Me, Et, Pr, i-Pr, or t-butyl.

47. A compound according to claim 1 wherein $R^{8C}$ is H or Me.

48. A compound according to claim 1, selected from 2-(2,2,2-Trifluoro-1,1-dimethyl-ethyl)-5,6,7,8-tetrahydro-quinoline-6-carboxylic acid [(R)-1-(2-fluoro-4-methanesulfonylamino-5-methyl-phenyl)-ethyl]-amide;

2-(2,2,2-Trifluoro-1,1-dimethyl-ethyl)-5,6,7,8-tetrahydro-quinoline-6-carboxylic acid [(R)-1-(2-fluoro-4-methanesulfonylamino-5-methyl-phenyl)-ethyl]-amide;

2-(2,2,2-Trifluoro-1,1-dimethyl-ethyl)-5,6,7,8-tetrahydro-quinoline-6-carboxylic acid [(R)-1-(2-fluoro-4-methanesulfonylamino-5-methyl-phenyl)-ethyl]-amide;

(S)-5,6,7,8-Tetrahydro-quinoline-6-carboxylic acid [(R)-1-(2-fluoro-4-methanesulfonylamino-5-methyl-phenyl)-ethyl]-amide;

(R)-5,6,7,8-Tetrahydro-quinoline-6-carboxylic acid [(R)-1-(2-fluoro-4-methanesulfonylamino-5-methyl-phenyl)-ethyl]-amide;

2-(1-Hydroxy-1-methyl-ethyl)-5,6,7,8-tetrahydro-quinoline-6-carboxylic acid [(R)-1-(2-fluoro-4-methanesulfonylamino-5-methyl-phenyl)-ethyl]-amide;

(R)-2-(1-Methoxy-1-methyl-ethyl)-5,6,7,8-tetrahydro-quinoline-6-carboxylic acid [(R)-1-(2-fluoro-4-methanesulfonylamino-5-methyl-phenyl)-ethyl]-amide;

(S)-2-(1-Methoxy-1-methyl-ethyl)-5,6,7,8-tetrahydro-quinoline-6-carboxylic acid [(R)-1-(2-fluoro-4-methanesulfonylamino-5-methyl-phenyl)-ethyl]-amide;

(S)-2-(2-Methyl-[1,3]dioxolan-2-yl)-5,6,7,8-tetrahydro-quinoline-6-carboxylic acid [(R)-1-(2-fluoro-4-methanesulfonylamino-5-methyl-phenyl)-ethyl]-amide; and 6-Trifluoromethyl-2,3-dihydro-[1,4]dioxino[2,3-b]pyridine-2-carboxylic acid [(R)-1-(2-fluoro-4-methanesulfonylamino-5-methyl-phenyl)-ethyl]-amide;

or a pharmaceutically acceptable salt thereof, and stereoisomers and tautomers thereof.

49. A pharmaceutical composition comprising a pharmaceutically acceptable carrier and a pharmaceutically effective amount of a compound of claim 1.

50. The pharmaceutical composition of claim 49 wherein the carrier is a parenteral carrier, oral or topical carrier.

51. A method for treating a disease or condition which comprises administering to a patient in need of a therapeutically effective amount of a compound of claim 1, or the pharmaceutical composition of claim 49, wherein the disease or condition is a pain condition.

52. A method for treating a disease or condition which comprises administering to a patient in need of a therapeutically acceptable amount of a compound of claim 1, or the pharmaceutical composition of claim 49, wherein the disease is: pain including acute, inflammatory and neuropathic pain; chronic pain; dental pain; and headache including migraine, cluster headache and tension headache.

53. The method of claim 52 wherein the disease or condition is neuropathic pain.

54. The method of claim 53 wherein the pain is associated with a condition selected from the group consisting of post-mastectomy pain syndrome, stump pain, phantom limb pain, oral neuropathic pain, Charcot's pain, toothache, venomous snake bite, spider bite, insect sting, postherpetic neuralgia, diabetic neuropathy, reflex sympathetic dystrophy, trigeminal neuralgia, osteoarthritis, rheumatoid arthritis, fibromyalgis, Guillain-Barre syndrome, meralgia paresthetica, burning-mouth syndrome, bilateral peripheral neuropathy, causalgia, sciatic neuritis, peripheral neuritis, polyneuritis, segmental neuritis, Gombault's neuritis, neuronitis, cervicobrachial neuralgia, cranial neuralgia, egniculate neuralgia, glossopharyngial neuralgia, migranous neuralgia, idiopathic neuralgia, intercostals neuralgia, mammary neuralgia, mandibular joint neuralgia, Morton's neuralgia, nasociliary neuralgia, occipital neuralgia, red neuralgia, Sluder's neuralgia, splenopalatine neuralgia, supraorbital neuralgia, vidian neuralgia, sinus headache, tension headache, labor, childbirth, intestinal gas, menstruation, cancer, and trauma.

\* \* \* \* \*

UNITED STATES PATENT AND TRADEMARK OFFICE
CERTIFICATE OF CORRECTION

PATENT NO. : 8,153,651 B2
APPLICATION NO. : 12/742425
DATED : April 10, 2012
INVENTOR(S) : Matthew Cox et al.

Page 1 of 1

It is certified that error appears in the above-identified patent and that said Letters Patent is hereby corrected as shown below:

Title page, item (73) Assignee should read as follows: Evotec AG, Hamburg (DE) and Pfizer Global Research and Development, Kent (GB)

Signed and Sealed this
Fourth Day of June, 2013

Teresa Stanek Rea
*Acting Director of the United States Patent and Trademark Office*